US012702714B2

(12) United States Patent
Puisis et al.

(10) Patent No.: US 12,702,714 B2
(45) Date of Patent: Aug. 11, 2026

(54) TREATMENT OF IMMUNE EVASIVE TUMORS

(71) Applicant: onCour Pharma, Inc., Northbrook, IL (US)

(72) Inventors: John Puisis, Northbrook, IL (US); Adam Elhofy, Northbrook, IL (US); Tushar Murthy, Northbrook, IL (US); Michael Boyne, Northbrook, IL (US); Joseph Podojil, Northbrook, IL (US)

(73) Assignee: onCour Pharma, Inc., Northbrook, IL (US)

( * ) Notice: Subject to any disclaimer, the term of this patent is extended or adjusted under 35 U.S.C. 154(b) by 711 days.

(21) Appl. No.: 17/631,277

(22) PCT Filed: Jul. 31, 2020

(86) PCT No.: PCT/US2020/044622

§ 371 (c)(1), (2) Date: Jan. 28, 2022

(87) PCT Pub. No.: WO2021/022218

PCT Pub. Date: Feb. 4, 2021

(65) Prior Publication Data

US 2022/0257768 A1 Aug. 18, 2022

Related U.S. Application Data

(60) Provisional application No. 63/018,026, filed on Apr. 30, 2020, provisional application No. 62/881,326, filed on Jul. 31, 2019.

(51) Int. Cl.

| | |
|---|---|
| ***A61K 31/765*** | (2006.01) |
| ***A61K 9/14*** | (2006.01) |
| ***A61K 39/00*** | (2006.01) |
| ***A61K 45/06*** | (2006.01) |
| ***A61K 47/06*** | (2006.01) |
| ***A61K 47/34*** | (2017.01) |
| ***A61P 35/00*** | (2006.01) |
| ***C07K 16/24*** | (2006.01) |
| ***C07K 16/28*** | (2006.01) |

(52) U.S. Cl.

CPC ................ *A61K 47/34* (2013.01); *A61K 9/14* (2013.01); *A61K 47/06* (2013.01); *A61P 35/00* (2018.01)

(58) Field of Classification Search

CPC .......... A61K 47/34; A61K 9/14; A61K 47/06; A61K 2039/545; A61K 31/765; A61K 45/06; A61K 2300/00; A61P 35/00; C07K 2317/73; C07K 16/244; C07K 16/2818

See application file for complete search history.

(56) References Cited

U.S. PATENT DOCUMENTS

| | | | | |
|---|---|---|---|---|
| 9,616,113 | B2 | 4/2017 | Lonnie | |
| 11,045,492 | B2 * | 6/2021 | Puisis | A61K 39/001 |
| 2008/0193372 | A1 * | 8/2008 | Lanza | A61K 51/1234 424/9.4 |
| 2011/0044911 | A1 | 2/2011 | Akhtari et al. | |
| 2015/0190485 | A1 * | 7/2015 | Shea | A61P 19/06 424/499 |
| 2018/0369407 | A1 * | 12/2018 | Goldberg | C07K 16/2803 |

FOREIGN PATENT DOCUMENTS

| | | | |
|---|---|---|---|
| JP | 2019504877 | A | 2/2019 |
| JP | 2021532136 | A | 11/2021 |
| WO | WO-2017112899 | A1 | 6/2017 |
| WO | WO-2017143346 | A1 | 8/2017 |
| WO | WO-2018122249 | A1 | 7/2018 |
| WO | WO-2019149743 | A1 | 8/2019 |
| WO | WO-2020/028544 | A1 | 2/2020 |
| WO | WO-2020068347 | A1 | 4/2020 |

OTHER PUBLICATIONS

Rodallec, A., Sicard, G., Fanciullino, R., Benzekry, S., Lacarelle, B., Milano, G., & Ciccolini, J. (2018). Turning cold tumors into hot tumors: harnessing the potential of tumor immunity using nanoparticles. Expert Opinion on Drug Metabolism & Toxicology, 14(11), 1139-1147. (Year: 2018).*

Asano, K. et al. "CD169-Positive Macrophages Dominate Antitumor Immunity by Crosspresenting Dead Cell-Associated Antigens," Immunity, Jan. 28, 2011, 34:85-95.

Astete, C. E, et al., "Synthesis and characterization of PLGA nanoparticles," J. Biomater. Sci. Polymer Edn., 2006, 17(3):247-289.

AVASTIN® (bevacizumab), injection, for intravenous use, Highlights of Prescribing Information / Package Insert / Label/ Full Prescribing Information, Genentech, Inc., South San Francisco, CA; Revised: Jun. 2019, Reference ID: 4451519, Initial U.S. Approval: 2004, 39 pages.

BAVENCIO® (avelumab) injection, for intravenous use, Highlights of Prescribing Information / Package Insert / Label/ Full Prescribing Information, EMD Serono, Inc., New York, NY; Revised: May 2019, Reference ID: 4433254, Initial U.S. Approval: 2017, 34 pages.

Bonaventura, P. et al. "Cold Tumors: A Therapeutic Challenge for Immunotherapy," Frontiers in immunology, Feb. 8, 2019, 10(168):1-10.

Brown, S.D. et al. "Neo-antigens predicted by tumor genome meta-analysis correlate with increased patient survival," Genome research, 2014, 24:743-750.

Chao, M.P. et al. "The CD47-SIRPα Pathway in Cancer Immune Evasion and Potential Therapeutic Implications," Current opinion in immunology, Apr. 2012, 24(2):225-232.

Dudley, J.C., et al. "Microsatellite Instability as a Biomarker for PD-1 Blockade," Clinical Cancer Research, 2016, 22(4):813-820.

Froimowicz, et al. "Surface-Functionalized Particles: From their Design and Synthesis to Materials Science and Bio-Applications." Current Organic Chemistry, 2013, 17:900-912.

(Continued)

*Primary Examiner* — Walter E Webb
*Assistant Examiner* — Colman Welles
(74) *Attorney, Agent, or Firm* — MARSHALL, GERSTEIN & BORUN LLP

(57) ABSTRACT

The present disclosure provides methods of treating immune evasive cancers using surface functionalized particles alone or in combination with cancer therapeutics.

18 Claims, 29 Drawing Sheets

(56) References Cited

OTHER PUBLICATIONS

Gabrilovich, D. I. et al., "Myeloid-Derived Suppressor Cells," Cancer Immunol Res., Jan. 2017, 5(1):3-8.
Gao, S. et al. "Engineering Nanoparticles for Targeted Remodeling of the Tumor Microenvironment to Improve Cancer Immunotherapy." Theranostics, Jan. 2019, 9(1):126-151.
Georgoudaki, A.M. et al. "Reprogramming Tumor-Associated Macrophages by Antibody Targeting Inhibits Cancer Progression and Metastasis," Cell reports, 2016, 15:2000-2011.
Gibney, G.T. et al. "Predictive biomarkers for checkpoint inhibitor-based immunotherapy," Lancet Oncology, Dec. 2016, 17(12):e542-e551.
IMFINZI® (durvalumab) injection, for intravenous use, Highlights of Prescribing Information / Package Insert / Label/ Full Prescribing Information, AstraZeneca UK Limited, Cambridge, England; Revised: Jul. 2019, Reference ID: 4465139, Initial U.S. Approval: 2017, 27 pages.
IMLYGIC® (talimogene laherparepvec) Suspension for intralesional injection, Highlights of Prescribing Information / Package Insert / Label/ Full Prescribing Information, BioVex, Inc., Thousand Oaks, CA, Revised: Jun. 2022, Initial U.S. Approval: 2015, 16 pages.
INLYTA® (axitinib) Tablets: 1 mg and 5 mg, for oral administration, Label; Highlights of Prescribing Information; Revised: Aug. 2018 (Aug. 2018), Revised: Aug. 2018, Initial U.S. Approval: 2012, Distributed by: Pfizer Inc., New York, NY 10017, USA, 19 pages.
International Search Report and Written Opinion issued in PCT/US2020/044622 dated Dec. 7, 2020, 8 pages.
Joumaa et al., "Synthesis of Quantum Dot-Tagged Submicrometer Polystyrene Particles by Miniemulsion Polymerization," Langmuir, 2006, 22:1810-1816.
Joyce, J.A. et al., "T cell exclusion, immune privilege, and the tumor microenvironment," Science, Apr. 3, 2015, 348(6230):74-80.
KEYTRUDA® (pembrolizumab) for injection, for intravenous use, Highlights of Prescribing Information / Package Insert / Label/ Full Prescribing Information, MerkSharp & Dohme Corp., Whitehouse Station, NJ; Revised: Jul. 2019, Reference ID: 4470211, Initial U.S. Approval: 2014, 83 pages.
Kim, J. et al. "Determining Chemotherapy Tolerance in Older Patients with Cancer," J Natl Compr Canc Netw, Dec. 1, 2013, 11(12):1494-502.
Krishnamurthy, A. et al. "Bispecific antibodies for cancer therapy: A review," Pharmacology and Therapeutics, 2018, 185:122-134.
Kumar, V. et al. "The nature of myeloid-derived suppressor cells in the tumor microenvironment," Trends in immunology, Mar. 2016, 37(3):208-220.
La Fleur, L. et al. "Expression of scavenger receptor MARCO defines a targetable tumor-associated macrophage subset in non-small cell lung cancer, " International Journal of Cancer, 2018, 143:1741-1752.
Le, D.T. et al. "Mismatch repair deficiency predicts response of solid tumors to PD-1 blockade," Science, Jul. 28, 2017, 357(6349):409-413.
Le, D.T. et al. "PD-1 Blockade in Tumors with Mismatch-Repair Deficiency," The New England journal of medicine, May 30, 2015, 372:2509-2520.
Li, J. et al. "Tumor cell-intrinsic factors underlie heterogeneity of immune cell infiltration and response to immunotherapy," Immunity, Jul. 17, 2018, 49(1):178-193.
LIBTAYO® (cemiplimab-rwlc) injection, for intravenous use, Highlights of Prescribing Information / Package Insert / Label/ Full Prescribing Information, Regeneron Pharmaceuticals, Inc., Tarrytown, NY; Revised: Mar. 2019, Initial U.S. Approval: Sep. 2018, 14 pages.
MEKINIST® (trametinib) tablets, for oral use, Highlights of Prescribing Information / Package Insert / Label/ Full Prescribing Information, Novartis Pharmaceuticals Corporation, East Hanover, NJ; Revised: Jul. 2019, Reference ID: 4462799, Initial U.S. Approval: 2013, 35 pages.
Mittal, D. et al. "New insights into cancer immunoediting and its three component phases—elimination, equilibrium and escape," Current Opinion in Immunology, Apr. 2014, 27:16-25.
Nielsen, J. et al. "CD20+ tumor-infiltrating lymphocytes have an atypical CD27—memory phenotype and together with CD8+ T cells promote favorable prognosis in ovarian cancer," Clinical Cancer Research, 2012, 18(12):3281-3292.
O, J.H. et al., "Practical Percist: A Simplified Guide to PET Response Criteria in Solid Tumors 1.0." Radiology, Aug. 2016, 280(2):576-584.
OPDIVO® (nivolumab) injection, for intravenous use, Highlights of Prescribing Information / Package Insert / Label/ Full Prescribing Information, Bristol-Myers Squibb Company, Princeton, NJ; Revised: Mar. 2019, Reference ID: 4427750, Initial U.S. Approval: 2014, 78 pages.
Philips and Atkins, "Therapeutic uses of anti-PD-1 and anti-PD-L1 antibodies," International Immunology, 2014, 27(1):36-46.
Péus, D. et al. "Appraisal of the Karnofsky Performance Status and proposal of a simple algorithmic system for its evaluation," BMC Medical Informatics and Decision Making, 2013, 13(72):1-7.
Qian, B.Z. et al., "Macrophage Diversity Enhances Tumor Progression and Metastasis," Cell, Apr. 2, 2010, 141:39-51.
Rubtsov, A.V. et al. "CD11c-Expressing B Cells Are Located at the T Cell/B Cell Border in Spleen and Are Potent APCs," The Journal of Immunology, 2015, 195:71-79.
Rybinski, B. et al. "Addressing intra-tumoral heterogeneity and therapy resistance," Oncotarget, 2016, 7(4):72322-72342.
Schreiber, R.D. et al. "Cancer Immunoediting: Integrating Immunity's Roles in Cancer Suppression and Promotion," Science, Mar. 25, 2011, 331:1565-1570.
Schrock, A.B. et al. "Tumor mutational burden is predictive of response to immune checkpoint inhibitors in MSI-high metastatic colorectal cancer," Annals of Oncology, Apr. 30, 2019, 30:1096-1103.
Shankaran, V. et al. "IFNγ and lymphocytes prevent primary tumour development and shape tumour immunogenicity," Nature, Apr. 26, 2001, 410:1107-1111.
Song et al., "Synergistic and low adverse effect cancer immunotherapy by immunogenic chemotherapy and locally expressed PD-L1 trap," Nat. Commun. 2018, 9(2237):1-11.
Souza-Fonseca-Guimaraes, F. et al. "The Emergence of Natural Killer Cells as a Major Target in Cancer Immunotherapy," Trends in immunology, Feb. 2019, 40(2):142-158.
Spel, L. et al. "Antitumor immune responses mediated by dendritic cells: How signals derived from dying cancer cells drive antigen cross-presentation," OncoImmunology, Nov. 2013, 2(11):e26403-1-e26403-10.
SPRYCEL® (dasatinib) tablets, for oral use, Highlights of Prescribing Information/ Package Insert / Label/ Full Prescribing Information, Bristol-Myers Squibb Company, Princeton, NJ; Revised: Dec. 2018, Reference ID: 4367770, Initial U.S. Approval: 2006, 47 pages.
Staneva, R. et al. "Cancer cells in the tumor core exhibit spatially coordinated migration patterns," J Cell Sci, Feb. 5, 2019, 132:1-9.
TARCEVA® (erlotinib) tablets, for oral use, Highlights of Prescribing Information / Package Insert / Label/ Full Prescribing Information, OSI Pharmaceuticals, LLC, Northbrook, IL; Revised: Oct. 2016, Reference ID: 4000318, Initial U.S. Approval: 2004, 19 pages.
TECENTRIQ® (atezolizumab) injection, for intravenous use, Highlights of Prescribing Information / Package Insert / Label/ Full Prescribing Information, Genentech, Inc., South San Francisco, CA; Revised May 2019, Reference ID: 4429210, Initial U.S. Approval: 2016, 44 pages.
Therasse, P. et al. "New Guidelines to Evaluate the Response to Treatment in Solid Tumors," JNCI: Journal of the National Cancer Institute, 2000, 92(3):205-216.
Thomas, A. et al. "Tumor mutational burden is a determinant of immune-mediated survival in breast cancer," Oncoimmunology, 2018, 7(10):e1490854:1-10.
Thomas, D.A. et al. "TGF-β directly targets cytotoxic T cell functions during tumor evasion of immune surveillance," Cancer cell, 2005, Nov. 2005, 8:369-380.

(56) References Cited

OTHER PUBLICATIONS

Topalian et al., "Immune Checkpoint Blockade: A Common Denominator Approach to Cancer Therapy," Cancer Cell, Apr. 13, 2015, 27(4):450-461.

Tovoli, F. et al., "Radiologic criteria of response to systemic treatments for hepatocellular carcinoma," Hepat Oncol, 2017, 4(4):129-137.

Trujillo, J.A. et al. "T Cell-Inflamed versus Non-T Cell-Inflamed Tumors: A Conceptual Framework for Cancer Immunotherapy Drug Development and Combination Therapy Selection," Cancer Immunology Research, Sep. 2018, 6(9):990-1000.

Vareki, S. et al. "High and low mutational burden tumors versus immunologically hot and cold tumors and response to immune checkpoint inhibitors," Journal for Immunotherapy of Cancer, 2018, 6(157):1-5.

Vignjevic, D. et al. "Fascin, a Novel Target of β-catenin-TCF Signaling, is Expressed at the Invasive Front of Human Colon Cancer," Cancer Res, Jul. 15, 2007, 67(14):6844-6853.

Yang, et al. "Cancer Cell Membrane-Coated Adjuvant Nanoparticles with Mannose Modification for Effective Anticancer Vaccination." ACS Nano. May 17, 2018, 12:5121-5129.

Yarchoan, M. et al. "Tumor Mutational Burden and Response Rate to PD-1 Inhibition," The New England journal of medicine, Dec. 21, 2017, 377(25):2500-2501.

YERVOY® (ipilimumab) injection, for intravenous use, Highlights of Prescribing Information / Package Insert / Label/ Full Prescribing Information, Bristol-Myers Squibb Company, Princeton, NJ; Revised: May 2019, Reference ID: 4430687, Initial U.S. Approval: 2011, 52 pages.

Yu, et al. "Recent advances of bispecific antibodies in solid tumors." J of Hematol. and Oncol., 2017, 10(155):1-16.

Chen et al., Photothermal therapy with immune-adjuvant nanoparticles together with checkpoint blockade for effective cancer immunotherapy, Nature Communications, 7(1):1-13 (Oct. 21, 2016).

Min et al., Antigen-capturing nanoparticles improve the abscopal effect and cancer immunotherapy—Supplementary Information, Nature Nanotechnology, 12(9):877-882 (Jun. 26, 2017).

Min et al., Antigen-capturing nanoparticles improve the abscopal effect and cancer immunotherapy, Nature Nanotechnology, 12(9):877-882 (2017).

* cited by examiner (A)
Cell Viability
% Live
Vehicle
SFP
anti-PD1
Combo
(B)
B16F10 Tumor Volume
Tumor Volume (mm3)
Vehicle
SFP
anti-PD1
Combo
(C)
Survival
Percent survival
Vehicle
SFP
anti-PD1
Combo
(D)
MSDCs (CD11b+Ly6G+)
% CD45+
p=0.055
ns
(E)
TAMs (CD11b+F4/80+)
% CD45+
ns
(F)
NK (CD3- NK1.1+)
% CD3- NK1.1+
ns
p=0.056

Saline (5/7)

Anti-PD1 (7/8)

Day 1 CNP-301 (0/7)

Day 2 CNP-301 (1/8)

Day 4 CNP-301 (2/8)

Day 5 CNP-301 (3/8)

(A)
MIP-1β
Saline
CNP-301
Serum (pg/ml)
300
200
100
0
8
14
20
Day Post Tumor Cell Injection
*
*
(B)
TNF-α
Saline
CNP-301
Serum (pg/ml)
250
200
150
100
50
0
8
14
20
Day Post Tumor Cell Injection
**
*
(C)
RANTES (CCL5)
Saline
ONC-101
Serum (pg/ml)
150
100
50
0
8
14
20
Day Post Tumor Cell Injection
***
****

(A)
Blood PD-L1+ (Monocytes)
Saline
CNP-301
Percentage of CD11b+/Ly6C+/Ly6G-
0
20
40
60
80
100
8
14
20
Day Post Tumor Cell Injection
**
****
(B)
Blood PD-L1+ (Granulocytes)
Saline
CNP-301
Percentage of CD11b+/Ly6C+/Ly6G+
0
20
40
60
80
100
8
14
20
Day Post Tumor Cell Injection
*
**

(C)

(D)

(E)

(F)

(G)

(A)
Tumor Cell-surface IL-15+
Saline
CNP-301
Percentage of CD45+ Cells
100
80
60
40
20
0
**
8
14
20
Day Post Tumor Cell Injection
(B)
Tumor Granzyme B+
Saline
CNP-301
Percentage of NK cells Cells
100
80
60
40
20
0
***
8
14
20
Day Post Tumor Cell Injection (A)
MIP-1β
Saline
CNP-301
Serum (pg/ml)
300
200
100
0
8
14
20
**
Day Post Tumor Cell Injection
(B)
TNF-α
Saline
CNP-301
Serum (pg/ml)
250
200
150
100
50
0
8
14
20
*
***
Day Post Tumor Cell Injection
(C)
RANTES (CCL5)
Saline
CNP-301
Serum (pg/ml)
100
80
60
40
20
0
8
14
20
*
Day Post Tumor Cell Injection (D)

(E)

(A)

(B)

(C)
Blood Cell-surface IL-15$^{+}$
Saline
CNP-301
****
Percentage of CD45+ Cells
100
80
60
40
20
0
7
14
20
Day Post Tumor Cell Injection
(D)
Blood Total NK cells
Saline
CNP-301
**
Percentage of CD45+ Cells
100
80
60
40
20
0
7
14
20
Day Post Tumor Cell Injection (E)

(F)

(G)

(B)

(A)

(A)

(B)
Tumor
% positive cells
100
75
50
25
0
TAM
Fibrobablsts
PMN-MDSC
M-MDSC (C)

(D)
Spleen
% positive cells
100
75
50
25
0
Macrophages
PMN-MDSC
M-MDSC (A)
Ifng
0.057
Nos2
0.04
Arg-1
0.5700
Mmp9
0.07
CD206
0.06
Ym-1
0.21
Relative expression
Control
CNP-301

(B)

TREATMENT OF IMMUNE EVASIVE TUMORS

CROSS-REFERENCE TO RELATED APPLICATIONS

This application is a national phase filing under 35 U.S.C. § 371 of International PCT Application No. PCT/US2020/044622, filed Jul. 31, 2020, and claims the benefit of U.S. Provisional Application No. 63/018,026, filed Apr. 30, 2020, and U.S. Provisional Application No. 62/881,326, filed Jul. 31, 2019, the contents of each of which are hereby incorporated by reference in their entirety for all purposes.

FIELD OF THE DISCLOSURE

The present disclosure relates, in general, to methods of treating tumors using surface-functionalized particles, alone or in combination with anti-cancer therapeutics.

BACKGROUND

Studies over the past decade have unequivocally confirmed the long-standing hypothesis that the immune system is capable of mounting efficient anti-tumor responses (1-3). Successful immune-mediated clearance of tumor cells depends on the collective activity of a number of immune-cell types such as antigen presenting cells (APCs) (e.g., macrophages and dendritic cells), other myeloid cells (e.g., monocytes and neutrophils) and effector cells (e.g., B-cells, T-cells, NKT-cells, and NK cells) (3-9). However, tumor cells are capable of evolving mechanisms that result in evasion of the immune system. One primary mechanism that promotes tumor immune evasion is the expression of proteins and soluble factors (e.g., PD-L1, CD47, and TGF-β) that repress anti-tumor immune function (10-12). These findings led to the development of immunotherapies that aim to modulate the immune system to enable sustained anti-tumor immune function. While many immunotherapeutics have been successfully developed for clinical applications and transformed cancer treatment, only a subset of patients responds to immunotherapy and many of those that do respond develop resistance to the therapy. For example, only 20-30% patients respond to checkpoint inhibitor (anti-PD1/L1) therapy. Understanding the mechanisms underlying low response rates to immunotherapies have led to the identification of cellular and molecular determinants that influence therapeutic success. Important among these determinants are the immunologic status of the tumor, immune cell infiltrate, and tumor mutational burden (13-15).

The immunologic status of a tumor can be characterized broadly based on the degree of immune cell (e.g., $CD4^+$ T-cells, $CD8^+$ T-cells, $NK1.1^+$ NK cells, APCs, monocytes, and neutrophils) infiltration into the tumor, immune cell phenotype (e.g., $PD\text{-}1^+$, $PD\text{-}L1^+$, and $PD\text{-}L2^+$), and normal immune cell function (e.g., expression of IFN-γ, IL-12, IL-15, and MHCII). Tumors that exhibit higher degrees of immune cell infiltrate are referred to as immunologically 'hot' tumors. As immunotherapies rely on the presence of immune cells in the TME, immunologically 'hot' tumors typically respond well to immunotherapies and are associated with a favorable outcome. In contrast, tumors that exhibit low levels immune infiltrate, referred to as immunologically 'cold' (or immune evasive, immunologically protected, microsatellite stable, microsatellite instability low, comprising a low immune infiltrate, comprising a low tumor mutational burden and/or exhibiting heterogeneity), respond poorly to immunotherapies (16,17). Also relevant in determining the immunologic status of tumors is the balance between pro-inflammatory and anti-inflammatory mediators in the tumor microenvironment (TME). For example, increased presence of anti-inflammatory cells such as myeloid-derived suppressor cells (MDSCs) ($CD11b^+Ly6C^{HI}$ or $CD11b^+Ly6G^+$), M2 tumor-associated macrophages (TAMs) ($CD11b^+F4/80^+CD206^+MHCII^{LO}$), and $MARCO^+$TAMs in the TME results in immunosuppression in the TME and repression of anti-tumor immune function, and is associated with resistance to therapy and unfavorable disease outcomes (18-22).

Tumor mutational burden (TMB) is an important tumor-intrinsic genetic factor that influences therapeutic response to immunotherapy. TMB is defined as the total number of mutations per coding base-pair in the tumor genome. Tumors carrying a high mutational burden are considered to be highly immunogenic. The presence of frequent genetic mutations give rise to tumor neoantigens that can be recognized by the immune system that results in the activation of a cascade of events that culminates with the induction of an antigen-specific anti-tumor response. Consistent with this hypothesis, studies have shown that a high TMB is correlated with a higher response rate to immunotherapies compared to a low TMB (14,15,23,24). Thus, the determination of the TMB status of a tumor can be beneficial during the diagnosis and treatment of cancers. Current clinical practice relies on microsatellite instability (MSI) testing to gain insights into the TMB status of a tumor (25). MSI is a condition of genetic hypermutability resulting from deficiency in the DNA mismatch repair system. High MSI causes tumors to accumulate a high mutational burden and become highly immunogenic. Such tumors are referred to as MSI-high (MSI-h) tumors. Accordingly, MSI-h tumors are more likely to respond to immunotherapy with several approved specifically for the treatment of MSI-h tumors. In contrast, mismatch repair proficient microsatellite stable (MSS) tumors have been found to be poor responders to immunotherapy (12,26,27).

Some of the most commonly diagnosed cancers (e.g., bladder, colorectal, ovarian, and pancreatic cancer) are also some of the most difficult to treat. A large majority of patients diagnosed with cancer harbor tumors that respond poorly to first-line (e.g., radiation and/or combination chemotherapy) and second-line (e.g., anti-PD-1/L1) treatment or are unresponsive altogether. Common features of such tumors are that they are immunologically 'cold', immunologically protected, contain anti-inflammatory and immune suppressive mediators in the TME, harbor a low TMB, or are microsatellite stable (MSS)/MSI-low. Tumor heterogeneity further complicates treatment as therapeutically unresponsive tumors are often composed of heterogeneous populations of tumor cells that exhibit varying degrees of factors (e.g., immune infiltrate, TMB, and MSI) that play a role in determining response to therapy (28,29).

SUMMARY

It is demonstrated herein that surface-functionalized nanoparticles (SFPs) are efficacious against tumors that are immunologically 'cold', immune evasive, immunologically protected, immunologically 'cold', microsatellite stable ("MSS"), microsatellite instability low ("MSI"), have a low immune infiltrate, have a low tumor mutational burden and/or exhibit heterogeneity. For example, without limitation, such tumors may harbor a low TMB, are MSS/MSI-low, and/or exhibit cellular and molecular factors in the TME that are anti-inflammatory or immune suppressive. SFPs can inhibit tumor growth and induce tumor cell death. SFPs, administered alone or in combination with other cancer therapeutics, can be used as an effective treatment option for a wide variety of cancers. In fact, as described herein, the SFPs are not limited to cancer type, and can be used to treat any cancer that may be characterized as immunologically 'cold', immune evasive, immunologically protected, immunologically 'cold', microsatellite stable, microsatellite instability low, have a low immune infiltrate, have a low tumor mutational burden and/or exhibit heterogeneity, or combinations thereof.

In various embodiments, the disclosure provides a method of treating cancer in a subject comprising administering to the subject surface functionalized particles alone or in combination with a cancer therapeutic, wherein the subject has one or more tumors that are characterized as immune evasive, immunologically protected, immunologically 'cold', microsatellite stable, microsatellite instability low, comprising a low immune infiltrate, comprising a low tumor mutational burden and/or exhibiting heterogeneity.

In various embodiments, the surface functionalized particle is a negatively charged particle free from attached peptide or antigenic moieties or other bioactive agents.

In various embodiments, the disclosure provides a method of treating cancer in subject comprising administering to the subject a surface functionalized particle alone or in combination with a cancer therapeutic, wherein the subject has one or more tumors with a low immune infiltrate. In various embodiments, the administering to a subject with one or more tumors with a low immune infiltrate alters the tumor immune infiltrate. In various embodiments, the tumor immune infiltrate comprises antigen-presenting cells, myeloid cells, and lymphoid cell. In various embodiments, antigen-presenting cells in the tumor immune infiltrate comprise macrophages and/or dendritic cells. In various embodiments, myeloid cells in the tumor immune infiltrate comprise monocytes, neutrophils, myeloid-derived suppressor cells (MDSCs), and tumor-associated macrophages (TAMs). In various embodiments, the TAMs in the tumor immune infiltrate comprise M1 macrophages, M2 macrophages, and $MARCO^+$ macrophages. In various embodiments, lymphoid cells in the tumor immune infiltrate comprise T-cells, B-cells, NK T-cells, and NK cells.

In various embodiments, the disclosure provides a method of treating cancer in a subject comprising administering to the subject surface functionalized particles alone or in combination with a cancer therapeutic, wherein the subject has one or more immune evasive tumors. In various embodiments, the subject has one or more immunologically protected tumors. In various embodiments, the subject has one or more microsatellite stable tumors. In various embodiments, the subject has one or more microsatellite low tumors. In various embodiments, the subject has one or more tumors with moderate microsatellite instability. In various embodiments, the subject has one or more tumors with a low tumor mutational burden. In various embodiments, the subject has one or more tumors with a moderate tumor mutational burden. In various embodiments, the subject has one or more tumors resistant to therapy. In various embodiments, the subject has one or more immunologically heterogeneous tumors. In various embodiments, the subject has genetically heterogeneous tumors. In various embodiments, the subject has one or more refractory tumors. In one or more embodiments, the subject has a tumor that develops resistance therapy during the course of treatment.

In various embodiments, the disclosure provides a method of treating cancer in a subject comprising administering to the subject surface functionalized particles alone or in combination with a cancer therapeutic, wherein the subject has one or more immune evasive tumors. In various embodiments, the administering alters the tumor immune infiltrate. In various embodiments, the administering alters the anti-tumor immune response. In various embodiments, the administering alters the tumor microenvironment comprising tumor cells, immune cells, cancer stem cells, and stroma. In various embodiments, the administering transforms an immunologically cold tumor into an immunologically hot tumor. In various embodiments, the administering reduces tumor size and/or inhibits tumor growth. In various embodiments, the administering induces tumor cell death, apoptosis, and/or necrosis via direct particle uptake by tumor cells.

In various embodiments, the disclosure provides a method of treating cancer in a subject comprising administering to the subject surface functionalized particles alone or in combination with a cancer therapeutic, wherein the subject has one or more tumors that are characterized as immunologically protected and/or immune evasive. In various embodiments, the administering alters the tumor-associated stroma comprising fibroblasts, cancer-associated fibroblasts, adipocytes, pericytes, endothelium, vasculature, lymphatic vessels, tumor-associated vasculature, mesenchymal stromal cells, mesenchymal stem cells, and extracellular matrix.

In various embodiments, the surface functionalized particles are polyglycolic acid (PGA), particles, polylactic acid (PLA) particles, poly (lactic-co-glycolic acid) (PLGA) particles, polystyrene particles, diamond particles, or iron, zinc, cadmium, gold, or silver particles, or combinations thereof.

In some embodiments, the surface functionalized particles are poly(lactic-co-glycolic acid) (PLGA) particles. In various embodiments, the particle comprises about 50:50, about 80:20 to about 100:0 polylactic acid:polyglycolic acid or from about 50:50, about 80:20 to about 100:0 polyglycolic acid:polylactic acid. In various embodiments, the particle comprises 50:50 polylactic acid:polyglycolic acid. In various embodiments, the particle comprises polylactic acid: polyglycolic acid from about 99:1 to about 1:99, e.g., about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, about 5:95, and about 1:99, including all values and ranges that lie in between these values.

In various embodiments, surface functionalization is achieved by carboxylation. Carboxylation can produce a negative charge on an otherwise neutral particle, or it can increase the negative charge of negatively charged particle. Without being bound by theory, carboxylation produces negatively charged surface, and this negative charge elicits therapeutic response in immune-evasive tumors. In some embodiments, the surface functionalized particles do not comprise a therapeutic agent, such as an embedded or attached cancer therapeutic. In further embodiments, surface functionalized is achieved by the addition of targeting agents. In some embodiments, the targeting agent comprises polypeptides, antibodies, carbohydrates, nucleic acids, lipids, small molecules, and surfactants. In various embodiments, surface functionalized nanoparticles are targeted preferentially to monocytes, neutrophils, macrophages, T-cells, B-cells, NK cells, NK T-cells, fibroblasts, cancer associated fibroblasts, endothelial cells, adipocytes, pericytes, endothelium, vasculature, lymphatic vessels, tumor-associated vasculature, mesenchymal stromal cells, mesenchymal stem cells, and/or extracellular matrix.

In various embodiments, the particles have a zeta potential between −100 mV and −1 mV. In various embodiments, the particles have a zeta potential between −80 mV and −30 mV. In some embodiments, the zeta potential of the particle is from about −100 mV to about −40 mV, from about −75 mV to about −40 mV, from about −70 mV to about −30 mV, from about −60 mV to about −35 mV, or from about −50 mV to about −40 mV. In various embodiments, the zeta potential is about −30 mV, −35 mV, −40 mV, −45 mV, −50 mV, −55 mV, −60 mV, −65 mV, −70 mV, −75 mV, −80 mV, −85 mV, −90 mV, −95 mV or −100 mV, including all values and ranges that lie in between these values.

In various embodiments, the diameter of the negatively charged particle is between 0.1 μm to 10 μm. In various embodiments, the particle has an average diameter of between about 0.2 μm and about 2 μm; between about 0.3 μm to about 5 μm; between about 0.5 μm to about 3 μm; or between about 0.5 μm to about 1 μm. In some embodiments, the particle has a diameter of about 100 to 1500 nm, about 200 and 2000 nm, about 100 to 1000 nm, about 300 to 1000 nm, about 400 to 800 nm, or about 200 to 700 nm. In various embodiments, the particle has an average diameter of about 100 nm, 200 nm, 300 nm, 400 nm, 500 nm, 600 nm, 700 nm, 800 nm, 900 nm, 1000 nm, 1100 nm, 1200 nm, 1300 nm, 1400 nm, 1500 nm, or 2000 nm, including all values and ranges that lie in between these values. In some embodiments, the diameter of the negatively charged particle is between 400 nm to 800 nm.

In various embodiments, the particle is a PLGA particle having a zeta potential between −80 to −30 mV and a diameter between 200 and 2000 nm, optionally surface functionalized by carboxylation.

In various embodiments, the disclosure provides a method of treating cancer in a subject comprising administering to the subject a composition comprising negatively charged PLGA particles alone or in combination with a cancer therapeutic, wherein said particle does not comprise peptides, antigenic moieties or other bioactive agents has a diameter between 400 nm and 800 nm and a zeta potential between −1 mV and −100 mV, and wherein the subject has one or more immune evasive tumors.

In various embodiments, the subject has a cancer selected from the group consisting of brain cancer, skin cancer, eye cancer, breast cancer, prostate cancer, lung cancer, esophageal cancer, head and neck cancer, cervical cancer, liver cancer, colon cancer, bone cancer, uterine cancer, ovarian cancer, bladder cancer, stomach cancer, oral cancer, thyroid cancer, kidney cancer, testicular cancer, leukemia, lymphoma and mesothelioma. Additional cancers contemplated by the methods are disclosed in the Detailed Description.

In various embodiments, the cancer therapeutic is a chemotherapeutic selected from the group consisting of growth inhibitors, DNA-replication inhibitors, kinase inhibitors, signaling cascade inhibitors, angiogenesis inhibitors, metabolic inhibitors, amino acid synthesis inhibitors, selective inhibitors of oncogenic proteins, inhibitors of metastasis, inhibitors of anti-apoptosis factors, apoptosis inducers, nucleoside signaling inhibitors, enzyme inhibitors and DNA-damaging agents.

In various embodiments, the cancer therapeutic comprises one or more biologic agents selected from the group consisting of cytokines, angiogenesis inhibitors, immune checkpoint modulators, enzymes and monoclonal antibodies.

In various embodiments, cytokines are selected from the group consisting of transforming growth factors, tumor necrosis factor, interferons and interleukins. Exemplary cytokines include, but are not limited to, IFN-alpha, IFN-beta, IFN-gamma, IL-1, IL-2, IL-4, IL-5, IL-6, IL-7, IL-10, IL-11, IL-12, IL-13, IL-15, IL-17, IL-18, IL-21, members of the transforming growth factor beta superfamily, including TGF-β1, TGF-β2 and TGF-β3, tumor necrosis factor alpha, Granulocyte colony-stimulating factor (G-CSF), and Granulocyte macrophage colony-stimulating factor (GM-CSF).

In various embodiments, the cancer therapeutic comprises an enzyme. In various embodiments, the cancer therapeutic comprises an enzyme that targets T-cells, B-cells, APCs, monocytes, MDSCs, TAMs, neutrophils, other monocyte-derived cells, tumor-associated stroma, cancer stem cells, mesenchymal stem cells, extracellular matrix, and amino acids. In various embodiments, the cancer therapeutic comprises an enzyme selected from the group comprising asparaginase, kynurininase, L-arginine deiminase, L-methionine-γ-lyase, one or more amino acid degrading enzymes, and one or more nucleoside degrading enzymes.

In various embodiments the monoclonal antibodies are mono-specific, bi-specific, tri-specific or bispecific T-cell engaging (BiTE) antibodies.

In various embodiments the monoclonal antibodies are immune cell co-stimulatory molecule agonists that induce an anti-tumor immune response. Exemplary co-stimulatory molecules include, but are not limited to, ICOS (Inducible T cell Co-stimulator) (CD278), OX40 (CD134), GITR (Glucocorticoid-induced Tumor Necrosis Factor Receptor), CD40 and CD27.

In various embodiments, monoclonal antibodies are selected from the group comprising Alemtuzumab, Bevacizumab, Brentuximab, Cetuximab, Denosumab, Ibritumomab, Trastuzumab, Panitumumab, Pertuzumab, and Rituximab. In various embodiments, monoclonal antibodies target receptor tyrosine kinase, EGFR, VEGF, VEGFR, PDGF, PDGFR, TGF-β, TGF-β-LAP, SIRP-α, CD47, CD39, CD73, and fibroblast activation protein (FAP).

In various embodiments, the immune checkpoint modulators target Programmed cell death protein 1 (PD1), Programmed cell death protein ligand-1 (PD-L1), cytotoxic T-lymphocyte-associated protein 4 (CTLA-4), T-cell Immunoglobulin and mucin-domain containing-3 (TIM-3), Lymphocyte-activation Gene 3 (LAG-3) and/or TIGIT (T cell immunoreceptor with Ig and ITIM domains). In various embodiments, the immune checkpoint modulator is an antibody selected from the group consisting of ipilimumab, tremelimumab, pembrolizumab, nivolumab, atezolizumab, avelumab, cemiplimab and durvalumab.

In various embodiments, the cancer therapeutic comprises one or more cell-based therapies selected from the group consisting of adoptive cell transfer, tumor-infiltrating leukocyte therapy, chimeric antigen receptor T-cell therapy (CAR-T), NK-cell therapy and stem cell therapy.

In various embodiments the cell-based therapy is the adoptive transfer of autologous patient-derived cells. In various embodiments the cell-based therapy is the adoptive transfer of allogenic donor-derived cells.

In various embodiments, the cell-based therapy is the transfer of universal donor-derived or induced pluripotent stem cell-derived cells that are not patient specific and amenable to long-term storage. Such therapies are also referred to as 'off-the-shelf' therapies.

In various embodiments, the cancer therapeutic is a hormone therapy. In various embodiments, the cancer therapeutic comprises one or more antibody-drug conjugates. In various embodiments, the cancer therapeutic comprises one or more cancer vaccines. In various embodiments, the cancer vaccine is a protein, polypeptide, and/or nucleic acid vaccine.

In various embodiments, the cancer therapeutic is an immunotherapy selected from the group comprising oncolytic virus, bacteria, oncolytic bacteria or other bacterial consortia, tumor cell lysate, bacterial cell lysate, lipopolysaccharide (LPS), *Bacillus* Calmette-Guerin (BCG), a microbiome modulator, and/or a toll-like receptor (TLR) agonist. In various embodiments, the TLR agonist is a TLR3, TLR4, TLR5, TLR7, TLR8, TLR9, TLR10, TLR11, TLR12, and/or TLR13 agonist. In various embodiments, the TLR agonist is derived from virus, bacteria and/or made synthetically. In various embodiments, the immunotherapy is a STING pathway modulator.

In various embodiments, the cancer therapeutic comprises a viral or a bacterial vector. In various embodiments, the viral vector is selected from the group comprising adenovirus, adeno-associated virus (AAV), herpes simplex virus, lentivirus, retrovirus, alphavirus, flavivirus, rhabdovirus, measles virus, Newcastle disease virus, poxvirus, vaccinia virus, modified Ankara virus, vesicular stomatitis virus, picornavirus, tobacco mosaic virus, potato virus x, comovirus, or cucumber mosaic virus. In various embodiments, the virus is an oncolytic virus. In various embodiments the virus is a chimeric virus, a synthetic virus, a mosaic virus or a pseudotyped virus.

Additional cancer therapeutics contemplated for use in the methods are set out in the Detailed Description.

In various embodiments, the surface functionalized particle and/or the cancer therapeutic is administered once daily, twice daily, three times per day, seven times per week, six times per week, five times per week, four times per week, three times per week, twice weekly, once weekly, once every two weeks, once every three weeks, once every 4 weeks, once every two months, once every three months, once every 6 months or once per year. In various embodiments, the surface functionalized particle and/or the cancer therapeutic is administered for 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, or 52 weeks, or more.

In various embodiments, the particle and/or the cancer therapeutic is administered intravenously, orally, nasally, intramuscularly, ocularly, transdermally, or subcutaneously.

In various embodiments, the subject is a mammal. In various embodiments, the subject is human.

In various embodiments, the administration improves one or more symptoms of the cancer or proliferative disorder. In various embodiments, the one or more symptoms are selected from the group consisting of tumor size or tumor burden in the subject, tumor metastasis, and levels of inflammatory cells in the tumor. In various embodiments, the administration reduces the tumor size or tumor burden by about 10%, 20%, 30% or more. In various embodiments, the administration reduces the tumor size or tumor burden by about 10%, about 20%, about 30%, about 40%, about 50%, about 60%, about 70%, about 80%, about 90% or about 100%, including all values and ranges in between these values.

In various embodiments, the particle is formulated in a composition comprising a pharmaceutical acceptable carrier, diluent or excipient. In various embodiments, the cancer therapeutic is formulated in a composition comprising a pharmaceutical acceptable carrier, diluent or excipient. In various embodiments, the particle and cancer therapeutic can be formulated in the same composition or in separate compositions.

Also contemplated is a composition comprising any of the foregoing surface functionalized particles or cancer therapeutic compositions of the disclosure, or use thereof in preparation of a medicament, for treatment of any of the disorders described herein associated with inflammation and cancer and/or proliferative diseases.

It is understood that each feature or embodiment, or combination, described herein is a non-limiting, illustrative example of any of the aspects of the invention and, as such, is meant to be combinable with any other feature or embodiment, or combination, described herein. For example, where features are described with language such as "various embodiments", "one embodiment", "some embodiments", "certain embodiments", "further embodiment", "specific exemplary embodiments", and/or "another embodiment", each of these types of embodiments is a non-limiting example of a feature that is intended to be combined with any other feature, or combination of features, described herein without having to list every possible combination. Such features or combinations of features apply to any of the aspects of the disclosure. Where examples of values falling within ranges are disclosed, any of these examples are contemplated as possible endpoints of a range, any and all numeric values between such endpoints are contemplated, and any and all combinations of upper and lower endpoints are envisioned.

BRIEF DESCRIPTION OF THE DRAWINGS

(FIG. 1A) Effect of indicated treatments on cell viability in the tumor (n=5). (FIG. 1B) Effect of indicated treatments on B16F10 tumor growth. Treatments were initiated after palpable tumor formation (Day 0) (n=10). (FIG. 1C) Effect of indicated treatments, administered after palpable tumor formation (Day 0), on the survival of B16F10 tumor-bearing mice (n=10). (FIG. 1D-1F) Effects of indicated treatment on the frequencies of MDSCs (FIG. 1D), TAMs (FIG. 1E) and NK cells (FIG. 1F) in the tumors (n=5). One-way ANOVA tests were performed to determine statistical significance (n.s=P>0.5; *=p≤1.05; =p≤1.01; **=p≤1.0001)

(FIG. 2A) Tumor volumes were measured throughout the course of the experiment and the growth curves are shown for each treatment group. (FIG. 2B) Shown are average tumor sizes on Day 21 after tumor inoculation in groups treated with Saline, anti-PD1, or CNP-301. CNP-301 treatment was initiated at different timepoints after tumor inoculation (on Days 1, 2, 4, or 5). Day 21 average tumor sizes were significantly different between Saline group and both Day 1 and Day 2 CNP-301 treatment groups (p=0.006 and p=0.0295, respectively). Average tumor size of the Anti-PD1 group were also greater than that of Day 1 CNP-301 treatment group (p=0.0194). Tumor sizes were compared using one-way ANOVA with Tukey's multiple comparisons test. N=7-8 per group.

FIG. 3A-3B shows that treatment with surface functionalized particles inhibits metastases to the lungs. (FIG. 3A) Bioluminescence imaging of metastatic lesions in the lung using IVIS® show that CNP-301 inhibits tumor metastasis and growth of metastatic lesions. Shown are images acquired during the evaluation of metastatic lesions in lungs of animals treated with Saline, anti-PD1, or CNP-301. CNP-301 treatment was initiated at different timepoints after tumor inoculation (on Days 1, 2, 4, or 5). (FIG. 3B) Total flux from images in FIG. 3A is quantified and shown in FIG. 3B with the dotted red line indicating the approximate flux cutoff for detectable metastasis. N=7-8 per group.

FIGS. 4A-4B shows that treatment with surface functionalized particles, CNP-301, inhibits pre-existing metastases. (FIG. 4A) 4T1 primary tumors were inoculated into the mammary fat pad and allowed to growth until Day 11. (FIG. 4B) On Day 11, the primary tumor was surgically resected and treatment with Saline or CNP-301 (1 mg/mouse) was initiated. Lung metastases were evaluated on Day 42 by assaying bioluminescence signaling using IVIS®. N=9-10 per group.

(FIG. 5A, MIP-1(3; FIG. 5B, TNFα; FIG. 5C RANTES (CCL5); FIG. 5D, IFNγ; and FIG. 5E, MCP-1).

FIG. 8B, TNFα; FIG. 8C RANTES (CCL5); FIG. 8D, IFNγ; and FIG. 8E, MCP-1). Cytokines/chemokines were assayed from blood by ELISA. Statistical significance was determined by 2-way ANOVA with Bonferroni's multiple comparison test. N=5 per group.

(FIG. 13A) Three days after tumor inoculation, mice were administered a single dose of Saline or CNP-301. 12 hours post-treatment, blood was collected from mice and the frequencies of ($CD11b^+/F4/80^+$), monocytes ($CD11b^+Ly6C^+$), MDSCs ($CD11b^+/Ly6C^{lo/-}/Ly6G^+$), and dendritic cells ($CD11c^+$) were evaluated by flow cytometry. (n=4). (FIG. 13B) Three days after tumor inoculation, mice were administered Saline or CNP-301 on six consecutive days. On Day 10 after tumor inoculation, lungs were harvested and the frequencies of ($CD11b^+/F4/80^+$), monocytes ($CD11b^+Ly6C^+$), MDSCs ($CD11b^+/Ly6C^{lo/-}/Ly6G^+$), and dendritic cells ($CD11c^+$) were evaluated by flow cytometry. (n=4). A 2-way ANOVA with Tukey's multiple comparisons test was performed. Statistical significance was defined as * p<0.001 and ** p<0.0001.

(FIG. 14A) Flow cytometry plots showing the frequency CNP-301-positive (APC-CNP-301) TAMs ($CD11b^+$ $F4/80^+$), M-MDSCs ($CD11b^+Ly6C^+Ly6G^-$), PMN-MDSCs ($CD11b^+Ly6C^-Ly6G^+$), and fibroblasts ($CD45^-CD140a^+$) in LLC tumors. (FIG. 14B) Frequency of CNP-301 positive (APC-CNP-301) TAMs ($CD11b^+F4/80^+$), M-MDSCs ($CD11b^+Ly6C^+Ly6G^-$), PMN-MDSCs ($CD11b^+Ly6C^-$ $Ly6G^+$), and fibroblasts ($CD45^-CD140a^+$) in LLC tumors. (FIG. 14C) Flow cytometry plots showing the frequency CNP-301-positive (APC-CNP-301) macrophages ($CD11b^+$ $F4/80^+$), M-MDSCs ($CD11b^+Ly6C^+Ly6G^-$), and PMN-MDSCs ($CD11b^+Ly6C^-Ly6G^+$) in spleen of LLC tumor-bearing mice. (FIG. 14D) Frequency of CNP-301 positive (APC-CNP-301) macrophages ($CD11b^+F4/80^+$), M-MDSCs ($CD11b^+Ly6C^+Ly6G^-$), and PMN-MDSCs ($CD11b^+Ly6C^-$ $Ly6G^+$) in spleens of LLC tumor-bearing mice.

(FIG. 15A) Expression of indicated genes evaluated by qPCR in TAMs ($CD11b^+F4/80^+$) isolated from LLC tumors. (FIG. 15B) Expression of indicated genes evaluated by qPCR in fibroblasts ($CD45^-CD140a^+$) isolated from LLC tumors.

DETAILED DESCRIPTION

Figures 1A, 1B, 1C, 1D, 1E, 1F:
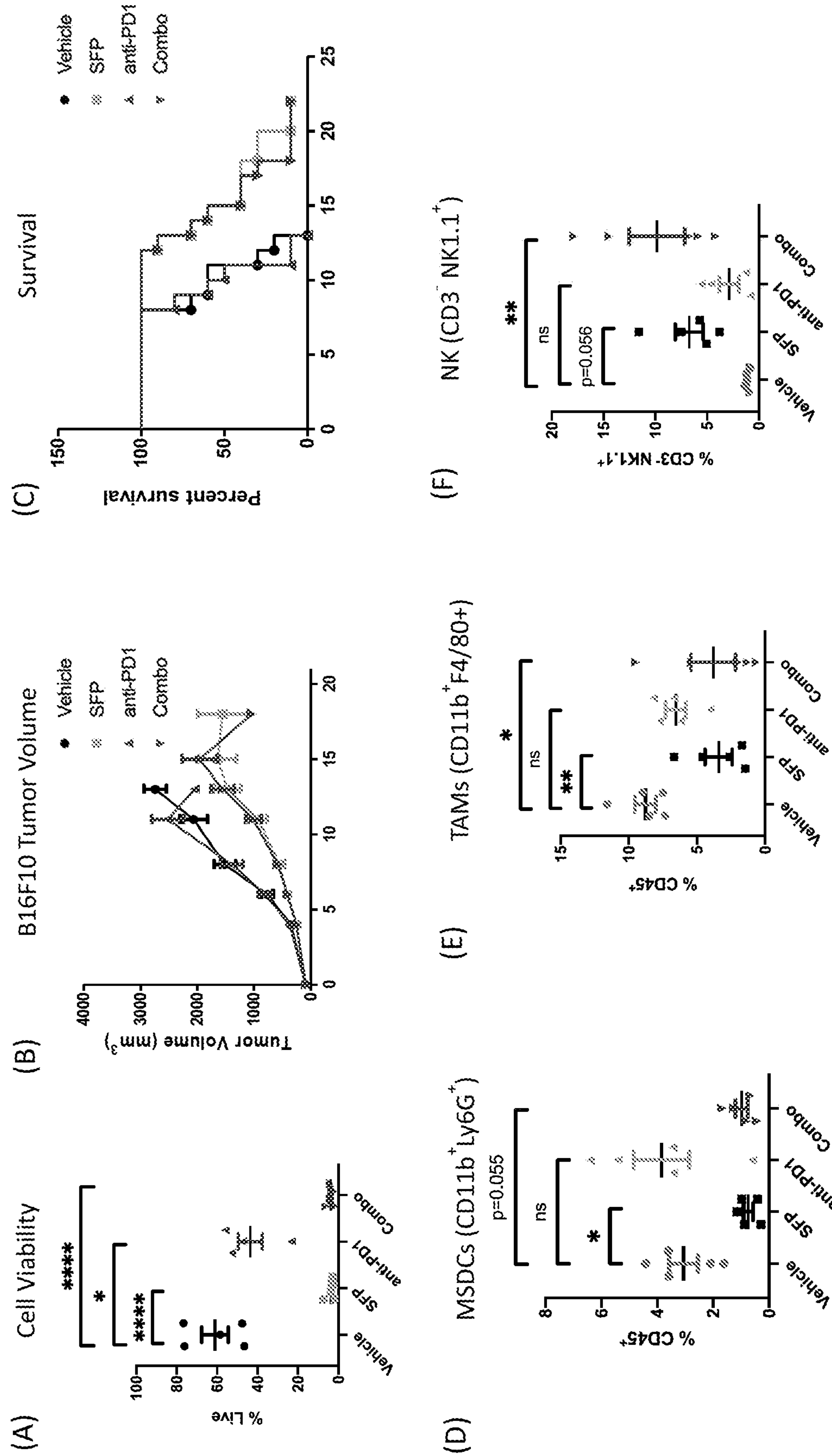
FIG. 1A-1F shows efficacy of SFP against immunologically "cold" tumors with low TMB.

The present disclosure demonstrates that surface functionalized particles as described herein are able to decrease tumor growth in vivo to a greater extent than classic immunotherapy by checkpoint inhibitors in tumors that are (i) immune evasive, (ii) immunologically "cold", (iii) immunologically protected, (iv) microsatellite stable, (iv) microsatellite instability low, (v) comprise a low immune infiltrate, (vi) comprise a low tumor mutational burden and/or (vii) exhibit heterogeneity. The ability of surface functionalized particles alone to have such an effect was surprising and unexpected, and supports the use of surface functionalized particles to treat subjects having cancer, in particular cancers which may be non-responsive or refractory to immunotherapeutics.

Definitions

Each publication, patent application, patent, and other reference cited herein is incorporated by reference in its entirety to the extent that it is not inconsistent with the present disclosure.

It is noted here that as used in this specification and the appended claims, the singular forms "a," "an," and "the" include plural reference unless the context clearly dictates otherwise.

"Particle" as used herein refers to any non-tissue derived composition of matter, it may be a sphere or sphere-like entity, bead, or liposome. The term "particle", the term "immune modifying particle", and the term "bead" may be used interchangeably depending on the context. Additionally, the term "particle" may be used to encompass beads and spheres.

"Surface-functionalized" as used herein refers to particles which have one or more functional groups on its surface. In some embodiments, the surface functionalization occurs by the introduction of one or more functional groups to a surface of a particle. "Surface functionalized particles" (SFP) refers to particles as described herein that comprise a functional group on the particle surface. In embodiments, surface functionalization may be achieved by carboxylation (i.e., addition of one or more carboxyl groups to the particle surface) or addition of other chemical groups (e.g., other chemical groups that impart a negative surface charge). Because the surface functional groups provide a site for ligand conjugation, surface functionalized particles may also include targeting agents such as polypeptides, antibodies, nucleic acids, lipids, small-molecules, carbohydrates, and surfactants. Methods of making surface functionalized nanoparticles are described in, for example, Froimowicz et al., Curr Org. Chem 17:900-912, 2013. In various embodiments, it is contemplated that surface functionalized particles include negatively charged particles that are free of therapeutic agents, e.g., free from attached peptide or antigenic moieties or other bioactive agents.

"Negatively charged particle" as used herein refers to particles which have been modified to possess a net surface charge that is less than zero. In embodiments, negatively charged particles are surface functionalized particles, in which a particle is carboxylated to thereby have a negative surface charge.

Zeta potential is the charge that develops at the interface between a solid surface and its liquid medium. "Negative zeta potential" refers to a particle having a zeta potential of the particle surface as represented in milliVolts (mV), and measured by an instrument known in the field to calculate zeta potential, e.g., a NanoBrook ZetaPlus zeta potential analyzer or Malvern Zetasizer.

"Carboxylated particles" or "carboxylated beads" or "carboxylated spheres" includes any particle that has been modified or surface functionalized to add one or more carboxyl group onto the particle surface. In some embodiments the addition of the carboxyl group enhances phagocyte/monocyte uptake of the particles from circulation, for instance through the interaction with scavenger receptors such as MARCO. Carboxylation of the particles can be achieved using any compound which adds carboxyl groups, including, but not limited to, Poly (ethylene-maleic anhydride) (PEMA). Carboxylation may also be achieved by using polymers with native carboxyl groups (e.g., PLGA) to form particles, in which the manufacturing process results in the carboxyl groups being located on the surface of the particle.

"Biodegradable" as used herein refers to a particle comprising a polymer that may undergo degradation, for example, by a result of functional groups reacting with the water in the solution. The term "degradation" as used herein refers to becoming soluble, either by reduction of molecular weight or by conversion of hydrophobic groups to hydrophilic groups. Biodegradable particles do not persist for long times in the body, and the time for complete degradation can be controlled. Biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties. Biodegradable materials suitable for the present invention include diamond, PLA, PGA, polypropylene sulfide, and PLGA polymers, as well as metals such as iron (Fe), zinc (Zn), cadmium (Cd), gold or silver. Biocompatible but non-biodegradable materials may also be used in the particles described herein. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

The term "tumor microenvironment" (TME) as used herein refers to cells, molecules, and blood vessels that surround and feed a tumor cell (National Cancer Institute Dictionary of Cancer Terms). The tumor microenvironment includes immune cells, such as bone-marrow derived inflammatory cells, myelo-monocytic cells, myeloid derived suppressor cells, tumor associated-macrophages, and lymphocytes, fibroblasts, signaling molecules and the extracellular matrix (ECM) (Joyce et al., Science 348:74-80, 2015).

The term "hot tumor" as used herein refers to tumors that exhibit higher degrees of immune cell infiltrate, e.g., in the TME or at the tumor site, and generally respond well to immunotherapies.

The term "cold tumor" as used herein encompasses tumors that exhibit low levels of immune infiltrate, respond poorly to immunotherapies, have a low tumor mutational burden and are microsatellite stable or are microsatellite instability low (with respect to DNA mismatch repair) and/or exhibit tumor heterogeneity. Cold tumors are also referred to as immune-evasive or immunologically protected. See e.g., references 9, 16, 17, 23 and 24 for further description of hot and cold tumor characterization.

The term "subject" as used herein refers to a human or non-human animal, including a mammal or a primate, that is administered a particle as described herein. Subjects can include animals such as dogs, cats, rats, mice, rabbits, horses, pigs, sheep, cattle, and humans and other primates.

The term "therapeutic agent" refers to a moiety that is able to ameliorate or lessen one or more symptoms or signs of the disease or disorder being treated when administered at a therapeutically effective amount. Non-limiting examples of therapeutic agents include other cancer therapeutics, including peptides, proteins, or small molecule therapeutic agents.

The term "therapeutically effective amount" is used herein to indicate the amount of target-specific composition of the disclosure that is effective to ameliorate or lessen one or more symptoms or signs of the disease or disorder being treated.

The terms "treat", "treated", "treating" and "treatment", as used with respect to methods herein refer to eliminating, reducing, suppressing or ameliorating, either temporarily or permanently, either partially or completely, one or more clinical symptom, manifestation or progression of an event, disease or condition. Such treating need not be absolute to be useful.

Surface Functionalized Particle

The present disclosure provides for uses of surface functionalized particles in the treatment methods described herein.

Surface functionalized particles can be formed from a wide range of materials. The particle is preferably composed of a material suitable for biological use (e.g., a pharmaceutically acceptable material). For example, particles may be composed of glass, silica, polyesters of hydroxy carboxylic acids, polyanhydrides of dicarboxylic acids, or copolymers of hydroxy carboxylic acids and dicarboxylic acids and biocompatible metals. In various embodiments, the particles may be composed of polyesters of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy hydroxy acids, or polyanhydrides of straight chain or branched, substituted or unsubstituted, saturated or unsaturated, linear or cross-linked, alkanyl, haloalkyl, thioalkyl, aminoalkyl, aryl, aralkyl, alkenyl, aralkenyl, heteroaryl, or alkoxy dicarboxylic acids. Additionally, particles can be quantum dots, or composed of quantum dots, such as quantum dot polystyrene particles (Joumaa et al. (2006) Langmuir 22: 1810-6). Particles including mixtures of ester and anhydride bonds (e.g., copolymers of glycolic and sebacic acid) may also be employed. For example, particles may comprise materials including polyglycolic acid polymers (PGA), polylactic acid polymers (PLA), polysebacic acid polymers (PSA), poly(lactic-co-glycolic) acid copolymers (PLGA or PLG; the terms are interchangeable), [rho] oly(lactic-co-sebacic) acid copolymers (PLSA), poly(glycolic-co-sebacic) acid copolymers (PGSA), polypropylene sulfide polymers, poly(caprolactone), chitosan, etc. Other biocompatible, biodegradable polymers useful in the present invention include polymers or copolymers of caprolactones, carbonates, amides, amino acids, orthoesters, acetals, cyanoacrylates and degradable urethanes, as well as copolymers of these with straight chain or branched, substituted or unsubstituted, alkanyl, haloalkyl, thioalkyl, aminoalkyl, alkenyl, or aromatic hydroxy- or di-carboxylic acids. In addition, the biologically important amino acids with reactive side chain groups, such as lysine, arginine, aspartic acid, glutamic acid, serine, threonine, tyrosine and cysteine, or their enantiomers, may be included in copolymers with any of the aforementioned materials to provide reactive groups for conjugating to antigen peptides and proteins or conjugating moieties.

In embodiments, the surface functional particle comprises one or more biodegradable polymers or materials. Biodegradable materials suitable for the present invention include diamond, PLA, PGA, polypropylene sulfide, and PLGA polymers, as well as metals such as iron (Fe), zinc (Zn), cadmium (Cd), gold (Au) or silver (Ag).

Biocompatible but non-biodegradable materials may also be used in the particles described herein. For example, non-biodegradable polymers of acrylates, ethylene-vinyl acetates, acyl substituted cellulose acetates, non-degradable urethanes, styrenes, vinyl chlorides, vinyl fluorides, vinyl imidazoles, chlorosulphonated olefins, ethylene oxide, vinyl alcohols, TEFLON® (DuPont, Wilmington, Del.), and nylons may be employed.

In various embodiments, the particle comprises polymers, copolymers, dendrimers, diamond nanoparticle, polystyrene nanoparticles or metals. It various embodiments, it is contemplated that the particle comprises polyglycolic acid polymers (PGA), polylactic acid (PLA), polystyrene, copolymers of PLG and PLA (poly(lactide-co-glycolide), PLGA), diamond, a liposome, PEG, cyclodextran, or metals, such as iron (Fe), zinc (Zn), cadmium (Cd), gold (Au) or silver (Ag), or combinations thereof.

The surface functionalized particles of the disclosure can be manufactured by any means known in the art. Exemplary methods of manufacturing particles include, but are not limited to, microemulsion polymerization, interfacial polymerization, precipitation polymerization, emulsion evaporation, emulsion diffusion, solvent displacement, and salting out (Astete and Sabliov, J. Biomater. Sci. Polymer Edn., 17:247-289(2006)). Methods of making surface functionalized particles contemplated herein are disclosed in U.S. Pat. No. 9,616,113 and International Patent Publication WO2017/143346. Manipulation of the manufacturing process for PLGA particles can control particle properties (e.g. size, size distribution, zeta potential, morphology, hydrophobicity/hydrophilicity, polypeptide entrapment, etc). The size of the surface functionalized particle is influenced by a number of factors including, but not limited to, the concentration of polymer, e.g., PLGA, the solvent used in the manufacture of the particle, the nature of the organic phase, the surfactants used in manufacturing, the viscosity of the continuous and discontinuous phase, the nature of the solvent used, the temperature of the water used, sonication, evaporation rate, additives, shear stress, sterilization, and the nature of any encapsulated antigen or polypeptide.

In various embodiments, the surface functionalized particle is a co-polymer having a molar ratio from about 50:50 or about 80:20 to about 99:1 polylactic acid:polyglycolic acid or from about 50:50 or about 80:20 to about 99:1 polyglycolic acid:polylactic acid. In some embodiments, the surface functionalized particle is a poly(lactic-co-glycolic acid) particle. In various embodiments, the surface functionalized particle comprises 50:50 polylactic acid:polyglycolic acid. In various embodiments, the surface functionalized particle comprises polylactic acid:polyglycolic acid from about 99:1 to about 1:99, e.g., about 99:1, about 95:5, about 90:10, about 85:15, about 80:20, about 75:25, about 70:30, about 65:35, about 60:40, about 55:45, about 50:50, about 45:55, about 40:60, about 35:65, about 30:70, about 25:75, about 20:80, about 15:85, about 10:90, about 5:95, and about 1:99, including all values and ranges that lie in between these values.

In some embodiments, the zeta potential of the surface functionalized particle is from about −100 mV to about −1 mV. In some embodiments, the zeta potential of the surface functionalized particle is from about −100 mV to about −40 mV, from about −80 mV to about −30 mV, from about −75 mV to about −40 mV, from about −70 mV to about −30 mV, from about −60 mV to about −35 mV, or from about −50 mV to about −40 mV. In various embodiments, the zeta potential is about −30 mV, −35 mV, −40 mV, −45 mV, −50 mV, −55 mV, −60 mV, −65 mV, −70 mV, −75 mV −80 mV, −85 mV, −90 mV, −95 mV or −100 mV, including all values and subranges that lie between these values.

In some embodiments, the surface functionalized particle has an average diameter of between about 0.1 μm to about 10 μm. In some embodiments, the surface functionalized particle has an average diameter of between 0.2 μm and about 2 μm. In some embodiments, the surface functionalized particle has a diameter of between about 0.3 μm to about 5 μm. In some embodiments, the surface functionalized particle has a diameter of between about 0.5 μm to about 3 μm. In some embodiments, the surface functionalized particle has a diameter of between about 0.5 μm to about 1 μm. In some embodiments, the surface functionalized particle has a diameter of about 100 to 1500 nm, about 200 and 2000 nm, about 100 to 10000 nm, about 300 to 1000 nm, about 400 to 800 nm or about 200 to 700 nm, including all values and subranges that lie between these values.

To administer surface functionalized particles as described herein to human or other mammals, the particle may be formulated in a sterile composition comprising one or more sterile pharmaceutically acceptable carriers. The phrase “pharmaceutically or pharmacologically acceptable” refer to molecular entities and compositions that do not produce allergic, or other adverse reactions when administered using routes well-known in the art, as described below. “Pharmaceutically acceptable carriers” include any and all clinically useful solvents, dispersion media, coatings, antibacterial and antifungal agents, isotonic and absorption delaying agents and the like.

Pharmaceutical compositions of the present disclosure containing a surface functionalized particle herein may contain sterile pharmaceutically acceptable carriers or additives depending on the route of administration. Examples of such carriers or additives include water, a pharmaceutical acceptable organic solvent, collagen, polyvinyl alcohol, polyvinylpyrrolidone, a carboxyvinyl polymer, carboxymethylcellulose sodium, polyacrylic sodium, sodium alginate, water-soluble dextran, carboxymethyl starch sodium, pectin, methyl cellulose, ethyl cellulose, xanthan gum, gum Arabic, casein, gelatin, agar, diglycerin, glycerin, propylene glycol, polyethylene glycol, Vaseline, paraffin, stearyl alcohol, stearic acid, human serum albumin (HSA), mannitol, sorbitol, lactose, a pharmaceutically acceptable surfactant and the like. Additives used are chosen from, but not limited to, the above or combinations thereof, as appropriate, depending on the dosage form of the present invention. For solutions or emulsions, suitable carriers include, for example, aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. Intravenous vehicles can include various additives, preservatives, or fluid, nutrient or electrolyte replenishers. A variety of aqueous carriers are suitable, e.g., sterile phosphate buffered saline solutions, bacteriostatic water, water, buffered water, 0.4% saline, 0.3% glycine, and the like, and may include other proteins for enhanced stability, such as albumin, lipoprotein, globulin, etc., subjected to mild chemical modifications or the like.

It is contemplated that the surface functionalized particle may further comprise a surfactant. The surfactant can be anionic, cationic, or nonionic. Surfactants in the poloxamer and poloaxamines family are commonly used in particle synthesis. Surfactants that may be used, include, but are not limited to PEG, Tween-80, gelatin, dextran, pluronic L-63, PVA, methylcellulose, lecithin, DMAB and PEMA. Additionally, biodegradable and biocompatible surfactants including, but not limited to, vitamin E TPGS (D-α-tocopheryl polyethylene glycol 1000 succinate). In certain embodiments, two surfactants are used. For example, if the particle is produced by a double emulsion method, the two surfactants can include a hydrophobic surfactant for the first emulsion, and a hydrophobic surfactant for the second emulsion.

Therapeutic formulations of the surface functionalized particle are prepared for storage by mixing the particle having the desired degree of purity with optional physiologically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, succinate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; or metal complexes (e.g., Zn-protein complexes).

Preparations of particles can be stabilized by lyophilization. The addition of a cryoprotectant such as trehalose can decrease aggregation of the particles upon lyophilization. Any suitable lyophilization and reconstitution techniques can be employed. It will be appreciated by those skilled in the art that lyophilization and reconstitution can lead to varying degrees of antibody activity loss and that use levels may have to be adjusted to compensate.

Methods of Use

In one aspect, it is hypothesized herein that SFPs promote the transformation of immunologically cold tumors (immune-evasive) to immunologically hot tumors (immunogenic), which in turn will enable the treatment of immunologically protected, and often refractory, tumors. Additionally, SFPs can boost the efficacy of other cancer therapies when administered in combination to the subject. It is suggested herein that therapies using SFPs, alone or in combination with other cancer therapeutics, can alter the tumor immune infiltrate comprising of T-cells, B-cells, APCs, monocytes, MDSCs, TAMs, neutrophils, other monocyte-derived cells, tumor-associated stroma, cancer stem cells, and mesenchymal stem cells and result in an enhanced anti-tumor therapeutic effect.

Identification of Tumor Types

In various embodiments, the disclosure provides a method of treating cancer in a subject comprising administering to the subject surface functionalized particles alone or in combination with a cancer therapeutic, wherein the subject has one or more tumors that are characterized as immune evasive, immunologically protected, immunologically "cold", microsatellite stable, microsatellite instability low, comprising a low immune infiltrate, comprising a low tumor mutational burden and/or exhibiting heterogeneity.

In various embodiments, the disclosure provides a method for treating a tumors that are characterized as immune evasive, immunologically protected, immunologically "cold", microsatellite stable, microsatellite instability low, comprising a low immune infiltrate, comprising a low tumor mutational burden and/or exhibiting heterogeneity in a subject, comprising (i) diagnosing the subject has having an immune evasive tumor, immunologically protected tumor, immunologically "cold" tumor, microsatellite stable tumor, microsatellite instability low tumor, a tumor comprising a low immune infiltrate, a tumor comprising a low tumor mutational burden and/or a tumor exhibiting heterogeneity, and (ii) administering surface functionalized particles to the subject alone or in combination with a cancer therapeutic. In various embodiments, the diagnosing comprises assaying biomarkers/characteristics associated with tumors that are characterized as immune evasive, immunologically protected, immunologically "cold", microsatellite stable, microsatellite instability low, comprising a low immune infiltrate, comprising a low tumor mutational burden and/or exhibiting heterogeneity. In various embodiments, the method further comprises (iii) determining if the subject's tumor becomes immune responsive (e.g., immunogenic), and then (iv) administering an immunotherapy, optionally in combination with surface functionalized particles.

Also provided herein is a method for determining if a subject would be/is responsive to treatment with a surface functionalized particle as described herein alone or in combination with a cancer therapeutic, and treating the subject accordingly. In various embodiments, a patient diagnosed with cancer undergoes testing to identify the tumor as a cold tumor, e.g., using methods described herein and others described in the art. The disclosure provides a method for treating a subject having cancer, e.g., an immune evasive tumor, with a surface functionalized particle alone or in combination with a cancer therapeutic, the method comprising obtaining a tumor sample from a subject, conducting assays to determine if the tumor is a cold tumor, and treating the subject with a surface functionalized particle alone or in combination with a cancer therapeutic if the tumor is identified as a cold tumor. Assays to determine whether the tumor is a cold tumor include, but are not limited to tumor mutational burden analysis, microsatellite instability (MSI) testing, the degree of immune cell (e.g., $CD4^+$ T-cells, $CD8^+$ T-cells, $NK1.1^+$ NK cells, APCs, monocytes, and neutrophils) infiltration into the tumor, immune cell phenotype (e.g., PD-$1^+$, PD-$L1^+$, and PD-$L2^+$), immune cell function (e.g., expression of IFN-γ, IL-12, IL-15, and MHCII), and ratio of pro-inflammatory and anti-inflammatory mediators in the tumor microenvironment (TME).

Multiple diagnostic tools designed to characterize tumors at the cellular and molecular level are FDA-approved and commercially available. Examples of approved diagnostics include FOUNDATIONONE® CDX, FOUNDATIONONE® LIQUID, FOUNDATIONONE® HEME, BRACAnalysis CDx, therascreen EGFR RGQ PCR kit, cobase EGFR Mutation Test v2, PD-L1 IHC 22C3 pharmDx, Abbott Real Time IDH1, MRDx BCR-ABL test, VENTANA ALK (D5F3) CDx Assay, Abbott RealTime IDH2, Praxis Extended RAS Panel, Oncomine Dx Target Test, LeukoStrat CDx FLT3 Mutation Assay, FoundationFocus CDxBRCA Assay, Vysis CLL FISH Probe Kit, KIT D816V Mutation Detection, PDGFRB FISH, cobas KRAS Mutation Test, therascreen KRAS RGQ PCR Kit, FerriScan, Dako c-KIT pharmDx, INFORM Her-2/neu, PathVysion HER-2

DNA Probe Kit, SPOT-LIGHT HER2 CISH Kit, Bond Oracle HER2 IHC System, HER2 CISH pharmDx Kit, INFORM HER2 DUAL ISH DNA Probe Cocktail, HercepTest, HER2 FISH pharmDx Kit, THXID BRAF Kit, Vysis ALK Break Apart FISH Probe Kit, cobas 4800 BRAF V600 Mutation Test, VENTANA PD-L1 (SP142) Assay, therascreen FGFR RGQ RT-PCR Kit, and therascreen PIK3CA RGQ PCR Kit.

In various embodiments, the subject is screened for eligibly for treatment with one or more immunotherapies described herein. In various embodiments, subjects that are not eligible for treatment with such immunotherapies may be first treated with surface functionalized particles according to the methods described herein. Non-limiting examples of immunotherapies include Pembrolizumab (KEYTRUDA®, Merck Sharp & Dohme Corp), Nivolumab (OPDIVO®, Bristol-Myers Squibb), Atezolizumab (TECENTRIQ®), Avelumab (BAVENCIO®), and Durvalumab (IMFINZI®). Eligibility criteria for these immunotherapies are known in the art. For example, without limitation, pembrolizumab (KEYTRUDA®), nivolumab (OPDIVO®), and atezolizumab (TECENTRIQ®) have eligibility criteria based on PD-L1 expression levels. PD-L1 expression criteria and methods of measuring the same may be found at https://www.keytrudahcp.com/biomarker-testing/pd-I1-expression-testing/(pembrolizumab; KEYTRUDA®), or the FDA-approved prescribing information for pembrolizumab (KEYTRUDA®, as revised January 2020) atezolizumab (e.g., TECENTRIQ®, as revised May 2020) and nivolumab (e.g., OPDIVO®, as revised on June 2020). Each of these publications are herein incorporated by reference in its entirety for all purposes. As described herein, treating such patients with surface functionalized particles may promote the transformation of the tumor that is not eligible for treatment with an immunotherapy to an immunogenic tumor, which in turn will enable such tumors to be treated with an immunotherapy. In various embodiments, the tumors of subjects that are not eligible for an immunotherapy can be monitored throughout the course of treatment with a surface functionalized particle (e.g., as described herein based on PD-I1 expression levels) in order to determine when the tumor becomes eligible for treatment with an immunotherapy. Once the tumor is eligible for treatment with an immunotherapy, the subject may be administered an immunotherapy, alone or in combination with a surface functionalized particle.

In various embodiments, the disclosure provides a method of treating cancer in subject comprising administering to the subject a surface functionalized particle alone or in combination with a cancer therapeutic, wherein the subject has one or more tumors with a low immune infiltrate. In various embodiments, the administering to in subject with one or more tumors with a low immune infiltrate alters the tumor immune infiltrate. In various embodiments, the tumor immune infiltrate comprises antigen-presenting cells, myeloid cells, and lymphoid cell. In various embodiments, antigen-presenting cells in the tumor immune infiltrate comprise macrophages and/or dendritic cells. In various embodiments, myeloid cells in the tumor immune infiltrate comprise monocytes, neutrophils, myeloid-derived suppressor cells (MDSCs), and tumor-associated macrophages (TAMs). In various embodiments, the TAMs in the tumor immune infiltrate comprise M1 macrophages, M2 macrophages, and MARCO$^+$ macrophages. In various embodiments, lymphoid cells in the tumor immune infiltrate comprise T-cells, B-cells, NK T-cells, and NK cells.

Qualitative and quantitative methods have been described for the characterization of the tumor immune infiltrate, including but not limited, microscopic analyses, histological assays, cytological assays, flow cytometry, polymerase chain reaction (PCR), quantitative polymerase chain reaction (qPCR), RNA sequencing (RNA-seq), single-cell RNA sequencing (scRNA-seq), next-generation sequencing, whole-exome sequencing, epigenetic sequencing, ATAC-seq, microarray analysis, and mass cytometry or CyTOF. Biomarkers can be used, alone or in combination, for the evaluation of immune cells and include cell surface markers and secreted proteins. Exemplary biomarkers for the characterization of the tumor immune infiltrate include, but are not limited to, CD45, CD3, CD4, CD8, CD25, CD44, CD134, CD252, CD137, CD79, CD39, FOXP3, PD-1, LAG-3, TIM-1, IFN-γ, Granzyme, Perforin, CD11b, CD11c, Ly6C, Ly6G, CD14, CD16, CD80, MARCO, CD68, CD115, CD206, CD163, CD103c, F4/80, PD-L1, PD-L2, Arginase, iNOS, ROS, TNF-α, TGF-β, MHC-I, MHC-II, NK1.1, NKG2D, CD244, Ki67, CD19, CD20, CCR2, CXCR3, CCR4, CCR5, CCR6, CCR7, CCR10, CCL2, CCL5, Cx3CR1, CCL10, ICOS, CD40, CD40L, IL1α, IL1β, IL2, IL4, IL5, IL6, IL8, IL12, IL15, IL17, IL21, IL22, TCRγ/δ, TCRα/β, STAT3, ROR1c, and RORγt.

Cancer stem cells (CSCs) have been described as a subset of cells found within solid and hematologic tumors that are tumorigenic, and capable of self-renewal, differentiation. Several reports have described the importance of CSCs in the pathogenesis of a variety of tumors, tumor relapse after therapy, and development of therapeutic resistance. A number of cell surface markers can be used to distinguish CSCs within solid and hematologic tumors. CSC markers include, but are not limited to, CD19, CD20, CD24, CD34, CD38, CD44, CD90, CD133, Aldehyde dehydrogenase 1, CEACAM-6/CD66c, BMI-1, Connexin 43/GJA1, DLL4, EpCAM/TROP1, GLI-1, GLI-2, Integrins, PON1, PTEN, ALCAM/CD166, DPPIV/CD26, Lgr5, Musashi-1, A20, ABCG2, CD15, Fractalkine, HIF-2α, L1CAM, c-MAF, Nestin, Podoplanin, SOX2, CD96, CD117, FLT3, AFP, CD13, CD90, NF2/Merlin, ABCB5, NGFR, Syndecan-1, Endoglin, STRO-1, and PON1.

In various embodiments, the disclosure provides a method of treating cancer in a subject comprising administering to the subject surface functionalized particles alone or in combination with a cancer therapeutic, wherein the subject has one or more immune evasive tumors. In various embodiments, the subject has one or more immunologically protected tumors. In various embodiments, the subject has one or more microsatellite stable tumors. In various embodiments, the subject has one or more microsatellite low tumors. In various embodiments, the subject has one or more tumors with moderate microsatellite instability. In various embodiments, the subject has one or more tumors with a low tumor mutational burden. In various embodiments, the subject has one or more tumors with a moderate tumor mutational burden. In various embodiments, the subject has one or more tumors resistant to therapy. In various embodiments, the subject has one or more immunologically heterogeneous tumors. In various embodiments, the subject has genetically heterogeneous tumors. In various embodiments, the subject has one or more refractory tumors. In one or more embodiments, the subject has a tumor that develops resistance therapy during the course of treatment.

In various embodiments, the tumor characteristic is determined from one or more biological samples from a subject suffering from cancer. In various embodiments, the tumor characteristic is determined by comparing one or more biological samples from a subject suffering from cancer to one or more biological samples from one or more healthy subjects. In various embodiments, the tumor characteristic is determined from one or more biological samples selected from the group consisting of blood, cerebrospinal fluid, urine, stool, buccal swab, nasal swab, lavage, tissue biopsy, bone marrow biopsy, and tumor biopsy. In various embodiments, the tumor characteristic is determined from the analysis of cells, proteins, and/or nucleic acids in one or more biological samples from a subject suffering from cancer. In various embodiments, the tumor characteristic is determined by comparing the analysis of cells, proteins, and/or nucleic acids in one or more biological samples from a subject suffering cancer to the analysis of one or more biological samples from one or more healthy subjects. In various embodiments, the tumor characteristic is determined by comparing the analysis of cells, proteins, and/or nucleic acids in one or more biological samples from a subject suffering cancer to the analysis of one or more biological samples from one or more subjects suffering from cancer and responsive to treatment. In various embodiments, the cells are selected from the group consisting of leukocytes, epithelial cells, mesenchymal cells, mesenchymal stem cells, stromal cells, endothelial cells, fibroblasts, cancer-associated fibroblasts (CAFs), pericytes, adipocytes, cancer stem cells, circulating tumor cells (CTCs), hematopoietic stem cells, and hematopoietic progenitor cells. In various embodiments, the proteins are selected from the group consisting of cytokines, chemokines, growth factors, signal transduction proteins, enzymes, proteases, and nucleases. In various embodiments, the nucleic acids are selected from the group consisting of DNA, ssDNA, circulating tumor DNA (ctDNA), RNA, mRNA, dsRNA, siRNA, miRNA, and lncRNA. In various embodiments, the nucleic acid analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the tumor characteristic of a subject suffering from cancer is determined from the analysis of one or more blood samples collected from the subject. In various embodiments, the tumor characteristic of a subject suffering from cancer is determined from the analysis of cells, proteins, and/or nucleic acids in one or more blood samples collected from the subject. In various embodiments, the tumor characteristic of a subject suffering from cancer is determined by comparing the analysis of cells, proteins, and/or nucleic acids in one or more blood samples from the subject suffering from cancer to the analysis of one or more blood samples from one or more healthy subjects. In various embodiments, the cells analyzed in one or more blood samples are leukocytes, epithelial cells, mesenchymal cells, mesenchymal stem cells, stromal cells, endothelial cells, fibroblasts, cancer associated fibroblasts (CAFs), pericytes, adipocytes, cancer stem cells, circulating tumor cells (CTCs), hematopoietic stem cells, and hematopoietic progenitor cells. In various embodiments, the leukocytes are myeloid cells and lymphoid cells. In various embodiments, myeloid cells are monocytes, macrophages, neutrophils, granulocytes, dendritic cells, mast cells, eosinophils, and basophils. In various embodiments, the lymphoid cells are T cells, B cells, NK cells, NK-T cells, or iNK cells.

In various embodiments, the analysis of cells from one or more blood samples collected from a subject suffering from cancer demonstrates increased levels of immune suppressive cells compared to the analysis of cells from one or more healthy subjects and/or one or more subjects suffering from cancer and responsive to treatment. In various embodiments, the immune suppressive cells are myeloid derived suppressor cells (MDSCs), tumor-associated macrophages (TAMs), neutrophils, $T_{reg}$ cells, and $B_{reg}$ cells. In various embodiments, MDSCs are monocytic MDSCs (M-MDSCs) and polymorphonuclear MDSCs (PMN-MDSCs). In various embodiments, the TAMs are M2 TAMs. In various embodiments, the immune suppressive cells are CAFs. In various embodiments, the levels of immune suppressive cells in one or more blood samples of a subject having one or more tumors characterized as immune evasive, immunologically protected, and/or immunologically 'cold' are increased by about 5-100% (e.g., about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more blood samples collected from one or more healthy subjects and/or one or more subjects suffering from cancer and responsive to treatment. In various embodiments, the levels of immune suppressive cells in one or more blood samples of a subject having one or more tumors characterized as immune evasive, immunologically protected, and/or immunologically 'cold' are increased by about 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from one or more healthy subjects and/or one or more subjects suffering from cancer and responsive to treatment. In various embodiments, immune suppressive cells are identified by the assay of cell-surface proteins expression. In various embodiments, the analysis of cells from one or more blood samples collected from a subject having one or more tumors characterized as immune evasive, immunologically protected, and/or immunologically 'cold' demonstrates reduced levels or absence of activated pro-inflammatory immune cells (e.g., reduced relative to a healthy subject or a subject suffering from cancer and responsive to treatment by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values).

In various embodiments, the analysis of cells from one or more blood samples collected from a subject having one or more tumors characterized as immune evasive, immunologically protected, and/or immunologically 'cold' demonstrates reduced levels or absence of activated pro-inflammatory immune cells (e.g., reduced relative to a healthy subject or a subject suffering from cancer and responsive to treatment by about 2, 5, 10, 15, 20, 25, 30, 35, 40, 45, 50, 55, 60, 65, 70, 75, 80, 85, 90, 95, or 100 fold inclusive of all values and ranges between these values). In various embodiments, the activated pro-inflammatory cells are dendritic cells (DCs), macrophages, M1 macrophages, T-cells, B-cells, NK cells, NK-T cells, and iNK cells. In various embodiments, the frequency of pro-inflammatory immune cells is ≤10% (e.g., about 9%, about 8%, about 7%, about 6%, about 5%, about 4%, about 3%, about 2%, or about 1%) of all leukocytes analyzed from one or more blood samples collected from the subject. In various embodiments, activated pro-inflammatory immune cells are identified by the assay of cell-surface protein expression.

In various embodiments, the analysis of cells in one or more blood samples of a subject suffering from cancer is performed by the assay of cell-surface proteins. In various embodiments, the cell-surface proteins are selected from the group consisting of receptor tyrosine kinase (RTK), CD1c, CD2, CD3, CD4, CD5, CD8, CD9, CD10, CD11b, CD11c, CD14, CD15, CD16, CD18, CD19, CD20, CD21, CD22, CD23, CD24, TACI, CD25, CD27, CD28, CD30, CD30L, CD31, CD32, CD32b, CD34, CD33, CD38, CD39, CD40, CD40-L, CD41b, CD42a, CD42b, CD43, CD44, CD45, CD47, CD45RA, CD45RO, CD48, CD52, CD55, CD56, CD58, CD61, CD66b, CD70, CD72, CD79, CD68, CD84, CD86, CD93, CD94, CD95, CRACC, BLAME, BCMA, CD103, CD107, CD112, CD120a, CD120b, CD123, CD125, CD134, CD135, CD140a, CD141, CD154, CD155, CD160, CD163, CD172a, XCR1, CD203c, CD204, CD206, CD207 CD226, CD244, CD267, CD268, CD269, CD355, CD358, NKG2A, NKG2B, NKG2C, NKG2D, NKG2E, NKG2F, NKG2H, KIR2DL1, KIR2DL2, KIR2DL3, KIR2DL5A, KIR2DL5B, KIR3DL1, KIR3DL2, KIR3DL3, KIR3DL4, KIR2DS1, KIR2DS2, KIR2DS3, KIR2DS4, KIR2DS5, DAP12, KIR3DS, NKp44, NKp46, TCR, BCR, Integrins, $Fc\beta_{\varepsilon}RI$, MHC-I, MHC-II, IL-1R, IL-2Rα, IL-2Rβ, IL-2Rγ, IL-3Rα, CSF2RB, IL-4R, IL-5Rα, CSF2RB, IL-6Rα, gp130, IL-7Rα, IL-9R, IL-12Rβ1, IL-12Rβ2, IL-13Rα1, IL-13Rα2, IL-15Rα, IL-21R, IL23R, IL-27Rα, IL-31Rα, OSMR, CSF-1R, cell-surface IL-15, IL-10Rα, IL-10Rβ, IL-20Rα, IL-20Rβ, IL-22Rα1, IL-22Rα2, IL-22Rβ, IL-28RA, PD-1, PD-1H, BTLA, CTLA-4, PD-L1, PD-L2, 2B4, B7-1, B7-2, B7-H1, B7-H4, B7-DC, DR3, LIGHT, LAIR, LTα1β2, LTβR, TIM-1, TIM-3, TIM-4, TIGIT, LAG-3, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CLECL9a, DC-SIGN, IGSF4A, SIGLEC, EGFR, PDGFR, VEGFR, FAP, α-SMA, Vimentin, Laminin, FAS, FAS-L, Fc, ICAM-1, ICAM-2, ICAM-3, ICAM-4, ICAM-5, PECAM-1, MICA, MICB, UL16, ULBP1, ULBP2, ILBP3, ULBP4, ULBP5, ULBP6, MULTI, RAE1 α, β, γ, δ, and ε, $A_1R$, $A_{2A}R$, $A_{2B}R$, and $A_3R$, H60a, H60b, and H60c. In various embodiments, Integrins are selected from the group consisting of α1, α2, αIIb, α3, α4, α5, α6, α7, α8, α9, α10, α11, αD, αE, αL, αM, αV, αX, β1, β2, β3, β4, β5, β6, β7, β8, and/or combinations thereof. In various embodiments, TCR is selected from the group consisting of α, β, γ, δ, ε, and ζ TCR. Several methods have been described in the literature for assaying of cell-surface protein expression, including Flow Cytometry and Mass Cytometry (CyTOF). The presence or abundance of one or more of these cell-surface proteins indicates that the patient is amendable to treatment with the methods disclosed herein.

In various embodiments, the analysis of cells from one or more blood samples collected from a subject having one or more tumors characterized as immune evasive, immunologically protected, and/or immunologically 'cold' demonstrates a high neutrophil to lymphocyte ratio (NLR). In various embodiments, the analysis of cells from one or more blood samples collected from a subject having one or more tumors characterized as immune evasive, immunologically protected, and/or immunologically 'cold' demonstrates an NLR≥2. In various embodiments, the analysis of cells from one or more blood samples collected from a subject having one or more tumors characterized as immune evasive, immunologically protected, and/or immunologically 'cold' demonstrates NLR of between 2 and 10 (e.g., NLR of 2, 3, 4, 5, 6, 7, 8, 9, and 10, inclusive of all values and ranges between these values). In various embodiments, NLR is used to determine the prognosis for a subject suffering from cancer and having one or more tumors characterized as immune evasive, immunologically protected, and/or immunologically 'cold'. In various embodiments, NLR≥2 determines a poor prognosis.

In various embodiments, the cells analyzed from one or more blood samples collected from a subject suffering from cancer are circulating tumor cells (CTCs). In various embodiments, the assay of one or more blood samples collected from a subject suffering from cancer demonstrates increased frequency of CTCs compared to the analysis of one or more blood samples collected from one or more healthy subjects and/or one or more subjects suffering from cancer and responsive to treatment. In various embodiments, the frequency of circulating tumor cells in one or more blood samples of a subject having one or more tumors characterized as immune evasive, immunologically protected, and/or immunologically 'cold' is ≥3 or ≥5 CTCs per 7.5 mL blood.

In various embodiments, the tumor characteristic of a subject suffering from cancer is determined from the analysis of proteins in one or more blood samples of the subject. In various embodiments, the tumor characteristic of a subject suffering from cancer is determined by comparing the analysis of proteins in one or more blood samples from the subject suffering from cancer to the analysis of one or more blood samples from one or more healthy subjects and/or one or more subjects suffering from cancer and responsive to treatment. In various embodiments, the protein is an intracellular protein or a secreted protein. In various embodiments, the protein is selected from the group consisting of cytokines, chemokines, growth factors, enzymes, proteases, and nucleases. In various embodiments, cytokines and chemokines are selected from the group consisting of IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, CCL1, CCL2, CCL3, CCL4, CCL5, CCL6, CCL7, CCL8, CCL9, CCL10, CCL11, CCL12, CCL14, CCL15, CCL16, CCL17, CCL18, CCL19, CCL20, CCL21, CCL22, CCL23, CCL24, CCL25, CCL26, CCL27, CCL28, CXCL1, CXCL2 (MCP-1), CXCL3 (MIP-1α), CXCL4 (MIP-1β), CXCL5 (RANTES), CXCL6, CXCL7, CXCL8, CXCL9, CXCL10, CXCL11, CXCL12, CXCL13, CXCL14, CXCL15, CXCL16, CXCL17, IFN-α, IFN-β, IFN-γ, Granzyme-B, Perforin, TNF-α, TGF-β1, TGF-β2, and TGF-β3. In various embodiments, the growth factors are selected from the group consisting of EGF, FGF, NGF, PDGF, VEGF, IGF, GMCSF, GCSF, TGF, Erythropieitn, TPO, BMP, HGF, GDF, Neurotrophins, MSF, SGF, GDF, G-CSF, and GM-CSF. In various embodiments, the protein is a protease is selected from the group consisting of aspartic protease, a cysteine protease, a metalloprotease, a serine protease, and/or a threonine protease. In some embodiments, the protein is a protease is selected from the group consisting of ADAM1, ADAM2, ADAM7, ADAM8, ADAM9, ADAM10, ADAM11, ADAM12, ADAM15, ADAM17, ADAM18, ADAM19, ADAAM20, ADAM21, ADAM22, ADAM23, ADAM28, ADAM29, ADAM30, ADAM33, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28. In various embodiments, the protein is an enzyme selected from the group consisting of arginase, asparaginase, kynurinase, indoleamine 2,3 dioxygenase (IDO1 and IDO2), tryptophan 2,3 dioxygenase (TDO), and IL4I1. In various embodiments, the protein is associated with apoptosis. In various embodiments, proteins associated with apoptosis are selected from the group consisting of P53, Caspase 1, Caspase 2, Caspase 3, Caspase 4, Caspase 5, Caspase 6, Caspase 7, Caspase 8, Caspase 9, Caspase 10, Caspase 11, Caspase 12, Caspase 13, Caspase 14, BCL-2, BCL-XL, MCL-1, CED-9, A1, BFL1, BAX, BAK, DIVA, BCL-XS, BIK, BIM, BAD, BID, and EGL-1. Several methods have been described in the literature for assaying proteins from blood samples, including western blot, and ELISA.

In various embodiments, the analysis of proteins from one or more blood samples of a subject having one or more tumors that are characterized as immune evasive, immunologically protected, and/or immunologically 'cold' demonstrates increased levels of tumor promoting, anti-inflammatory, and/or immune suppressive proteins. In various embodiments, the tumor promoting, anti-inflammatory, and/or immune suppressive proteins are cell-surface proteins, intracellular proteins, or secreted proteins. In various embodiments, the tumor promoting, anti-inflammatory, and/or immune suppressive proteins are selected from the group consisting of CD39, CD79, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28, CXCL12, GM-CSF, G-CSF, TGF-β1, TGF-β2, and TGF-β3, arginase, asparaginase, kyneurinase, indoleamine 2,3 dioxygenase (IDO1 and IDO2), tryptophan 2,3 dioxygenase (TDO), myeloperoxidase (MPO), neutrophil elastase (NE), and IL4I1. In various embodiments, the levels of tumor promoting, anti-inflammatory, and/or immune suppressive proteins in one or more blood samples of a subject having one or more tumors that are characterized as immune evasive, immunologically protected, and/or immunologically 'cold' are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected from one or more healthy subjects and/or one or more subjects suffering from cancer and responsive to treatment. In various embodiments, the levels of tumor promoting, anti-inflammatory, and/or immune suppressive proteins in one or more blood samples of a subject having one or more tumors that are characterized as immune evasive, immunologically protected, and/or immunologically 'cold' are increased by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from one or more healthy subjects and/or one or more subjects suffering from cancer and responsive to treatment. In various embodiments, the analysis of proteins from one or more blood samples of a subject having one or more tumors that are characterized as immune evasive, immunologically protected, and/or immunologically 'cold' demonstrate reduced levels, low levels, and/or absence of tumor inhibiting, anti-tumor, and/or pro-inflammatory proteins. In various embodiments, tumor inhibiting, anti-tumor, and/or pro-inflammatory proteins are selected from the group consisting of IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, cell-surface IL-15, CXCL2 (MCP-1), CXCL3 (MIP-1α), CXCL4 (MIP-1β), CXCL5 (RANTES), IFN-α, IFN-β, IFN-γ, Granzyme-B, Perforin, and TNF-α. In various embodiments, the levels of tumor inhibiting, anti-tumor, and/or pro-inflammatory proteins in one or more blood samples of a subject having one or more tumors that are characterized as immune evasive, immunologically protected, and/or immunologically 'cold' are decreased by 5-100% (e.g., reduced relative to a healthy subject or a subject suffering from cancer and responsive to treatment by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected from one or more healthy subjects and/or one or more subjects suffering from cancer and responsive to treatment. In various embodiments, the levels of tumor inhibiting, anti-tumor, and/or pro-inflammatory proteins in one or more blood samples of a subject having one or more tumors that are characterized as immune evasive, immunologically protected, and/or immunologically 'cold' are decreased by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from one or more healthy subjects or subjects suffering from cancer and responsive to treatment. Several methods have been described in the literature for assaying proteins from blood samples, including western blot, and ELISA.

In various embodiments, the analysis of one or more blood samples of a subject having one or more tumors that are characterized as immune evasive, immunologically protected, and/or immunologically 'cold' demonstrates increased levels of neutrophil extracellular traps (NETs). In various embodiments, the analysis of one or more blood samples of a subject having one or more tumors that are characterized as immune evasive, immunologically protected, and/or immunologically 'cold' demonstrates increased levels of neutrophil extracellular traps (NETs) compared to the analysis of one or more blood samples from one or more healthy subjects and/or one or more subjects suffering from cancer and responsive to treatment. In various embodiments, the levels of NETs in one or more blood samples of a subject having one or more tumors that are characterized as immune evasive, immunologically protected, and/or immunologically 'cold' are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected from one or more healthy subjects and/or one or more subjects suffering from cancer and responsive to treatment. In various embodiments, the levels of NETs in one or more blood samples of a subject having one or more tumors that are characterized as immune evasive, immunologically protected, and/or immunologically 'cold' are increased by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from one or more healthy subjects and/or one or more subjects suffering from cancer and responsive to treatment. Several methods have been described in the literature for assaying NETs from blood samples, including western blot, ELISA, and flow cytometry.

In various embodiments, the tumor characteristic of a subject suffering from cancer is determined from the analysis of nucleic acids in one or more blood samples of the subject. In various embodiments, the tumor characteristic of a subject suffering from cancer is determined by comparing the analysis of nucleic acids in one or more blood samples from the subject suffering from cancer to the analysis of one or more blood samples from one or more healthy subjects and/or one or more subjects suffering from cancer and responsive to treatment. In various embodiments, the nucleic acid is selected from the group comprising DNA, ssDNA, circulating tumor DNA (ctDNA), RNA, mRNA, dsRNA, siRNA, miRNA, and lncRNA. In various embodiments, the analysis of ctDNA from one or more blood samples of a subject having one or more tumors that are characterized as immune evasive, immunologically protected, immunologically 'cold' demonstrates low levels and/or absence of one or more tumor mutations, tumor antigens, and/or neoantigens. In various embodiments, the analysis of ctDNA from one or more blood samples of a subject suffering from cancer demonstrates a low or no tumor mutation burden. In various embodiments, the analysis of ctDNA from one or more blood samples of a subject having one or more tumors that are characterized as immune evasive, immunologically protected, immunologically 'cold' demonstrates a tumor mutation burden of between 5 and 0.001 somatic mutations per mega base pairs (e.g., about 5, about 4, about 3, about 2, about 1, about 0.9, about 0.8, about 0.7, about 0.6, about 0.5, about 0.4, about 0.3, about 0.2, about 0.1, about 0.09, about 0.08, about 0.07, about 0.06, about 0.05, about 0.04, about 0.03, about 0.02, about 0.01, about 0.009, about 0.008, about 0.007, about 0.006, about 0.005, about 0.004, about 0.003, about 0.002, or 0.001, inclusive of all values and ranges between these values). In various embodiments, the nucleic acid analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the tumor characteristic of a subject is determined from the gene expression analysis from nucleic acids in one or more blood samples of a subject suffering from cancer. In various embodiments, gene expression analysis from nucleic acids in one or more blood samples of a subject having one or more tumors that are characterized as immune evasive, immunologically protected, immunologically 'cold' demonstrates increased expression of tumor promoting, tumor permissive, and/or immune suppressive genes compared to the analysis of one or more blood samples from one or more healthy subjects and/or one or more subjects suffering from cancer and responsive to treatment. In various embodiments, the expression of tumor promoting, tumor permissive, and/or immune suppressive genes in one or more blood samples of a subject having one or more tumors that are characterized as immune evasive, immunologically protected, immunologically 'cold' is increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more blood samples collected from one or more healthy subjects and/or one or more subjects suffering from cancer and responsive to treatment. In various embodiments, the expression of tumor promoting, tumor permissive, and/or immune suppressive genes in one or more blood samples of a subject having one or more tumors that are characterized as immune evasive, immunologically protected, immunologically 'cold' is increased by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from one or more healthy subjects and/or one or more subjects suffering from cancer and responsive to treatment. In various embodiments, the analysis of nucleic acids in one or more blood samples of a subject having one or more tumors that are characterized as immune evasive, immunologically protected, immunologically 'cold' demonstrates decreased expression of tumor inhibiting, anti-tumor, and/or pro-inflammatory genes compared to the analysis of one or more blood samples from one or more healthy subjects and/or one or more subjects suffering from cancer and responsive to treatment. In various embodiments, the analysis of nucleic acids in one or more blood samples of a subject having one or more tumors that are characterized as immune evasive, immunologically protected, immunologically 'cold' demonstrates low or no expression of tumor inhibiting, anti-tumor, and/or anti-inflammatory genes compared to the analysis of one or more blood samples from one or more healthy subjects and/or one or more subjects suffering from cancer and responsive to treatment. In various embodiments, the expression of tumor inhibiting, anti-tumor, and/or pro-inflammatory genes in one or more blood samples of a subject having one or more tumors that are characterized as immune evasive, immunologically protected, immunologically 'cold' is decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to a healthy subject or a subject suffering from cancer who is responsive to therapy. In various embodiments, the expression of tumor inhibiting, anti-tumor, and/or pro-inflammatory genes in one or more blood samples of a subject having one or more tumors that are characterized as immune evasive, immunologically protected, immunologically 'cold' is reduced by 2-100 fold (e.g., reduced relative to a healthy subject or a subject suffering from cancer and responsive to therapy by about 2, 5, 10, 15, 20, 25, 30, 35, 40, 45, 50, 55, 60, 65, 70, 75, 80, 85, 90, 95, or 100 fold, inclusive of all values and ranges between these values). In various embodiments, the gene expression analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the tumor characteristic of a subject suffering from cancer is determined from the analysis of one or more tumor samples collected from the subject. In various embodiments, the tumor sample is a biopsy. In various embodiments, the tumor characteristic of a subject suffering from cancer is determined from the analysis of cells, proteins, and/or nucleic acids in one or more tumor samples collected from the subject. In various embodiments, the tumor characteristic of a subject suffering from cancer is determined by comparing the analysis of cells, proteins, and/or nucleic acids in one or more tumor samples from the subject suffering from cancer to the analysis of tissue samples from one or more healthy subjects and/or one or more subjects suffering from cancer and responsive to treatment. In various embodiments, the cells analyzed in one or more tumor samples are leukocytes, epithelial cells, mesenchymal cells, mesenchymal stem cells, stromal cells, endothelial cells, fibroblasts, pericytes, adipocytes, and cancer stem cells. In various embodiments, the leukocytes are myeloid cells and lymphoid cells. In various embodiments, myeloid cells are monocytes, macrophages, neutrophils, granulocytes, dendritic cells, mast cells, eosinophils, and basophils. In various embodiments, the lymphoid cells are T cells, B cells, NK cells, NK-T cells, or iNK cells.

In various embodiments, the analysis of cells from one or more tumor samples collected from a subject having one or more tumors that are characterized as immune evasive, immunologically protected, immunologically 'cold' demonstrates the presence of immune suppressive cells. In various embodiments, the analysis of one or more tumor samples collected from a subject having one or more tumors that are characterized as immune evasive, immunologically protected, immunologically 'cold' demonstrates the presence of immune suppressive cells in the tumor core. In various embodiments, the analysis of cells from one or more tumor samples collected from a subject having one or more tumors that are characterized as immune evasive, immunologically protected, immunologically 'cold' demonstrates increased levels of immune suppressive cells. In various embodiments, the analysis of one or more tumor samples demonstrates increased levels of immune suppressive cells in the tumor core. In various embodiments, the immune suppressive cells are myeloid derived suppressor cells (MDSCs), tumor-associated macrophages (TAMs), neutrophils, $T_{reg}$ cells, and $B_{reg}$ cells. In various embodiments, MDSCs are monocytic MDSCs (M-MDSCs) and polymorphonuclear MDSCs (PMN-MDSCs). In various embodiments, the TAMs are M2 TAMs. In various embodiments, the immune suppressive cells are CAFs. In various embodiments, the levels of immune suppressive cells in one or more tumor samples of a subject having one or more tumors that are characterized as immune evasive, immunologically protected, immunologically 'cold' are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to tissue samples of one or more healthy subjects and/or one or more subjects suffering from cancer and responsive to treatment. In various embodiments, the levels of immune suppressive cells in one or more tumor samples of a subject having one or more tumors that are characterized as immune evasive, immunologically protected, immunologically 'cold' are increased by 2-100-fold (e.g., increased relative to a healthy subject and/or a subject suffering from cancer and responsive to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tissue samples and/or one or more healthy subjects or one or more subjects suffering from cancer and responsive to treatment.

In various embodiments, the analysis of cells from one or more tumor samples collected from a subject having one or more tumors that are characterized as immune evasive, immunologically protected, immunologically 'cold' demonstrates the absence of leukocytes. In various embodiments, the analysis of cells from one or more tumor samples collected from a subject having one or more tumors that are characterized as immune evasive, immunologically protected, immunologically 'cold' demonstrates the reduced or low levels of leukocytes. In various embodiments, the frequency of leukocytes is ≤50%, ≤40%, ≤30%, ≤20%, ≤10%, or ≤5%, inclusive of all values and ranges between these values, of all cells analyzed.

In various embodiments, the analysis of cells from one or more tumor samples collected from a subject having one or more tumors that are characterized as immune evasive, immunologically protected, immunologically 'cold' demonstrates the absence of activated pro-inflammatory immune cells. In various embodiments, the analysis of cells from one or more tumor samples collected from a subject having one or more tumors that are characterized as immune evasive, immunologically protected, immunologically 'cold' demonstrates the absence of activated pro-inflammatory immune cells from the tumor core. In various embodiments, the analysis of cells from one or more tumor samples collected from a subject having one or more tumors that are characterized as immune evasive, immunologically protected, immunologically 'cold' demonstrates low or reduced levels of activated pro-inflammatory immune cells. In various embodiments, the analysis of cells from one or more tumor samples collected from a subject having one or more tumors that are characterized as immune evasive, immunologically protected, immunologically 'cold' demonstrates low or reduced levels of activated pro-inflammatory immune cells in the tumor core. In various embodiments, the activated pro-inflammatory cells are dendritic cells (DCs), macrophages, M1 macrophages, T-cells, B-cells, NK cells, NK-T cells, and iNK cells. In various embodiments, the frequency of pro-inflammatory immune cells is ≤50%, ≤40%, ≤30%, ≤20%, ≤10%, or ≤5%, inclusive of all values and ranges between these values, of all cells analyzed.

In various embodiments, the tumor characteristic of a subject suffering from cancer is determined from the analysis of the location of immune cells in one or more tumor samples of the subject. In various embodiments, immune cells in one or more tumor samples of a subject having one or more immune evasive, immunologically protected, and/or immunologically 'cold' are located in the tumor periphery. In various embodiments, immune cells in one or more tumor samples of a subject having one or more immune evasive, immunologically protected, and/or immunologically 'cold' are absent from the tumor core. In various embodiments, immune cells in one or more tumor samples of a subject having one or more immune evasive, immunologically protected, and/or immunologically 'cold' are reduced in the tumor core. In various embodiments, immune cells in the tumor core are reduced by 5-100% (e.g., relative to a healthy subject and/or a subject suffering from cancer and responsive to treatment by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more samples from one or more healthy subjects and/or one or more subjects suffering from cancer and responsive to treatment.

In various embodiments, the tumor characteristic of a subject suffering from cancer is determined from the analysis of the location of stromal cells in one or more tumor samples of the subject. In various embodiments, the stromal cells are CAFs, pericytes, adipocytes, and endothelial cells. In various embodiments, CAFs in one or more tumor samples of a subject having one or more immune evasive, immunologically protected, and/or immunologically 'cold' tumors are increased in the tumor periphery. In various embodiments, CAFs in one or more tumor samples of a subject having one or more immune evasive, immunologically protected, and/or immunologically 'cold' tumors are increased in the tumor core. In various embodiments, the frequency of CAFs in the tumor periphery is increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tissue sample from one or more healthy subjects and/or subjects suffering from cancer and responsive to treatment. In various embodiments, the frequency of CAFs in the tumor periphery is increased by 2-100 fold (e.g., increased by about 2, 5, 10, 15, 20, 25, 30, 35, 40, 45, 50, 55, 60, 65, 70, 75, 80, 85, 90, 95 fold, inclusive of all values and ranges between these values) compared to one or more tissue samples from one or more healthy subjects and/or one or more subjects suffering from cancer and responsive to treatment. In various embodiments, the frequency of CAFs in the tumor core is increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tissue samples of one or more healthy subjects and/or one or more subjects suffering from cancer and responsive to treatment. In various embodiments, the frequency of CAFs in the tumor core is increased by 2-100 fold (e.g., increased relative to a healthy subject and/or a subject suffering from cancer and responsive to treatment by about 2, 5, 10, 15, 20, 25, 30, 35, 40, 45, 50, 55, 60, 65, 70, 75, 80, 85, 90, 95 fold, inclusive of all values and ranges between these values) compared to one or more healthy tissue samples.

In various embodiments, the analysis of cells in one or more tumor samples of a subject suffering from cancer is performed by the assay of cell-surface proteins. In various embodiments, the cell-surface proteins are selected from the group consisting of receptor tyrosine kinase (RTK), CD1c, CD2, CD3, CD4, CD5, CD8, CD9, CD10, CD11b, CD11c, CD14, CD15, CD16, CD18, CD19, CD20, CD21, CD22, CD23, CD24, TACI, CD25, CD27, CD28, CD30, CD30L, CD31, CD32, CD32b, CD34, CD33, CD38, CD39, CD40, CD40-L, CD41b, CD42a, CD42b, CD43, CD44, CD45, CD47, CD45RA, CD45RO, CD48, CD52, CD55, CD56, CD58, CD61, CD66b, CD70, CD72, CD79, CD68, CD84, CD86, CD93, CD94, CD95, CRACC, BLAME, BCMA, CD103, CD107, CD112, CD120a, CD120b, CD123, CD125, CD134, CD135, CD140a, CD141, CD154, CD155, CD160, CD163, CD172a, XCR1, CD203c, CD204, CD206, CD207 CD226, CD244, CD267, CD268, CD269, CD355, CD358, NKG2A, NKG2B, NKG2C, NKG2D, NKG2E, NKG2F, NKG2H, KIR2DL1, KIR2DL2, KIR2DL3, KIR2DL5A, KIR2DL5B, KIR3DL1, KIR3DL2, KIR3DL3, KIR3DL4, KIR2DS1, KIR2DS2, KIR2DS3, KIR2DS4, KIR2DS5, DAP12, KIR3DS, NKp44, NKp46, TCR, BCR, Integrins, $Fc\beta_{\varepsilon}RI$, MHC-I, MHC-II, IL-1R, IL-2Rα, IL-2Rβ, IL-2Rγ, IL-3Rα, CSF2RB, IL-4R, IL-5Rα, CSF2RB, IL-6Rα, gp130, IL-7Rα, IL-9R, IL-12Rβ1, IL-12Rβ2, IL-13Rα1, IL-13Rα2, IL-15Rα, IL-21R, IL23R, IL-27Rα, IL-31Rα, OSMR, CSF-1R, cell-surface IL-15, IL-10Rα, IL-10Rβ, IL-20Rα, IL-20Rβ, IL-22Rα1, IL-22Rα2, IL-22Rβ, IL-28RA, PD-1, PD-1H, BTLA, CTLA-4, PD-L1, PD-L2, 2B4, B7-1, B7-2, B7-H1, B7-H4, B7-DC, DR3, LIGHT, LAIR, LTα1β2, LTβR, TIM-1, TIM-3, TIM-4, TIGIT, LAG-3, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CLECL9a, DC-SIGN, IGSF4A, SIGLEC, EGFR, PDGFR, VEGFR, FAP, α-SMA, Vimentin, Laminin, FAS, FAS-L, $F_C$, ICAM-1, ICAM-2, ICAM-3, ICAM-4, ICAM-5, PECAM-1, MICA, MICB, UL16, ULBP1, ULBP2, ILBP3, ULBP4, ULBP5, ULBP6, MULTI, RAE1 α, β, γ, δ, and ε, $A_1R$, $A_{2A}R$, $A_{2B}R$, and $A_3R$, H60a, H60b, and H60c. In various embodiments, Integrins are selected from the group consisting of α1, α2, αIIb, α3, α4, α5, α6, α7, α8, α9, α10, α11, αD, αE, αL, αM, αV, αX, β1, β2, β3, β4, β5, β6, β7, β8, and/or combinations thereof. In various embodiments, TCR is selected from the group consisting of α, β, γ, δ, ε, and ζ TCR. Several methods have been described in the literature for assaying of cell-surface protein expression from tumor samples, including immunohistochemistry, immunofluorescence, western blot, flow cytometry, and Mass Cytometry (CyTOF).

Tumor core is generally described as the densely packed, central, bulk-forming and differentiated region of the tumor. In contrast, the tumor periphery is generally described as the invasive edge of the tumor that interacts with the surrounding stroma and parenchyma[35, 36].

In various embodiments, the tumor characteristic of a subject suffering from cancer is determined from the analysis of proteins in one or more tumor samples of the subject. In various embodiments, the tumor characteristic of a subject suffering from cancer is determined by comparing the analysis of proteins in one or more tumor samples from the subject suffering from cancer to the analysis of one or more tissues from one or more healthy subjects and/or one or more subjects suffering from cancer and responsive to treatment. In various embodiments, the protein is intracellular or extracellular. In various embodiments, the protein is selected from the group consisting of cytokines, chemokines, growth factors, enzymes, proteases, and nucleases. In various embodiments, cytokines and chemokines are selected from the group consisting of IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, CCL1, CCL2, CCL3, CCL4, CCL5, CCL6, CCL7, CCL8, CCL9, CCL10, CCL11, CCL12, CCL14, CCL15, CCL16, CCL17, CCL18, CCL19, CCL20, CCL21, CCL22, CCL23, CCL24, CCL25, CCL26, CCL27, CCL28, CXCL1, CXCL2 (MCP-1), CXCL3 (MIP- 1a), CXCL4 (MIP-1(3), CXCL5 (RANTES), CXCL6, CXCL7, CXCL8, CXCL9, CXCL10, CXCL11, CXCL12, CXCL13, CXCL14, CXCL15, CXCL16, CXCL17, IFN-α, IFN-β, IFN-γ, Granzyme-B, Perforin, TNF-α, TGF-β1, TGF-β2, and TGF-β3. In various embodiments, the growth factors are selected from the group consisting of EGF, FGF, NGF, PDGF, VEGF, IGF, GMCSF, GCSF, TGF, Erythropieitn, TPO, BMP, HGF, GDF, Neurotrophins, MSF, SGF, GDF, G-CSF, and GM-CSF. In various embodiments, the protein is a protease is selected from the group consisting of aspartic protease, a cysteine protease, a metalloprotease, a serine protease, and/or a threonine protease. In some embodiments, the protein is a protease is selected from the group consisting of ADAM1, ADAM2, ADAM7, ADAM8, ADAM9, ADAM10, ADAM11, ADAM12, ADAM15, ADAM17, ADAM18, ADAM19, ADAAM20, ADAM21, ADAM22, ADAM23, ADAM28, ADAM29, ADAM30, ADAM33, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28. In various embodiments, the protein is an enzyme selected from the group consisting of arginase, asparaginase, kynurinase, indoleamine 2,3 dioxygenase (IDO1 and IDO2), tryptophan 2,3 dioxygenase (TDO), and IL4I1. In various embodiments, the protein is associated with apoptosis. In various embodiments, proteins associated with apoptosis are selected from the group consisting of P53, Caspase 1, Caspase 2, Caspase 3, Caspase 4, Caspase 5, Caspase 6, Caspase 7, Caspase 8, Caspase 9, Caspase 10, Caspase 11, Caspase 12, Caspase 13, Caspase 14, BCL-2, BCL-XL, MCL-1, CED-9, A1, BFL1, BAX, BAK, DIVA, BCL-XS, BIK, BIM, BAD, BID, and EGL-1. Several methods have been described in the literature for assaying proteins from tumor samples, including immunohistochemistry, immunofluorescence, western blot, and ELISA.

In various embodiments, the analysis of proteins from one or more tumor samples of a subject having one or more tumors characterized as immune evasive, immunologically protected, and/or immunologically 'cold' demonstrates increased levels of proteins associated with tumor progression, anti-inflammatory activity, and/or immune suppression. In various embodiments, proteins associated with tumor progression, anti-inflammatory activity, and/or immune suppression are cell-surface proteins, intracellular proteins, or secreted proteins. In various embodiments, proteins associated with tumor progression, anti-inflammatory activity, and/or immune suppression are selected from the group consisting of CD39, CD47, CD79, CD140a, CD163, CD206, FOXP3, FAP, PD-1, PD-L1, PD-L2, CSF-1R, $A_1R$, $A_{2A}R$, $A_{2B}R$, and $A_3R$, TIM-1, TIM-3, TIM-4, TIGIT, CSFR, SIGLEC, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28, CXCL12, GM-CSF, G-CSF, FAP, TGF-β1, TGF-β2, and TGF-β3, arginase, asparaginase, kyneurinase, indoleamine 2,3 dioxygenase (IDO1 and IDO2), tryptophan 2,3 dioxygenase (TDO), myeloperoxidase (MPO), neutrophil elastase (NE), and IL4I1. In various embodiments, the levels of proteins associated with tumor progression, anti-inflammatory activity, and/or immune suppression in one or more tumor samples of a subject having one or more tumors characterized as immune evasive, immunologically protected, and/or immunologically 'cold' are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tissue samples from one or more healthy subjects and/or one or more subjects suffering from cancer and responsive to treatment. In various embodiments, the levels of proteins associated with tumor progression, anti-inflammatory activity, and/or immune suppression in one or more tumor samples of a subject having one or more tumors characterized as immune evasive, immunologically protected, and/or immunologically 'cold' are increased by 2-100 fold (e.g., increased relative to a healthy subject and/or a subject suffering from cancer and responsive to treatment by about 2, 5, 10, 15, 20, 25, 30, 35, 40, 45, 50, 55, 60, 65, 70, 75, 80, 85, 90, 95 fold, inclusive of all values and ranges between these values) compared to one or more tissue samples from one or more healthy subjects and/or subjects suffering from cancer and responsive to treatment.

In various embodiments, the analysis of proteins from one or more tumor samples of a subject having one or more tumors characterized as immune evasive, immunologically protected, and/or immunologically 'cold' demonstrate reduced levels, low levels, and/or absence of proteins associated with tumor growth inhibition, anti-tumor activity, and/or pro-inflammatory activity. In various embodiments, proteins associated with tumor growth inhibition, anti-tumor activity, and/or pro-inflammatory activity are selected from the group consisting of CD44, CD56, CD103c, CD69, KG2A, NKG2B, NKG2C, NKG2D, NKG2E, NKG2F, NKG2H, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, CXCL2 (MCP-1), CXCL3 (MIP-1α), CXCL4 (MIP-1β), CXCL5 (RANTES), IFN-α, IFN-β, IFN-γ, Granzyme-B, Perforin, and TNF-α. In various embodiments, the levels of proteins associated with tumor growth inhibition, anti-tumor activity, and/or pro-inflammatory activity are reduced by 5-100% (e.g., reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more samples collected from one or more healthy tissues and/or one or more tumor samples collected from a subject suffering from cancer and responsive to treatment. Several methods have been described for assaying proteins from tumor samples, including immunohistochemistry, immunofluorescence, western blot, intracellular flow cytometry, and ELISA.

In various embodiments, the tumor characteristic of a subject suffering from cancer is determined from the Tumor Proportion Score (TPS) for PD-L1 expression in one or more tumor samples from the subject. In various embodiments, the TPS of a subject having one or more tumors that are characterized as immune evasive, immunologically protected, and/or immunologically 'cold' of between 1 and 50 (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50, inclusive of all ranges between these values). In various embodiments, the TPS of a subject having one or more tumors that are characterized as immune evasive, immunologically protected, and/or immunologically 'cold' is ≤1. TPS for PD-L1 expression is defined as the percentage of viable tumor cells demonstrating partial or complete membrane staining by immunohistochemical analysis.

In various embodiments, the tumor characteristic of a subject suffering from cancer is determined from the Combined Positivity Score (CPS) for PD-L1 expression in one or more tumor samples from the subject. In various embodiments, the CPS of a subject having one or more tumors that are characterized as immune evasive, immunologically protected, and/or immunologically 'cold' is ≤10 (e.g., 1, 2, 3, 4, 5, 6, 7, 8, 9, or 10, inclusive of all ranges between these values). In various embodiments, the CPS is ≤1. CPS for PD-L1 expression is determined from the immunohistochemical determination of the number of viable tumor cells, lymphocytes, and macrophages positive for PD-L1 as a percentage of all viable tumor cells.

In various embodiments, the tumor characteristic of a subject suffering from cancer is determined from microsatellite instability testing of one or more tumor samples from the subject. In various embodiments, the tumor characteristic of a subject suffering from cancer is determined by comparing microsatellite instability testing of one or more tumor samples to microsatellite stability testing from one or more healthy tissues of the subject. In various embodiments, the microsatellite instability testing is the assay of microsatellite markers. In various embodiments, the microsatellite instability testing is the assay of mismatch repair markers. In various embodiments, the microsatellite markers are selected from the group consisting of BAT25, BAT26, D2S123, D5S346, and D17S250. In various embodiments, the mismatch repair markers are selected from the group consisting of MLH1, MSH2, MLH6, and PMS2. In various embodiments, the subject has one or more immune evasive, immunologically protected, and/or immunologically 'cold' tumors that are determined to be microsatellite instability low. In various embodiments, the subject has one or more immune evasive, immunologically protected, and/or immunologically 'cold' tumors that are determined to be microsatellite stable. In various embodiments, the subject has one or more immune evasive, immunologically protected, and/or immunologically 'cold' tumors that are mismatch repair proficient.

In various embodiments, the analysis of one or more tumor samples of a subject having one or more tumors characterized as immune evasive, immunologically protected, and/or immunologically 'cold' demonstrates increased levels of neutrophil extracellular traps (NETs). In various embodiments, the analysis of one or more tumor samples of a subject having one or more tumors characterized as immune evasive, immunologically protected, and/or immunologically 'cold' demonstrates increased levels of neutrophil extracellular traps (NETs) compared to the analysis of one or more tumor samples from one or more healthy subjects. In various embodiments, the levels of NETs in one or more tumor samples of a subject suffering from cancer are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tissue samples from one or more healthy subjects and/or subject suffering from cancer and responsive to treatment. In various embodiments, the levels of NETs in one or more tumor samples of a subject suffering from cancer are increased by 2-100 fold (e.g., increased relative to a healthy subject and/or a subject suffering from cancer and responsive to treatment by about 2, 5, 10, 15, 20, 25, 30, 35, 40, 45, 50, 55, 60, 65, 70, 75, 80, 85, 90, 95 fold, inclusive of all values and ranges between these values) compared to one or more tissue samples from one or more healthy subjects and/or subjects suffering from cancer and responsive to treatment. Several methods have been described in the literature for assaying NETs, including western blot, ELISA, and flow cytometry.

In various embodiments, the tumor characteristic of a subject suffering from cancer is determined from the analysis of nucleic acids in one or more tumor samples of the subject. In various embodiments, the tumor characteristic of a subject suffering from cancer is determined by comparing the analysis of nucleic acids in one or more tumor samples from the subject suffering from cancer to the analysis of one or more tissue samples from one or more healthy subjects and/or subjects suffering from cancer and responsive to treatment. In various embodiments, the nucleic acid is selected from the group comprising DNA, ssDNA, RNA, mRNA, dsRNA, siRNA, miRNA, and lncRNA. In various embodiments, the nucleic acid analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the analysis of nucleic acids from one or more tumor samples of a subject suffering from cancer is used to determine the tumor mutation burden. In various embodiments, the analysis of nucleic acids from one or more tumor samples of a subject having one or more tumors characterized as immune evasive, immunologically protected, and/or immunologically 'cold' demonstrates a low tumor mutation burden. In various embodiments, the analysis of nucleic acids from one or more tumor samples a subject having one or more tumors characterized as immune evasive, immunologically protected, and/or immunologically 'cold' demonstrates a tumor mutation burden of between 5 and 0.001 somatic mutations per mega base pairs (e.g., about 5, about 4, about 3, about 2, about 1, about 0.9, about 0.8, about 0.7, about 0.6, about 0.5, about 0.4, about 0.3, about 0.2, about 0.1, about 0.09, about 0.08, about 0.07, about 0.06, about 0.05, about 0.04, about 0.03, about 0.02, about 0.01, about 0.009, about 0.008, about 0.007, about 0.006, about 0.005, about 0.004, about 0.003, about 0.002, or 0.001, inclusive of all values and ranges between these values). In various embodiments, the nucleic acid analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the analysis of nucleic acids in one or more tumor samples of a subject having one or more tumors characterized as immune evasive, immunologically protected, and/or immunologically 'cold' demonstrates increased expression of genes associated with tumor promoting, tumor permissive, anti-inflammatory, and/or immune suppressive activity compared to the analysis of one or more tissue samples from one or more healthy subjects and/or subjects suffering from cancer and responsive to treatment. In various embodiments, genes associated with tumor promoting, tumor permissive, anti-inflammatory, and/ or immune suppressive activity are selected from the group consisting of CD39, CD47, CD79, CD140a, CD163, CD206, FOXP3, FAP, PD-1, PD-L1, PD-L2, CSF-1R, $A_1R$, $A_{2A}R$, $A_{2B}R$, and $A_3R$, TIM-1, TIM-3, TIM-4, TIGIT, CSFR, SIGLEC, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28, CXCL12, GM-CSF, G-CSF, FAP, TGF-β1, TGF-β2, and TGF-β3, arginase, asparaginase, kyneurinase, indoleamine 2,3 dioxygenase (IDO1 and IDO2), tryptophan 2,3 dioxygenase (TDO), myeloperoxidase (MPO), neutrophil elastase (NE), and IL4I1. In various embodiments, the expression of genes associated with tumor promoting, tumor permissive, anti-inflammatory, and/or immune suppressive activity is increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tissue samples of one or more healthy subjects and/or subjects suffering from cancer and responsive to treatment. In various embodiments, the gene expression analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the analysis of nucleic acids in one or more tumor samples of a subject having one or more tumors characterized as immune evasive, immunologically protected, and/or immunologically 'cold demonstrates low or decreased expression of genes associated with tumor inhibiting, anti-tumor, and/or pro-inflammatory activity. In various embodiments, the analysis of nucleic acids in one or more tumor samples of a subject suffering from cancer demonstrates no expression of genes associated with tumor inhibiting, anti-tumor, and/or pro-inflammatory activity. In various embodiments, genes associated with tumor inhibiting, anti-tumor, and/or pro-inflammatory activity are selected from the group consisting of CD44, CD56, CD103c, CD69, KG2A, NKG2B, NKG2C, NKG2D, NKG2E, NKG2F, NKG2H, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, cell-surface IL-15, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, CXCL2 (MCP-1), CXCL3 (MIP-1α), CXCL4 (MIP-1β), CXCL5 (RANTES), IFN-α, IFN-β, IFN-γ, Granzyme-B, Perforin, TNF-α, and p53. In various embodiments, the expression genes associated with tumor inhibiting, anti-tumor, and/or pro-inflammatory activity is decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50% compared to a healthy subject or a subject suffering from cancer responsive to treatment. In various embodiments, the gene expression analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, the disclosure provides a method of treating cancer in a subject comprising administering to the subject surface functionalized particles alone or in combination with a cancer therapeutic, wherein the subject has one or more tumors that are resistant and/or unresponsive to treatment. In various embodiments, the subject has one or more tumors that are resistant and/or unresponsive to one or more treatments selected from the group consisting of surgery, radiation, chemotherapy, biologic agents, small molecules, cell-based therapy, hormone therapy, and immunotherapy. In various embodiments, treatment is a standard of care therapy, first-line therapy, second-line therapy, and/or third-line therapy. In various embodiments, the subject has one or more tumors that have progressed during one or more treatments, wherein the treatments are standard of care therapy, first-line therapy, second-line therapy, and/or third-line therapy.

First-line therapy is defined as a treatment that is administered to a subject suffering from cancer who has not received any prior treatment. Second-line therapy is defined as treatment that is administered to a subject suffering from cancer who has received prior first-line therapy but experienced disease progression during first-line treatment. Third-line therapy is defined as treatment that is administered to a subject suffering from cancer who has received prior first and second-line treatment but has experienced disease progression during second-line treatment. Definitions of first, second, and third-line therapies are found on the National Cancer Institute's (NCI) Dictionary of Cancer Terms (https://www.cancer.gov/publications/dictionaries). Each particular type of cancer has a first-line, second-line, and third-line therapy. The first-, second-, and third-line therapies for a particular form of cancer or tumor type are known in the art. In addition, FDA approved drug labels will indicate if a particular drug is approved as a first-, second-, or third-line therapy.

Several criteria and definitions published in the literature can be used to determine the effect of one or more treatments on tumors in a subject suffering from cancer. Based on these criteria, tumors are defined as 'responsive', 'stable', or 'progressive' when they improve, remain the same, or worsen during the course of treatment, respectively. Examples of the most commonly used criteria published in the literature include Response Evaluation Criteria in Solid Tumors (RECIST), Modified Response Evaluation Criteria in Solid Tumors (mRECIST), PET Response Criteria in Solid Tumors (PERCIST), Choi Criteria, Lugano Response Criteria, European Association for the Study of the Liver (EASL) Criteria, Response Evaluation Criteria in the Cancer of the Liver (RECICL), and WHO Criteria in Tumor Response [30-32]

In various embodiments, the disclosure provides a method of treating cancer in a subject comprising administering to the subject surface functionalized particles alone or in combination with a cancer therapeutic, wherein the subject cannot tolerate standard of care therapy, first-line therapy, second-line therapy, and/or third-line therapy. In various embodiments, the disclosure provides a method of treating cancer in a subject comprising administering to the subject surface functionalized particles alone or in combination with a cancer therapeutic, wherein the subject has experienced tumor recurrence after surgical resection of the primary tumor. In various embodiments, the disclosure provides a method of treating cancer in a subject comprising administering to the subject surface functionalized particles alone or in combination with a cancer therapeutic, wherein the subject has a tumor that cannot be surgically removed. In various embodiments, the disclosure provides a method of treating cancer in a subject comprising administering to the subject surface functionalized particles alone or in combination with a cancer therapeutic, wherein the subject has no treatment options available.

Several therapies used in the treatment of cancer (e.g chemotherapies) are cytotoxic and are associated with significant side-effects and toxicities that are associated with poor outcomes and poor response to treatment. Prior to administering such treatments, clinicians rely on several assessment tools to help determine the risk of a subject suffering from cancer experiencing treatment related toxicities and adverse events. Based on the results of these assessments, a subject suffering from cancer is considered intolerant to therapy if they are determined to be at increased risk of experiencing therapy-related toxicities and adverse events resulting in poor outcomes. Examples of commonly used assessment tools used in the determination of therapy intolerance include Karnofsky Performance Status (KPS), Eastern Cooperative Oncology Group Performance Status (ECOG PS), Timed Get Up and Go (TUG), Short Physical Performance Battery (SPPB), Comprehensive Geriatric Assessment (CGA), Cancer Aging Research Group (CARG) Score, and Chemotherapy Risk Assessment Scale for High-Age Patients (CRASH) [33, 34].

Exemplary diseases, conditions or disorders that can be treated using the methods herein include cancers, such as esophageal cancer, pancreatic cancer, metastatic pancreatic cancer, metastatic adenocarcinoma of the pancreas, bladder cancer, stomach cancer, fibrotic cancer, glioma, malignant glioma, diffuse intrinsic pontine glioma, recurrent childhood brain neoplasm renal cell carcinoma, clear-cell metastatic renal cell carcinoma, kidney cancer, prostate cancer, metastatic castration resistant prostate cancer, stage IV prostate cancer, metastatic melanoma, melanoma, malignant melanoma, recurrent melanoma of the skin, melanoma brain metastases, stage IIIA skin melanoma; stage IIIB skin melanoma, stage IIIC skin melanoma; stage IV skin melanoma, malignant melanoma of head and neck, lung cancer, non small cell lung cancer (NSCLC), squamous cell non-small cell lung cancer, breast cancer, recurrent metastatic breast cancer, hepatocellular carcinoma, hodgkin's lymphoma, follicular lymphoma, non-hodgkin's lymphoma, advanced B-cell NHL, HL including diffuse large B-cell lymphoma (DLBCL), multiple myeloma, chronic myeloid leukemia, adult acute myeloid leukemia in remission; adult acute myeloid leukemia with Inv(16)(p13.1q22); CBFB-MYH11; adult acute myeloid leukemia with t(16;16)(p13.1;q22); CBFB-MYH11; adult acute myeloid leukemia with t(8;21)(q22;q22); RUNX1-RUNX1T1; adult acute myeloid leukemia with t(9;11)(p22;q23); MLLT3-MLL; adult acute promyelocytic leukemia with t(15;17)(q22;q12); PML-RARA; alkylating agent-related acute myeloid leukemia, chronic lymphocytic leukemia, richter's syndrome; waldenstrom macroglobulinemia, adult glioblastoma; adult gliosarcoma, recurrent glioblastoma, recurrent childhood rhabdomyosarcoma, recurrent ewing sarcoma/peripheral primitive neuroectodermal tumor, recurrent neuroblastoma; recurrent osteosarcoma, colorectal cancer, MSI positive colorectal cancer; MSI negative colorectal cancer, nasopharyngeal nonkeratinizing carcinoma; recurrent nasopharyngeal undifferentiated carcinoma, cervical adenocarcinoma; cervical adenosquamous carcinoma; cervical squamous cell carcinoma; recurrent cervical carcinoma; stage IVA cervical cancer; stage IVB cervical cancer, anal canal squamous cell carcinoma; metastatic anal canal carcinoma; recurrent anal canal carcinoma, recurrent head and neck cancer; carcinoma, squamous cell of head and neck, head and neck squamous cell carcinoma (HNSCC), ovarian carcinoma, colon cancer, gastric cancer, advanced GI cancer, gastric adenocarcinoma; gastroesophageal junction adenocarcinoma, bone neoplasms, soft tissue sarcoma; bone sarcoma, thymic carcinoma, urothelial carcinoma, recurrent merkel cell carcinoma; stage III merkel cell carcinoma; stage IV merkel cell carcinoma, myelodysplastic syndrome and recurrent mycosis fungoides and Sezary syndrome. In various embodiments, the cancers are selected from brain cancer, skin cancer, eye cancer, breast cancer, prostate cancer, lung cancer, esophageal cancer, head and neck cancer, cervical cancer, liver cancer, colon cancer, bone cancer, uterine cancer, ovarian cancer, bladder cancer, stomach cancer, oral cancer, thyroid cancer, kidney cancer, testicular cancer, leukemia, lymphoma and mesothelioma.

Non-limiting examples of cancers or tumors that are typically immunologically 'cold', immune evasive, immunologically protected, immunologically 'cold', microsatellite stable, microsatellite instability low, have a low immune infiltrate, have a low tumor mutational burden and/or exhibit heterogeneity include merkel cell carcinoma (MCC), renal cell carcinoma (RCC), ovarian cancer, MSS colorectal cancer, pancreatic cancer, gliobastoma, neuroblastoma, and prostate cancer.

Treatment Outcomes and Clinical Endpoints

In various embodiments, the disclosure provides a method of treating cancer in a subject comprising administering to the subject surface functionalized particles alone or in combination with a cancer therapeutic, wherein the subject has one or more immune evasive tumors. In various embodiments, the administering alters the tumor immune infiltrate. In various embodiments, the administering alters the anti-tumor immune response. In various embodiments, the administering alters the tumor microenvironment comprising tumor cells, immune cells, cancer stem cells, and stroma. In various embodiments, the administering transforms an immunologically cold tumor into an immunologically hot tumor. In various embodiments, the administering reduces tumor size and/or inhibits tumor growth. In various embodiments, the administering induces tumor cell death, apoptosis, and/or necrosis via direct particle uptake by tumor cells.

In various embodiments, the disclosure provides a method of treating cancer in a subject comprising administering to the subject surface functionalized particles alone or in combination with a cancer therapeutic, wherein the subject has one or more tumors that are characterized as immunologically protected and/or immune evasive. In various embodiments, the administering alters the tumor-associated stroma comprising fibroblasts, cancer-associated fibroblasts, adipocytes, pericytes, endothelium, vasculature, lymphatic vessels, tumor-associated vasculature, mesenchymal stromal cells, mesenchymal stem cells, and extracellular matrix.

It is contemplated that the methods herein reduce tumor size or tumor burden in the subject, and/or reduce metastasis in the subject. In various embodiments, the methods reduce the tumor size by 10%, 20%, 30% or more. In various embodiments, the methods reduce tumor size by 10%, 15%, 20%, 25%, 30%, 35%, 40%, 45%, 50%, 55%, 60%, 65%, 70%, 75%, 80%, 85%, 90%, 95% or 100%, or including all values and ranges that lie in between these values.

Certain biomarkers decrease in abundance when a tumor becomes immune-evasive. It is contemplated herein that after treatment with a surface functionalized particle described herein, optionally in combination with a cancer therapeutic, the level of one or more of biomarkers increases by an amount in the range of from about 1.1 fold to about 10 fold, e.g., about 1.1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 fold. Similarly, certain biomarkers increase in abundance when a tumor becomes immune evasive. After treatment with a surface functionalized particle described herein, the level of one or more of such biomarkers decrease by an amount in the range of from about 1.1 fold to about 10 fold, e.g., about 1.1, about 1.5, about 2, about 2.5, about 3, about 3.5, about 4, about 4.5, about 5, about 5.5, about 6, about 6.5, about 7, about 7.5, about 8, about 8.5, about 9, about 9.5, or about 10 fold. In various embodiments, administering surface functionalized particles, alone or in combination with a cancer therapeutic, to a subject having one or more tumors characterized as immune evasive, immunologically protected, and/or immunologically 'cold' reduces the levels of immune suppressive cells in blood. In various embodiments, the suppressive cells are myeloid derived suppressor cells (MDSCs), tumor-associated macrophages (TAMs), neutrophils, $T_{reg}$ cells, and $B_{reg}$ cells. In various embodiments, MDSCs are monocytic MDSCs (M-MDSCs) and polymorphonuclear MDSCs (PMN-MDSCs). In various embodiments, the TAMs are M2 TAMs. In various embodiments, the immune suppressive cells are CAFs. In various embodiments, the levels of immune suppressive cells are reduced by about 5-100% (e.g reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more blood samples collected from the subject prior to treatment. In various embodiments, the levels of immune suppressive cells are reduced by about 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment. In various embodiments, immune suppressive cells are identified by the assay of cell-surface proteins expression.

In various embodiments, administering surface functionalized particles, alone or in combination with a cancer therapeutic, to a subject having one or more tumors characterized as immune evasive, immunologically protected, and/or immunologically 'cold' increases the levels of activated pro-inflammatory immune cells by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more blood samples collected from the subject prior to treatment. In various embodiments, administering surface functionalized particles to a subject having one or more tumors characterized as immune evasive, immunologically protected, and/or immunologically 'cold' increases the levels of activated pro-inflammatory immune cells by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment. In various embodiments, the activated pro-inflammatory cells are dendritic cells (DCs), macrophages, M1 macrophages, T-cells, B-cells, NK cells, NK-T cells, and iNK cells. In various embodiments, the frequency of pro-inflammatory immune cells is increased to 10-50% (e.g., about 10%, 15%, 20%, 25%, 30%, 35%, 40%, 45%, or 50%, inclusive of all values and ranges between these values) of all leukocytes analyzed from one or more blood samples collected from the subject. In various embodiments, activated pro-inflammatory immune cells are identified by the assay of cell-surface protein expression.

In various embodiments, the analysis of cells in one or more blood samples of a subject suffering from cancer is performed by the assay of cell-surface proteins. In various embodiments, the cell-surface proteins are selected from the group consisting of receptor tyrosine kinase (RTK), CD1c, CD2, CD3, CD4, CD5, CD8, CD9, CD10, CD11b, CD11c, CD14, CD15, CD16, CD18, CD19, CD20, CD21, CD22, CD23, CD24, TACI, CD25, CD27, CD28, CD30, CD30L, CD31, CD32, CD32b, CD34, CD33, CD38, CD39, CD40, CD40-L, CD41b, CD42a, CD42b, CD43, CD44, CD45, CD47, CD45RA, CD45RO, CD48, CD52, CD55, CD56, CD58, CD61, CD66b, CD70, CD72, CD79, CD68, CD84, CD86, CD93, CD94, CD95, CRACC, BLAME, BCMA, CD103, CD107, CD112, CD120a, CD120b, CD123, CD125, CD134, CD135, CD140a, CD141, CD154, CD155, CD160, CD163, CD172a, XCR1, CD203c, CD204, CD206, CD207 CD226, CD244, CD267, CD268, CD269, CD355, CD358, NKG2A, NKG2B, NKG2C, NKG2D, NKG2E, NKG2F, NKG2H, KIR2DL1, KIR2DL2, KIR2DL3, KIR2DL5A, KIR2DL5B, KIR3DL1, KIR3DL2, KIR3DL3, KIR3DL4, KIR2DS1, KIR2DS2, KIR2DS3, KIR2DS4, KIR2DS5, DAP12, KIR3DS, NKp44, NKp46, TCR, BCR, Integrins, $Fc\beta_{\varepsilon}RI$, MHC-I, MHC-II, IL-1R, IL-2Rα, IL-2Rβ, IL-2Rγ, IL-3Rα, CSF2RB, IL-4R, IL-5Rα, CSF2RB, IL-6Rα, gp130, IL-7Rα, IL-9R, IL-12Rβ1, IL-12Rβ2, IL-13Rα1, IL-13Rα2, IL-15Rα, IL-21R, IL23R, IL-27Rα, IL-31Rα, OSMR, CSF-1R, cell-surface IL-15, IL-10Rα, IL-10Rβ, IL-20Rα, IL-20Rβ, IL-22Rα1, IL-22Rα2, IL-22Rβ, IL-28RA, PD-1, PD-1H, BTLA, CTLA-4, PD-L1, PD-L2, 2B4, B7-1, B7-2, B7-H1, B7-H4, B7-DC, DR3, LIGHT, LAIR, LTα1β2, LTβR, TIM-1, TIM-3, TIM-4, TIGIT, LAG-3, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CLECL9a, DC-SIGN, IGSF4A, SIGLEC, EGFR, PDGFR, VEGFR, FAP, α-SMA, Vimentin, Laminin, FAS, FAS-L, $F_C$, ICAM-1, ICAM-2, ICAM-3, ICAM-4, ICAM-5, PECAM-1, MICA, MICB, UL16, ULBP1, ULBP2, ILBP3, ULBP4, ULBP5, ULBP6, MULTI, RAE1 α, β, γ, δ, and ε, $A_1R$, $A_{2A}R$, $A_{2B}R$, and $A_3R$, H60a, H60b, and H60c. In various embodiments, Integrins are selected from the group consisting of α1, α2, αIIb, α3, α4, α5, α6, α7, α8, α9, α10, α11, αD, αE, αL, αM, αV, αX, β1, β2, β3, β4, β5, β6, β7, β8, and/or combinations thereof. In various embodiments, TCR is selected from the group consisting of α, β, γ, δ, ε, and ζ TCR. Several methods have been described in the literature for assaying of cell-surface protein expression, including Flow Cytometry and Mass Cytometry (CyTOF). The presence or abundance of one or more of these cell-surface proteins indicates that the patient is responsive to treatment with the method disclosed herein.

In various embodiments, administering surface functionalized particles, alone or in combination with a cancer therapeutic, to a subject having one or more tumors characterized as immune evasive, immunologically protected, and/or immunologically 'cold' reduces the neutrophil to lymphocyte (NLR) in one or more blood samples from high to moderate, or high to low. In various embodiments, the analysis of cells from one or more blood samples collected from a subject having one or more tumors characterized as immune evasive, immunologically protected, and/or immunologically 'cold' reduces NLR to between 1-2 (e.g., between 1, 1.1, 1.2, 1.3, 1.4, 1.5, 1.6, 1.7, 1.8, 1.9, and 2 inclusive of all values and ranges between these values). In various embodiments, NLR, after administration of surface functionalized particles is reduced. In various embodiments, NLR, after administration of surface functionalized particles is <2.

In various embodiments, administering surface functionalized particles, alone or in combination with a cancer therapeutic, to a subject having one or more tumors characterized as immune evasive, immunologically protected, and/or immunologically 'cold' reduces the levels of CTCs in one or blood samples. In various embodiments, the levels of CTCs in blood are reduced to ≤5, ≤4, ≤3, ≤2, ≤1, or 0 per 7.5 mL blood inclusive of inclusive of all values and ranges between these values.

In various embodiments, administering surface functionalized particles, alone or in combination with a cancer therapeutic, to a subject having one or more tumors characterized as immune evasive, immunologically protected, and/or immunologically 'cold' decreases the levels of tumor promoting, anti-inflammatory, and/or immune suppressive proteins in one or more blood samples of the subject. In various embodiments, the tumor promoting, anti-inflammatory, and/or immune suppressive proteins are selected from the group consisting of CD39, CD79, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28, CXCL12, GM-CSF, G-CSF, TGF-β1, TGF-β2, and TGF-β3, arginase, asparaginase, kyneurinase, indoleamine 2,3 dioxygenase (IDO1 and IDO2), tryptophan 2,3 dioxygenase (TDO), myeloperoxidase (MPO), neutrophil elastase (NE), and IL4I1. In various embodiments, the levels of tumor promoting, anti-inflammatory, and/or immune suppressive proteins in one or more blood samples of the subject are decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected prior to treatment. In various embodiments, the levels of tumor promoting, anti-inflammatory, and/or immune suppressive proteins in one or more blood samples of the subject are decreased by 2-100 fold (e.g., decreased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment.

In various embodiments, administering surface functionalized particles, alone or in combination with a cancer therapeutic, to a subject having one or more tumors characterized as immune evasive, immunologically protected, and/or immunologically 'cold' increases the levels of tumor inhibiting, anti-tumor, and/or pro-inflammatory proteins in one or more blood samples collected from the subject. In various embodiments, tumor inhibiting, anti-tumor, and/or pro-inflammatory proteins are selected from the group consisting of IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, cell-surface IL-15, CXCL2 (MCP-1), CXCL3 (MIP-1α), CXCL4 (MIP-1β), CXCL5 (RANTES), IFN-α, IFN-β, IFN-γ, Granzyme-B, Perforin, and TNF-α. In various embodiments, the levels of anti-tumor, and/or pro-inflammatory proteins are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected prior to treatment. In various embodiments, the levels of anti-tumor, and/or pro-inflammatory proteins are increased by 2-100 fold (e.g., increased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment. Several methods have been described in the literature for assaying proteins from blood samples, including western blot, and ELISA.

In various embodiments, administering surface functionalized particles, alone or in combination with a cancer therapeutic, to a subject having one or more tumors characterized as immune evasive, immunologically protected, and/or immunologically 'cold' decreases the levels of neutrophil extracellular traps (NETs) in one or more blood samples collected from the subject. In various embodiments, the levels of NETs in one or more blood samples is decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected prior to treatment. In various embodiments, the levels of NETs in one or more blood samples is decreased by 2-100-fold (e.g., by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment. Several methods have been described in the literature for assaying NETs from blood samples, including western blot, ELISA, and flow cytometry.

In various embodiments, administering surface functionalized particles, alone or in combination with a cancer therapeutic, to a subject having one or more tumors characterized as immune evasive, immunologically protected, and/or immunologically 'cold' decreases the expression of tumor promoting, tumor permissive, and/or immune suppressive genes in one or more blood samples of the subject. In one or more embodiments, the expression of tumor promoting, tumor permissive, and/or immune suppressive genes is decreased by 5-100% (e.g., decreased relative to levels in one or more blood samples collected prior to treatment by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100%) compared to one or more blood samples collected prior to treatment. In one or more embodiments, the expression of tumor promoting, tumor permissive, and/or immune suppressive genes is decreased by 2-100-fold (e.g., decreased by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment.

In various embodiments, administering surface functionalized particles, alone or in combination with a cancer therapeutic, to a subject having one or more tumors characterized as immune evasive, immunologically protected, and/or immunologically 'cold' increases the expression of tumor inhibiting, anti-tumor, and/or pro-inflammatory genes in one or more samples collected from the subject. In one or more embodiments, the expression of tumor inhibiting, anti-tumor, and/or pro-inflammatory genes is increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more blood samples collected prior to treatment. In various embodiments, the expression of tumor inhibiting, anti-tumor, and/or pro-inflammatory genes is increased by 2-100-fold (e.g., increased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more blood samples collected from the subject prior to treatment. In various embodiments, the gene expression analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, administering surface functionalized particles, alone or in combination with a cancer therapeutic, to a subject having one or more tumors characterized as immune evasive, immunologically protected, and/or immunologically 'cold' increases the levels of leukocytes in the tumor. In various embodiments, the levels of leukocytes are increased in the tumor core and/or tumor periphery. In various embodiments, the leukocytes are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more tumor samples collected from the subject prior to treatment. In various embodiments, the levels of leukocytes are increased by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. In various embodiments, the frequency of leukocytes in the tumor core and/or tumor periphery is ≥5%, ≥10%, ≥15%, ≥20%, ≥25%, ≥30%, ≥35%, ≥40%, ≥45%, or ≥50, inclusive of all values and ranges between these values, of all cells analyzed.

In various embodiments, administering surface functionalized particles, alone or in combination with a cancer therapeutic, to a subject having one or more tumors characterized as immune evasive, immunologically protected, and/or immunologically 'cold' reduces the levels of immune suppressive cells in the tumor. In various embodiments, the levels of immune suppressive cells are reduced in the tumor core and/or tumor periphery. In various embodiments, the suppressive cells are myeloid derived suppressor cells (MDSCs), tumor-associated macrophages (TAMs), neutrophils, $T_{reg}$ cells, and $B_{reg}$ cells. In various embodiments, MDSCs are monocytic MDSCs (M-MDSCs) and polymorphonuclear MDSCs (PMN-MDSCs). In various embodiments, the TAMs are M2 TAMs. In various embodiments, the immune suppressive cells are CAFs. In various embodiments, the levels of immune suppressive cells are reduced by about 5-100% (e.g reduced by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more tumor samples collected from the subject prior to treatment. In various embodiments, the levels of immune suppressive cells are reduced by about 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. In various embodiments, immune suppressive cells are identified by the assay of cell-surface proteins expression. Levels of leukocytes in a tumor sample can be evaluated by several methods including flow cytometry and immunohistochemistry.

In various embodiments, administering surface functionalized particles, alone or in combination with a cancer therapeutic, to a subject having one or more tumors characterized as immune evasive, immunologically protected, and/or immunologically 'cold' increases the levels of activated pro-inflammatory immune cells in the tumor. In various embodiments, the levels of activated pro-inflammatory cells are increased in the tumor core and/or tumor periphery.

In various embodiments, administering surface functionalized particles, alone or in combination with a cancer therapeutic, to a subject having one or more tumors characterized as immune evasive, immunologically protected, and/or immunologically 'cold' increases the levels of activated pro-inflammatory immune cells in the tumor by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, or 50% compared to one or more tumor samples collected from the subject prior to treatment. In various embodiments, administering surface functionalized particles to a subject having one or more tumors characterized as immune evasive, immunologically protected, and/or immunologically 'cold' increases the levels of activated pro-inflammatory immune cells by 2-100 fold (e.g., about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. In various embodiments, the activated pro-inflammatory cells are dendritic cells (DCs), macrophages, M1 macrophages, T-cells, B-cells, NK cells, NK-T cells, and iNK cells. In various embodiments, the frequency of pro-inflammatory immune cells is between about 10-50% (e.g., about 10%, 15%, 20%, 25%, 30%, 35%, 40%, 45%, or 50%, inclusive of all values and ranges between these values) of all leukocytes analyzed from one or more tumor samples collected from the subject. In various embodiments, activated pro-inflammatory immune cells are identified by the assay of cell-surface protein expression.

In various embodiments, the analysis of cells in one or more tumor samples of a subject suffering from cancer is performed by the assay of cell-surface proteins. In various embodiments, the cell-surface proteins are selected from the group consisting of receptor tyrosine kinase (RTK), CD1c, CD2, CD3, CD4, CD5, CD8, CD9, CD10, CD11b, CD11c, CD14, CD15, CD16, CD18, CD19, CD20, CD21, CD22, CD23, CD24, TACI, CD25, CD27, CD28, CD30, CD30L, CD31, CD32, CD32b, CD34, CD33, CD38, CD39, CD40, CD40-L, CD41b, CD42a, CD42b, CD43, CD44, CD45, CD47, CD45RA, CD45RO, CD48, CD52, CD55, CD56, CD58, CD61, CD66b, CD70, CD72, CD79, CD68, CD84, CD86, CD93, CD94, CD95, CRACC, BLAME, BCMA, CD103, CD107, CD112, CD120a, CD120b, CD123, CD125, CD134, CD135, CD140a, CD141, CD154, CD155, CD160, CD163, CD172a, XCR1, CD203c, CD204, CD206, CD207 CD226, CD244, CD267, CD268, CD269, CD355, CD358, NKG2A, NKG2B, NKG2C, NKG2D, NKG2E, NKG2F, NKG2H, KIR2DL1, KIR2DL2, KIR2DL3, KIR2DL5A, KIR2DL5B, KIR3DL1, KIR3DL2, KIR3DL3, KIR3DL4, KIR2DS1, KIR2DS2, KIR2DS3, KIR2DS4, KIR2DS5, DAP12, KIR3DS, NKp44, NKp46, TCR, BCR, Integrins, FcβεRI, MHC-I, MHC-II, IL-1R, IL-2Rα, IL-2Rβ, IL-2Rγ, IL-3Rα, CSF2RB, IL-4R, IL-5Rα, CSF2RB, IL-6Rα, gp130, IL-7Rα, IL-9R, IL-12Rβ1, IL-12Rβ2, IL-13Rα1, IL-13Rα2, IL-15Rα, IL-21R, IL23R, IL-27Rα, IL-31Rα, OSMR, CSF-1R, cell-surface IL-15, IL-10Rα, IL-10Rβ, IL-20Rα, IL-20Rβ, IL-22Rα1, IL-22Rα2, IL-22Rβ, IL-28RA, PD-1, PD-1H, BTLA, CTLA-4, PD-L1, PD-L2, 2B4, B7-1, B7-2, B7-H1, B7-H4, B7-DC, DR3, LIGHT, LAIR, LTα1β2, LTβR, TIM-1, TIM-3, TIM-4, TIGIT, LAG-3, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, CCR1, CCR2, CCR3, CCR4, CCR5, CCR6, CCR7, CCR8, CCR9, CCR10, CCR11, CXCR1, CXCR2, CXCR3, CXCR4, CXCR5, CXCR6, CXCR7, CLECL9a, DC-SIGN, IGSF4A, SIGLEC, EGFR, PDGFR, VEGFR, FAP, α-SMA, Vimentin, Laminin, FAS, FAS-L, $F_C$, ICAM-1, ICAM-2, ICAM-3, ICAM-4, ICAM-5, PECAM-1, MICA, MICB, UL16, ULBP1, ULBP2, ILBP3, ULBP4, ULBP5, ULBP6, MULTI, RAE1 α, β, γ, δ, and ε, $A_1R$, $A_{2A}R$, $A_{2B}R$, and $A_3R$, H60a, H60b, and H60c. In various embodiments, Integrins are selected from the group consisting of α1, α2, αIIb, α3, α4, α5, α6, α7, α8, α9, α10, α11, αD, αE, αL, αM, αV, αX, β1, β2, β3, β4, β5, β6, β7, β8, and/or combinations thereof. In various embodiments, TCR is selected from the group consisting of α, β, γ, δ, ε, and ζ TCR. Several methods have been described in the literature for assaying of cell-surface protein expression, including Flow Cytometry and Mass Cytometry (CyTOF). The presence or abundance of one or more of these cell-surface proteins indicates that the patient is responsive to treatment with the method disclosed herein.

In various embodiments, administering surface functionalized particles, alone or in combination with a cancer therapeutic, to a subject having one or more tumors characterized as immune evasive, immunologically protected, and/or immunologically 'cold' decreases the levels of tumor promoting, anti-inflammatory, and/or immune suppressive proteins in one or more tumor samples of the subject. In various embodiments, the tumor promoting, anti-inflammatory, and/or immune suppressive proteins are selected from the group consisting of CD39, CD79, MMP1, MMP2, MMP3, MMP7, MMP8, MMP9, MMP10, MMP11, MMP12, MMP13, MMP14, MMP15, MMP16, MMP17, MMP18, MMP19, MMP20, MMP21, MMP23A, MMP23B, MMP24, MMP25, MMP26, MMP27 and MMP28, CXCL12, GM-CSF, G-CSF, TGF-β1, TGF-β2, and TGF-β3, arginase, asparaginase, kyneurinase, indoleamine 2,3 dioxygenase (IDO1 and IDO2), tryptophan 2,3 dioxygenase (TDO), myeloperoxidase (MPO), neutrophil elastase (NE), and IL4I1. In various embodiments, the levels of tumor promoting, anti-inflammatory, and/or immune suppressive proteins in one or more tumor samples of the subject are decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tumor samples collected prior to treatment. In various embodiments, the levels of tumor promoting, anti-inflammatory, and/or immune suppressive proteins in one or more tumor samples of the subject are decreased by 2-100 fold (e.g., decreased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment.

In various embodiments, administering surface functionalized particles, alone or in combination with a cancer therapeutic, to a subject having one or more tumors characterized as immune evasive, immunologically protected, and/or immunologically 'cold' increases the levels of proteins associated with tumor growth inhibition, anti-tumor activity, and/or pro-inflammatory activity. In various embodiments, proteins associated with tumor growth inhibition, anti-tumor activity, and/or pro-inflammatory activity are selected from the group consisting of CD44, CD56, CD103c, CD69, KG2A, NKG2B, NKG2C, NKG2D, NKG2E, NKG2F, NKG2H, ICOS, ICOS-L, SLAM, SLAMF2, OX-40, OX-40L, GITR, GITRL, TL1A, HVEM, 41-BB, 41BB-L, TL-1A, TRAF1, TRAF2, TRAF3, TRAF5, BAFF, BAFF-R, APRIL, TRAIL, RANK, AITR, TRAMP, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-17, IL-18, IL-20, IL-21, IL-22, IL-23, IL-24, IL-25, IL-26, IL-27, IL-28, IL-29, IL-30, IL-31, IL-32, IL-33, IL-35, IL-36, CXCL2 (MCP-1), CXCL3 (MIP-1α), CXCL4 (MIP-1β), CXCL5 (RANTES), IFN-α, IFN-β, IFN-γ, Granzyme-B, Perforin, and TNF-α. In various embodiments, the levels of proteins associated with tumor growth inhibition, anti-tumor activity, and/or pro-inflammatory activity are increased by 5-100% (e.g., increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tumor samples collected prior to treatment. In various embodiments, the levels of proteins associated with tumor growth inhibition, anti-tumor activity, and/or pro-inflammatory activity are increased by 2-100 fold (e.g., decreased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. Several methods have been described in the literature for assaying proteins from tumor samples, including western blot, and ELISA.

In various embodiments, administering surface functionalized particles, alone or in combination with a cancer therapeutic, to a subject having one or more tumors characterized as immune evasive, immunologically protected, and/or immunologically 'cold' decreases the levels of neutrophil extracellular traps (NETs) in one or more tumor samples collected from the subject. In various embodiments, the levels of NETs in one or more tumor samples is decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tumor samples collected prior to treatment. In various embodiments, the levels of NETs in one or more tumor samples is decreased by 2-100-fold (e.g., decreased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. Several methods have been described in the literature for assaying NETs from tumor samples, including western blot, ELISA, and flow cytometry.

In various embodiments, administering surface functionalized particles, alone or in combination with a cancer therapeutic, to a subject having one or more tumors characterized as immune evasive, immunologically protected, and/or immunologically 'cold' decreases the expression of tumor promoting, tumor permissive, and/or immune suppressive genes in one or more tumor samples of the subject. In one or more embodiments, the expression of tumor promoting, tumor permissive, and/or immune suppressive genes is decreased by 5-100% (e.g., decreased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tumor samples collected prior to treatment. In one or more embodiments, the expression of tumor promoting, tumor permissive, and/or immune suppressive genes is decreased by 2-100-fold (e.g., decreased relative to one or more samples collected prior to treatment by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment.

In various embodiments, administering surface functionalized particles, alone or in combination with a cancer therapeutic, to a subject having one or more tumors characterized as immune evasive, immunologically protected, and/or immunologically 'cold' increases the expression of tumor inhibiting, anti-tumor, and/or pro-inflammatory genes in one or more samples collected from the subject. In one or more embodiments, the expression of tumor inhibiting, anti-tumor, and/or pro-inflammatory genes is increased by 5-100% (e.g increased by about 5%, about 10%, about 15%, about 20%, about 25%, about 30%, about 35%, about 40%, about 45%, about 50%, about 55%, about 60%, about 65%, about 70%, about 75%, about 80%, about 85%, about 90%, about 95%, or about 100%, inclusive of all values and ranges between these values), 10-95%, 15-90%, 20-85%, 25-75%, 30-70%, 35-65%, 40-60%, 45-55%, 50%, or 100% compared to one or more tumor samples collected prior to treatment. In various embodiments, the expression of tumor inhibiting, anti-tumor, and/or pro-inflammatory genes is increased by 2-100-fold (e.g., increased by about 2, 5, 10, 15, 20, 25, 30, 35, 40, 45, 50, 55, 60, 65, 70, 75, 80, 85, 90, 95, or 100 fold, inclusive of all values and ranges between these values) compared to one or more tumor samples collected from the subject prior to treatment. In various embodiments, the gene expression analysis is performed by PCR, RT-PCR, qRT-PCR, next-generation sequencing (NGS), RNA-seq, ATAC-seq, exome sequencing, Southern Blot, microarray analysis, and/or single-cell sequencing.

In various embodiments, treatment of a subject having cancer with a surface functionalized particle alone or in combination with a cancer therapeutic switches the cold tumor to a hot tumor. Such switch can be detected using the methods described herein and known in the art. If the subject has been diagnosed with a tumor that has switched from cold to hot tumor, treatment may continue by administering a surface functionalized particle alone or in combination with a cancer therapeutic, wherein the cancer therapeutic is useful in treating hot tumors, or tumors that are immune cell rich or immunogenic. In other embodiments, when the tumor has switched from cold to hot tumor, the patient stops treatment with the surface functionalized particle, and the patient begins treatment with a cancer therapeutic that is useful in treating hot tumors, or tumors that are immune cell rich or immunogenic. Such cancer therapeutics include chemotherapeutics, cytokines, angiogenesis inhibitors, enzymes, immune checkpoint modulators and monoclonal antibodies, hormone therapy, comprises one or more cell-based therapies, such as adoptive cell transfer, tumor-infiltrating leukocyte therapy, chimeric antigen receptor T-cell therapy (CAR-T), NK-cell therapy and stem cell therapy, or oncolytic virus or oncolytic bacteria.

In various embodiments, the immune checkpoint modulators target Programmed cell death protein 1 (PD1), Programmed cell death protein ligand-1 (PD-L1), cytotoxic T-lymphocyte-associated protein 4 (CTLA-4), T-cell Immunoglobulin and mucin-domain containing-3 (TIM-3), Lymphocyte-activation Gene 3 (LAG-3) and/or TIGIT (T cell immunoreceptor with Ig and ITIM domains). In various embodiments, the immune checkpoint modulator is an antibody selected from the group consisting of ipilimumab, tremelimumab, pembrolizumab, nivolumab, atezolizumab, avelumab, cemiplimab and durvalumab.

In various embodiments, the subject diagnosed with a cold tumor and receiving therapy with a surface functionalized particle alone or in combination with a cancer therapeutic is monitored regularly to determine if the tumor has switched to a hot tumor. Monitoring may be carried out as determined by a physician to be necessary, e.g., every month, every two months, every three months, every 6 months, or every year.

In various embodiments, the subject has previously been treated with immunotherapy but has developed resistance to immunotherapy, or had a shift from a hot tumor to a cold tumor. Also provided is a method of treating a subject having cancer that has developed resistance to immunotherapy or developed a cold tumor comprising administering to the subject a surface functionalized particle alone or in combination with a cancer therapeutic.

Administration and Dosing

Contemplated herein are methods comprising administering a composition comprising a negatively charged particle as described herein in combination with a cancer therapeutic to treat a subject suffering from cancer.

Methods of the disclosure are performed using any medically-accepted means for introducing a therapeutic directly or indirectly into a mammalian subject, including but not limited to injections, oral ingestion, intranasal, topical, transdermal, parenteral, inhalation spray, vaginal, or rectal administration. The term parenteral as used herein includes subcutaneous, intravenous, intramuscular, intraarticular, intraperitoneal, intrathecal and intracisternal injections, as well as catheter or infusion techniques. In various embodiments, the particle is administered intravenously, but may be administered through other routes of administration such as, but not limited to: intradermal, subcutaneous, epictuaneous, oral, intra-articular, and intrathecal. In various embodiments, the compositions are administered at the site of the tumor.

In various embodiments, the surface functionalized particle is administered at a dose from about 0.1 to about 24 mg/kg. In various embodiments, the particle is administered at a dose of about 0.1 mg/kg, 0.5 mg/kg, 1.0 mg/kg, 2.0 mg/kg, 3.0 mg/kg, 4.0 mg/kg, 5.0 mg/kg, 6.0 mg/kg, 7.0 mg/kg, 8.0 mg/kg, 9.0 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, or 24 mg/kg including all values and ranges between these values. In various embodiments, the particle is administered at a dose ranging from about 8.0 mg to about 1920 mg. In various embodiments, the particle is administered at a dose of about 8.0 mg, 80 mg, 320 mg, 640 mg, 800 mg, 960 mg, 1120 mg, 1280 mg, 1440 mg, 1600 mg, 1760 mg, or 1920 mg. Also contemplated are values within and between the recited dose endpoints. These concentrations may be administered as a single dosage form or as multiple doses.

It is contemplated that the cancer therapeutic, if a known cancer therapeutic, is administered as directed by the manufacturer and the treating physician. If the particle and cancer therapeutic are to be administered in the same formulation, they can be formulated as described herein.

The amounts of immune modulator or biologic agent cancer therapeutic in a given dosage may vary according to the size of the individual to whom the therapy is being administered as well as the characteristics of the disorder being treated. In exemplary treatments, it may be necessary to administer about 1 mg/day, 5 mg/day, 10 mg/day, 20 mg/day, 50 mg/day, 75 mg/day, 100 mg/day, 150 mg/day, 200 mg/day, 250 mg/day, 500 mg/day or 1000 mg/day, including all values and ranges between these values. Standard dose-response studies, first in animal models and then in clinical testing, reveals optimal dosages for particular disease states and patient populations.

The conditions treatable by methods of the present disclosure preferably occur in mammals. Mammals include, for example, humans and other primates, as well as pet or companion animals such as dogs and cats, laboratory animals such as rats, mice and rabbits, and farm animals such as horses, pigs, sheep, and cattle. In various embodiments, the subject is human.

In various embodiments, the particle is administered daily, every other day, twice daily, three times per day, seven times per week, six times per week, five times per week, four times per week, three times per week, twice weekly, once weekly, once every two weeks, once every three weeks, once every 4 weeks, once every two months, once every three months, once every 6 months or once per year.

The disclosure further contemplates a sterile pharmaceutical composition comprising a particle as described herein, a cancer therapeutic and a pharmaceutically acceptable carrier.

The disclosure further contemplates a sterile pharmaceutical composition comprising a separate a particle as described herein and a pharmaceutically acceptable carrier.

The disclosure further contemplates a sterile pharmaceutical composition comprising a separate cancer therapeutic and a pharmaceutically acceptable carrier.

Syringes, e.g., single use or pre-filled syringes, sterile sealed containers, e.g. vials, bottle, vessel, and/or kits or packages comprising any of the foregoing antibodies or compositions, optionally with suitable instructions for use, are also contemplated.

Combination Therapy

It is contemplated that the particle described herein is administered in combination with a cancer therapeutic to treat cancer of a proliferative disorder. In various embodiments, the cancer therapeutic is a chemotherapeutic, a biologic agent, a cell-based therapy, a hormone therapy, an antibody-drug conjugate, oncolytic virus, or a cancer vaccine.

Hormone therapies include Tamoxifen for breast cancer, Zoladex for breast cancer and prostate cancer, Aromatase inhibitors (e.g anastrazole, letrozole, exemestane). Antibody drug conjugates include Brentuximab vedotin for lymphomas. (anti-CD30 mAB+monomethyl auristatin E), Ado-trastuzumab entansine for breast cancers. (anti-Her2/Neu+maytansinoid) and Inotuzumab Ozagamicin for ALL (anti-CD22+calicheamicin). Oncolytic viruses include Imlygic (Amgen®). Cancer vaccines include Sipuleucel-T for prostate cancer. Several cancer vaccines are in development and include, but are not limited to, proteins, polypeptides, and nucleic acid vaccines.

In various embodiments, the cancer therapeutic is a chemotherapeutic selected from the group consisting of growth inhibitors, a cytotoxic agent, DNA-replication inhibitors, kinase inhibitors, signaling cascade inhibitors, angiogenesis inhibitors, metabolic inhibitors, amino acid synthesis inhibitors, selective inhibitors of oncogenic proteins, inhibitors of metastasis, inhibitors of anti-apoptosis factors, apoptosis inducers, nucleoside signaling inhibitors, enzyme inhibitors and DNA-damaging agents.

A cytotoxic agent refers to a substance that inhibits or prevents the function of cells and/or causes destruction of cells. The term is intended to include radioactive isotopes (e.g., I131, I125, Y90 and Re186), chemotherapeutic agents, and toxins such as enzymatically active toxins of bacterial, fungal, plant or animal origin or synthetic toxins, or fragments thereof. A non-cytotoxic agent refers to a substance that does not inhibit or prevent the function of cells and/or does not cause destruction of cells. A non-cytotoxic agent may include an agent that can be activated to be cytotoxic.

Chemotherapeutic agents contemplated for use in the methods of the present disclosure include, but are not limited to those listed in Table I:

TABLE I

| Alkylating agents |
|---|
| **Nitrogen mustards** |
| mechlorethamine |
| cyclophosphamide |
| ifosfamide |
| melphalan |
| chlorambucil |
| **Nitrosoureas** |
| carmustine (BCNU) |
| lomustine (CCNU) |
| semustine (methyl-CCNU) |
| **Ethylenimine/Methyl-melamine** |
| thriethylenemelamine (TEM) |
| triethylene thiophosphoramide (thiotepa) |
| hexamethylmelamine (HMM, altretamine) |
| **Alkyl sulfonates** |
| busulfan |
| **Triazines** |
| dacarbazine (DTIC) |
| **Antimetabolites** |
| Folic Acid analogs |
| methotrexate |
| Trimetrexate |
| Pemetrexed (Multi-targeted antifolate) |
| **Pyrimidine analogs** |
| 5-fluorouracil |
| fluorodeoxyuridine |
| gemcitabine |
| cytosine arabinoside (AraC, cytarabine) |
| 5-azacytidine |
| 2,2'- difluorodeoxy-cytidine |
| **Purine analogs** |
| 6-mercaptopurine |
| 6-thioguanine |
| azathioprine |
| 2'-deoxycoformycin (pentostatin) |
| erythrohydroxynonyl-adenine (EHNA) |
| fludarabine phosphate |
| 2-chlorodeoxyadenosine (cladribine, 2-CdA) |
| **Type I Topoisomerase Inhibitors** |
| camptothecin |
| topotecan |
| irinotecan |
| **Biological response modifiers** |
| G-CSF |
| GM-CSF |
| **Differentiation Agents** |
| retinoic acid derivatives |

TABLE I-continued

| Hormones and antagonists |
|---|
| **Adrenocorticosteroids/antagonists** |
| prednisone and equiv-alents |
| dexamethasone |
| ainoglutethimide |
| **Progestins** |
| hydroxyprogesterone caproate |
| medroxyprogesterone acetate |
| megestrol acetate |
| **Estrogens** |
| diethylstilbestrol |
| ethynyl estradiol/equivalents |
| **Antiestrogen** |
| tamoxifen |
| **Androgens** |
| testosterone propionate |
| fluoxymesterone/equivalents |
| **Antiandrogens** |
| flutamide |
| gonadotropin-releasing hormone analogs |
| leuprolide |
| **Nonsteroidal antiandrogens** |
| flutamide |
| **Natural products** |
| Antimitotic drugs |
| Taxanes |
| paclitaxel |
| Vinca alkaloids |
| vinblastine (VLB) |
| vincristine |
| vinorelbine |
| Taxotere ® (docetaxel) |
| estramustine |
| estramustine phosphate |
| **Epipodophylotoxins** |
| etoposide |
| teniposide |
| **Antibiotics** |
| actimomycin D |
| daunomycin (rubido-mycin) |
| doxorubicin (adria-mycin) |
| mitoxantroneidarubicin |
| bleomycin |
| splicamycin (mithramycin) |
| mitomycinC |
| dactinomycin |
| aphidicolin |
| **Enzymes** |
| L-asparaginase |
| L-arginase |
| **Radiosensitizers** |
| metronidazole |
| misonidazole |
| desmethylmisonidazole |
| pimonidazole |
| etanidazole |
| nimorazole |
| RSU 1069 |
| EO9 |
| RB 6145 |
| SR4233 |
| nicotinamide |
| 5-bromodeozyuridine |
| 5-iododeoxyuridine |
| bromodeoxycytidine |

TABLE I-continued

| Miscellaneous agents |
|---|
| Platinium coordination complexes |
| cisplatin |
| Carboplatin |
| oxaliplatin |
| Anthracenedione |
| mitoxantrone |
| Substituted urea |
| hydroxyurea |
| Methylhydrazine derivatives |
| N-methylhydrazine (MIH) |
| procarbazine |
| Adrenocortical suppressant |
| mitotane (o, p'- DDD) |
| ainoglutethimide |
| Cytokines |
| interferon (α, β, γ) |
| interleukin-2 |
| Photosensitizers |
| hematoporphyrin derivatives |
| Photofrin ® |
| benzoporphyrin derivatives |
| Npe6 |
| tin etioporphyrin (SnET2) |
| pheoboride-a |
| bacteriochlorophyll-a |
| naphthalocyanines |
| phthalocyanines |
| zinc phthalocyanines |
| Radiation |
| X-ray |
| ultraviolet light |
| gamma radiation |
| visible light |
| infrared radiation |
| microwave radiation |

It is also contemplated that the cancer therapeutic comprises one or more biologic agents, such as cytokines, angiogenesis inhibitors, immune checkpoint modulators and monoclonal antibodies.

Cytokines include interferons (IFN) and interleukins (ILs), such as IFN-alpha, IFN-beta, IFN-gamma, IL-1, IL-2, IL-4, IL-5, IL-6, IL-7, IL-10, IL-11, IL-12, IL-13, IL-15, IL-17, IL-18, IL-21, members of the transforming growth factor beta superfamily, including TGF-β1, TGF-β2 and TGF-β3, tumor necrosis factor alpha, Granulocyte colony-stimulating factor (G-CSF), and Granulocyte macrophage colony-stimulating factor (GM-CSF).

In various embodiments, the cancer therapeutic comprises an enzyme. In various embodiments, the cancer therapeutic comprises an enzyme that targets T-cells, B-cells, APCs, monocytes, MDSCs, TAMs, neutrophils, other monocyte-derived cells, tumor-associated stroma, cancer stem cells, mesenchymal stem cells, extracellular matrix, and amino acids. In various embodiments, the cancer therapeutic comprises an enzyme selected from the group comprising asparaginase, kynurininase, L-arginine deiminase, L-methionine-γ-lyase, one or more amino acid degrading enzymes, and one or more nucleoside degrading enzymes.

Biologic agents such as immune checkpoint modulators target PD1, PD-L1, CTLA-4, TIMP-3, LAG-3 and/or TIGIT (T cell immunoreceptor with Ig and ITIM domains). In various embodiments, the immune checkpoint modulators are antibodies specific for PD-1, PD-L1, or CTLA-4. Antibodies specific for checkpoint proteins include ipilimumab (YERVOY®, Bristol-Myers Squibb Company), and tremelimumab that bind CTLA-4; antibodies to PD-1 such as Pembrolizumab (KEYTRUDA®, Merck Sharp & Dohme Corp) and nivolumab (OPDIVO®, Bristol-Myers Squibb); and antibodies that target PD-L1 such as Atezolizumab (TECENTRIQ®), Avelumab (BAVENCIO®), and Durvalumab (IMFINI®) (approved for treatment of urothelial carcinoma and non-small cell lung carcinoma), Cemiplimab (LIBTAYO®) (approved for cutaneous squamous cell carcinoma).

In various embodiments the monoclonal antibodies are mono-specific, bi-specific, tri-specific or bispecific T-cell engaging (BiTE) antibodies.

In various embodiments the monoclonal antibodies are immune cell co-stimulatory molecule agonists that induce an anti-tumor immune response. Exemplary co-stimulatory molecules include, but are not limited to, ICOS (Inducible T cell Co-stimulator) (CD278), OX40 (CD134), GITR (Glucocorticoid-induced Tumor Necrosis Factor Receptor), CD40 and CD27.

In various embodiments, monoclonal antibodies useful in the methods are selected from the group comprising Alemtuzumab, Bevacizumab, Brentuximab, Cetuximab, Denosumab, Ibritumomab, Trastuzumab, Panitumumab, Pertuzumab, and Rituximab. In various embodiments, monoclonal antibodies useful in the methods target receptor tyrosine kinase, EGFR, VEGF, VEGFR, PDGF, PDGFR, TGF-β, TGF-β-LAP, SIRP-α, CD47, CD39, CD73, and fibroblast activating protein (FAP).

Biologic agents include monoclonal antibodies that are mono-specific, bi-specific, tri-specific or bispecific T-cell engagers (BiTE). Monoclonal antibodies useful in the treatment of cancer include bevacizumab (AVASTIN®, Genentech), an antibody to VEGF-A; erlotinib (TARCEVA®, Genentech and OSI Pharmaceuticals), a tyrosine kinase inhibitor which acts on EGFR, dasatinib (SPRYCEL®, Bristol-Myers Squibb Company), an oral Bcr-Abl tyrosone kinase inhibitor; IL-21; pegylated IFN-α2b; axitinib (INLYTA®, Pfizer, Inc.), a tyrosine kinase inhibitor; and trametinib (MEKINIST®, GlaxoSmithKline), a MEK inhibitor (Philips and Atkins, Int Immunol., 27(1):39-46 (2015) which is incorporated herein by reference). Bispecific antibodies useful to treat cancer are described in Krishnamurthy et al., (Pharmacol Ther. 2018 May; 185:122-134), and Yu et al., (J. Hematol Oncol 2017, 10:155), including Blinatumomab and catumaxomab.

The method also provides that the cancer therapeutic comprises one or more cell-based therapies including adoptive cell transfer, tumor-infiltrating leukocyte therapy, chimeric antigen receptor T-cell (CAR-T) therapy, NK-cell therapy and stem cell therapy.

In various embodiments the cell-based therapy is the adoptive transfer of autologous patient-derived cells. In various embodiments the cell-based therapy is the adoptive transfer of allogenic donor-derived cells.

In various embodiments, the cell-based therapy is the transfer of universal donor-derived or induced pluripotent stem cell-derived cells that are not patient specific and amenable to long-term storage. Such therapies are also referred to as 'off-the-shelf' therapies.

In various embodiments, the cancer therapeutic is a hormone therapy. In various embodiments, the cancer therapeutic comprises one or more antibody-drug conjugates. In various embodiments, the cancer therapeutic comprises one or more cancer vaccines. In various embodiments, the cancer vaccine is a protein, polypeptide, and/or nucleic acid vaccine.

In various embodiments, the cancer therapeutic is an immunotherapy selected from the group comprising oncolytic virus, bacteria, oncolytic bacteria or other bacterial consortia, *Bacillus* Calmette-Guerin (BCG), a microbiome modulator, and/or a toll-like receptor (TLR) agonist. In various embodiments, the TLR agonist is a TLR3, TLR4, TLR5, TLR7, TLR8, TLR9, TLR10, TLR11, TLR12, and/or TLR13 agonist. In various embodiments, the TLR agonist is derived from virus, bacteria and/or made synthetically. In various embodiments, the immunotherapy is a STING pathway modulator.

In various embodiments, the cancer therapeutic comprises a viral or a bacterial vector. In various embodiments, the viral vector is selected from the group comprising adenovirus, adeno-associated virus (AAV), herpes simplex virus, lentivirus, retrovirus, alphavirus, flavivirus, rhabdovirus, measles virus, Newcastle disease virus, poxvirus, vaccinia virus, modified Ankara virus, vesicular stomatitis virus, picornavirus, tobacco mosaic virus, potato virus x, comovirus or cucumber mosaic virus. In various embodiments, the virus is an oncolytic virus. In various embodiments the virus is a chimeric virus, a synthetic virus, a mosaic virus or a pseudotyped virus.

It is contemplated that the particle and the cancer therapeutic can be given concurrently, simultaneously, or sequentially. Concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

It is contemplated that the particle and the cancer therapeutic may be given simultaneously, in the same formulation. It is further contemplated that the agents are administered in a separate formulation and administered concurrently, with concurrently referring to agents given within 30 minutes of each other.

In another aspect, the cancer therapeutic is administered prior to administration of the particle composition. Prior administration refers to administration of the cancer therapeutic within the range of one week prior to treatment with the particle, up to 30 minutes before administration of the particle. It is further contemplated that the cancer therapeutic is administered subsequent to administration of the particle composition. Subsequent administration is meant to describe administration from 30 minutes after particle treatment up to one week after administration.

In various embodiments, the particle and/or the cancer therapeutic is administered once daily, twice daily, three times per day, seven times per week, six times per week, five times per week, four times per week, three times per week, twice weekly, once weekly, once every two weeks, once every three weeks, once every 4 weeks, once every two months, once every three months, once every 6 months or once per year.

In various embodiments, the particle and/or the cancer therapeutic is administered intravenously, orally, nasally, intramuscularly, ocularly, transdermally, or subcutaneously.

In various embodiments, the subject is a mammal. In various embodiments, the subject is human.

Kits

As an additional aspect, the disclosure includes kits which comprise one or more compounds or compositions packaged in a manner which facilitates their use to practice methods of the disclosure. In one embodiment, such a kit includes a compound or composition described herein (e.g., a particle alone or in combination with a cancer therapeutic, or compositions thereof), packaged in a container such as a sealed bottle or vessel, with a label affixed to the container or included in the package that describes use of the compound or composition in practicing the method. Preferably, the compound or composition is packaged in a unit dosage form. The kit may further include a device suitable for administering the composition according to a specific route of administration or for practicing a screening assay. Preferably, the kit contains a label that describes use of the inhibitor compositions.

Embodiments

Embodiment 1. A method of treating cancer in a subject, comprising administering a surface functionalized particle alone or in combination with a cancer therapeutic, wherein the subject has one or more immune evasive tumors, immunologically protected tumors, immunologically 'cold' tumors, microsatellite stable tumors, microsatellite instability low tumors, tumors comprising a low immune infiltrate, tumors comprising a low tumor mutational burden, tumors exhibiting heterogeneity, or combinations thereof.

Embodiment 2. A method for treating an immune-evasive tumor in a subject, comprising (i) diagnosing the subject as having an immune-evasive tumor, and (ii) administering a surface functionalized particle to the subject alone or in combination with a cancer therapeutic.

Embodiment 3. The method of embodiment 2, wherein the diagnosing comprises assaying biomarkers/characteristics associated with an immune-evasive tumor, microsatellite stability/instability, tumor mutational burden, resistance to therapy, tumor heterogeneity, or combinations thereof.

Embodiment 4. The method of embodiment 2 or 3, further comprising (iii) determining if the subject's tumor becomes immune responsive, and then (iv) administering surface functionalized particles in combination with an immunotherapy.

Embodiment 5. A method for treating a subject having cancer and who had previously received immunotherapy or in which the cancer is refractory to immunotherapy, comprising administering to the subject a surface functionalized particle alone or in combination with a cancer therapeutic.

Embodiment 6. The method of any one of the preceding embodiments, wherein the particle comprises are polyglycolic acid (PGA) polymers, polylactic acid (PLA), poly (lactic-co-glycolic acid) (PLGA), polystyrene, chitosan, polysaccharide, one or more lipids, diamond, or iron, zinc, cadmium, gold, or silver.

Embodiment 7. The method of any one of the preceding embodiments, wherein the surface functionalized particles are poly (lactic-co-glycolic acid) (PLGA) particles.

Embodiment 8. The method of embodiment 7, wherein the particle comprises polylactic acid:poly glycolic acid ratio from about 1:99 to about 99:1.

Embodiment 9. The method of embodiment 8, wherein the particle comprises about 50:50, about 80:20 to about 100:0 poly lactic acid:poly glycolic acid or from about 50:50, about 80:20 to about 100:0 poly glycolic acid:poly lactic acid.

Embodiment 10. The method of any one of the preceding embodiments, wherein the particle comprises 50:50 poly lactic acid:poly glycolic acid.

Embodiment 11. The method of any one of the preceding embodiments, wherein the particle is surface functionalized by the addition of one or more carboxyl groups.

Embodiment 12. The method of any one of the preceding embodiments, wherein the particle is a negatively charged particle.

Embodiment 13. The method of embodiment 12, wherein the particle is free from therapeutic agents.

Embodiment 14. The method of embodiment 12 or 13, wherein the particle is free from attached peptide or antigenic moieties or other bioactive agents.

Embodiment 15. The method of any one of the preceding embodiments, wherein the particle has a zeta potential between −100 mV and −1 mV.

Embodiment 16. The method of any one of the preceding embodiments, wherein the particle has a zeta potential between −80 mV and −30 mV, or between −50 my and −40 mV.

Embodiment 17. The method of any one of the preceding embodiments, wherein the diameter of the surface functionalized surface is between 0.1 μm to 10 μm.

Embodiment 18. The method of any one of the preceding embodiments, wherein the diameter of the surface functionalized particle is between 400 nm to 800 nm.

Embodiment 19. The method of any one of embodiment 1-18 wherein the surface functionalized particle and/or cancer therapeutic are administered in a composition.

Embodiment 20. The method of embodiment 19 wherein the composition comprises a pharmaceutically acceptable excipient, diluent or carrier.

Embodiment 21. The method of any one of the preceding embodiments, wherein the subject has one or more immunologically cold tumors.

Embodiment 22. The method of any one of the preceding embodiments, wherein the subject has one or more tumors with a low tumor mutational burden.

Embodiment 23. The method of any one of the preceding embodiments, wherein the subject has one or more microsatellite stable tumors.

Embodiment 24. The method of any one of the preceding embodiments, wherein the subject has one or more tumors with low microsatellite instability.

Embodiment 25. The method of any one of the preceding embodiments wherein the subject has one or more tumors with a low tumor immune infiltrate.

Embodiment 26. The method of any one of the preceding embodiments, wherein the administering alters the tumor immune infiltrate.

Embodiment 27. The method of embodiment 25 or 26, wherein the tumor immune infiltrate comprises antigen-presenting cells, myeloid cells, and lymphoid cells.

Embodiment 28. The method of embodiment 27, wherein the antigen presenting cells comprise macrophages and/or dendritic cells.

Embodiment 29. The method of embodiment 27, wherein myeloid cells comprise monocytes, neutrophils, myeloid-derived suppressor cells (MDSCs), and tumor-associated macrophages (TAMs).

Embodiment 30. The method of embodiment 29, wherein the tumor-associated macrophages comprise M1 macrophages, M2 macrophages, and/or MARCO+ macrophages.

Embodiment 31. The method of embodiment 27, wherein lymphoid cells comprise T-cells, B-cells, NK T-cells, and NK cells.

Embodiment 32. The method of any one of the preceding embodiments, wherein the administering alters the anti-tumor immune response.

Embodiment 33. The method of any one of the preceding embodiments, wherein the administering alters the tumor microenvironment.

Embodiment 34. The method of embodiment 33, wherein the tumor microenvironment comprises tumor cells, cancer stem cells, immune cells, and stroma.

Embodiment 35. The method of embodiment 34, wherein the stroma comprises fibroblasts, adipocytes, endothelium, vasculature, mesenchymal stromal cells, and/or extracellular matrix.

Embodiment 36. The method of any one of the preceding embodiments, wherein the administering transforms an immunologically cold tumor into an immunologically hot tumor.

Embodiment 37. The method of any one of the preceding embodiments, wherein the administering reduces tumor size and/or inhibits tumor growth.

Embodiment 38. The method of any one of the preceding embodiments, wherein the subject has a cancer selected from the group consisting of brain cancer, skin cancer, eye cancer, breast cancer, prostate cancer, pancreatic cancer, lung cancer, esophageal cancer, head and neck cancer, cervical cancer, liver cancer, colorectal cancer, bone cancer, uterine cancer, ovarian cancer, bladder cancer, endometrial cancer, stomach cancer, gastric cancer, oral cancer, thyroid cancer, kidney cancer, testicular cancer, leukemia, lymphoma, and mesothelioma.

Embodiment 39. The method of any one of the preceding embodiments, wherein the cancer therapeutic administered in combination with the particle is a chemotherapeutic selected from the group consisting of growth inhibitors, DNA-replication inhibitors, kinase inhibitors, receptor tyrosine kinase inhibitors, signaling cascade inhibitors, angiogenesis inhibitors, metabolic inhibitors, amino acid synthesis inhibitors, selective inhibitors of oncogenic proteins, inhibitors of metastasis, inhibitors of anti-apoptosis factors, apoptosis inducers, enzyme inhibitors, nucleoside signaling inhibitors, antibody-drug conjugates, and DNA-damaging agents.

Embodiment 40. The method of any one of embodiments 1-38, wherein the cancer therapeutic administered in combination with the particle comprises one or more biologic agents selected from the group consisting of cytokines, angiogenesis inhibitors, receptor tyrosine kinase inhibitors, immune checkpoint modulators enzymes, and, monoclonal antibodies.

Embodiment 41. The method of embodiment 40, wherein the cytokines are selected form the group consisting of transforming growth factors, tumor necrosis factor, interferons and interleukins.

Embodiment 42. The method of embodiment 40, wherein the immune checkpoint modulators target Programmed cell death protein 1 (PD1), Programmed cell death protein ligand-1 (PD-L1), cytotoxic T-lymphocyte-associated protein 4 (CTLA-4), T cell Immunoglobulin and Mucin-domain containing-3 (TIM-3), Lymphocyte-activation Gene-3 (LAG-3) and/or TIGIT (T cell immunoreceptor with Ig and ITIM domains).

Embodiment 43. The method of embodiment 42, wherein the immune checkpoint modulator is an antibody selected from the group consisting of ipilimumab, Tremelimumab, Pembrolizumab, Nivolumab, Atezolizumab, Avelumab, Cemiplimab and Durvalumab.

Embodiment 44. The method of embodiment 40, wherein the monoclonal antibody comprises a mono-specific, bi-specific, or tri-specific antibody.

Embodiment 45. The method of embodiment 40, wherein the monoclonal antibody comprises a bi-specific T-cell engager (BiTE).

Embodiment 46. The method of embodiment 40, wherein the monoclonal antibody is selected from the group comprising Alemtuzumab, Bevacizumab, Brentuximab, Cetuximab, Denosumab, Ibritumomab, Trastuzumab, Panitumumab, Pertuzumab, and Rituximab.

Embodiment 47. The method of embodiments 1-38, wherein the cancer therapeutic administered in combination with the particle comprises one or more cell-based therapies selected from the group consisting of adoptive cell transfer, tumor-infiltrating leukocyte therapy, chimeric antigen receptor T-cell therapy (CAR-T), NK-cell therapy and stem cell therapy.

Embodiment 48. The method of any one of embodiments 1-38, wherein the cancer therapeutic administered in combination with the particle is a hormone therapy.

Embodiment 49. The method of any one of embodiments 1-38, wherein the cancer therapeutic administered in combination with the particle comprises one or more cancer vaccines.

Embodiment 50. The method of any one of embodiments 1-38, wherein the cancer therapeutic administered in combination with the particle is one or more immunotherapies comprising oncolytic virus, oncolytic bacteria or other bacterial compositions, *Bacillus* Calmette-Guerin (BCG), microbiome modulator, STING pathway modulator, and/or toll-like receptor (TLR) modulator.

Embodiment 51. A method of treating cancer in a subject comprising the steps of:

a. determining the immunologic status of the tumor and/or the tumor mutational burden and/or microsatellite instability status of the tumor;

b. diagnosing the tumor to be immune evasive and/or immunologically protected and/or immunologically cold and/or having a low tumor immune infiltrate and/or having a low tumor mutational burden and/or as microsatellite stable and/or refractory and/or microsatellite instability low and/or exhibiting heterogeneity, or combinations thereof.

c. administering surface functionalized particles alone or in combination with a cancer therapeutic.

Embodiment 52. The method of any one of the preceding embodiments wherein the particle and/or the cancer therapeutic is administered once daily, twice daily, three times per day, seven times per week, six times per week, five times per week, four times per week, three times per week, twice weekly, once weekly, once every two weeks, once every three weeks, once every 4 weeks, once every two months, once every three months, once every 6 months or once per year.

Embodiment 53. The method of any one of the preceding embodiments, wherein the particles are administered intravenously, orally, nasally, intramuscularly, ocularly, transdermally, or subcutaneously.

Embodiment 54. The method of any one of the preceding embodiments, wherein the subject is human.

Embodiment 55. The method of any one of the preceding embodiments, wherein the administration improves one or more symptoms of the cancer.

Embodiment 56. The method of any one of the preceding embodiments, wherein the surface functionalized particle is a negatively charged particle free from attached peptide or antigenic moieties or other bioactive agents.

Embodiment 57. The method of embodiment 56, wherein the particle is a PLGA particle having a zeta potential between −80 to −30 mV and a diameter between 200 and 2000 nm.

Embodiment 58. The method of any one of the preceding claims, wherein the tumor is an immune evasive tumor Embodiment 59. The method of any of embodiments 1-57, wherein the tumor is an immunologically protected tumor.

Embodiment 60. The method of any of embodiments 1-57, wherein the tumor is an immunologically 'cold' tumor.

Embodiment 61. The method of any of embodiments 1-57, wherein the tumor is a microsatellite stable tumor.

Embodiment 62. The method of any of embodiments 1-57, wherein the tumor is a microsatellite instability low tumor.

Embodiment 63. The method of any of embodiments 1-57, wherein the tumor comprises a low immune infiltrate.

Embodiment 64. The method of any of embodiments 1-57, wherein the tumor comprises a low tumor mutational burden.

Embodiment 65. The method of any of embodiments 1-57, wherein the tumor exhibits heterogeneity.

Additional aspects and details of the disclosure will be apparent from the following examples, which are intended to be illustrative rather than limiting.

EXAMPLES

Example 1

In order to determine the efficacy of surface functionalized particles against immunologically "cold", or immune-evasive, tumors with a low tumor mutational burden, a syngeneic tumor model was established using the murine B16F10 melanoma cell line. B16F10 cells have previously been shown to be immunologically "cold", carry a low TMB, and exhibit resistance to checkpoint inhibitor therapy (Song et al., Nat Commun. 9: 2237, 2018). Briefly, 6-8-week-old C57BL/6 mice were implanted with B16F10 cells via subcutaneous injection into the flanks. After palpable tumor formation (~100 $mm^3$ in size), animals were randomized into one of four treatment groups as follows: Group 1: Control treatment (n=15); Group 2: SFP (n=15); Group 3: anti-PD1 (n=15); Group 4: Combo (SFP+anti-PD1) (n=15).

| Group | Treatment | SFP Treatment Days (After palpable tumor formation) | Anti-PD1 mAb Treatment Days (After palpable tumor formation) |
|---|---|---|---|
| 1 | Control (Saline) | — | — |
| 2 | SFP | 1, 4, 7, 10, 13, 16, 19, 22, 25 | — |
| 3 | Anti-PD1 mAb | — | 1, 5, 8, 12, 15, 19, 22, 25 |
| 4 | Combo (SFP + anti-PD1 mAb) | 1, 4, 7, 10, 13, 16, 19, 22, 25 | 1, 5, 8, 12, 15, 19, 22, 25 |

SFP, composed of PLGA and having a negative zeta potential (e.g., ranging between −100 mV and −1 mV, such as between −80 mV and −30 mV), (1 mg) were administered via intravenous (i.v) injection and anti-PD1 (100 μg) was administered via intraperitoneal (i.p) injection according to the following treatment schedule:

Tumor growth was evaluated by measuring tumor size in two dimensions using a caliper. Tumor volumes were calculated using the formula $V=0.5\times a\times b^2$, where a and b are the long and short diameters of the tumor, respectively. Tumor sizes were expressed in $mm^3$.

Figure 12:
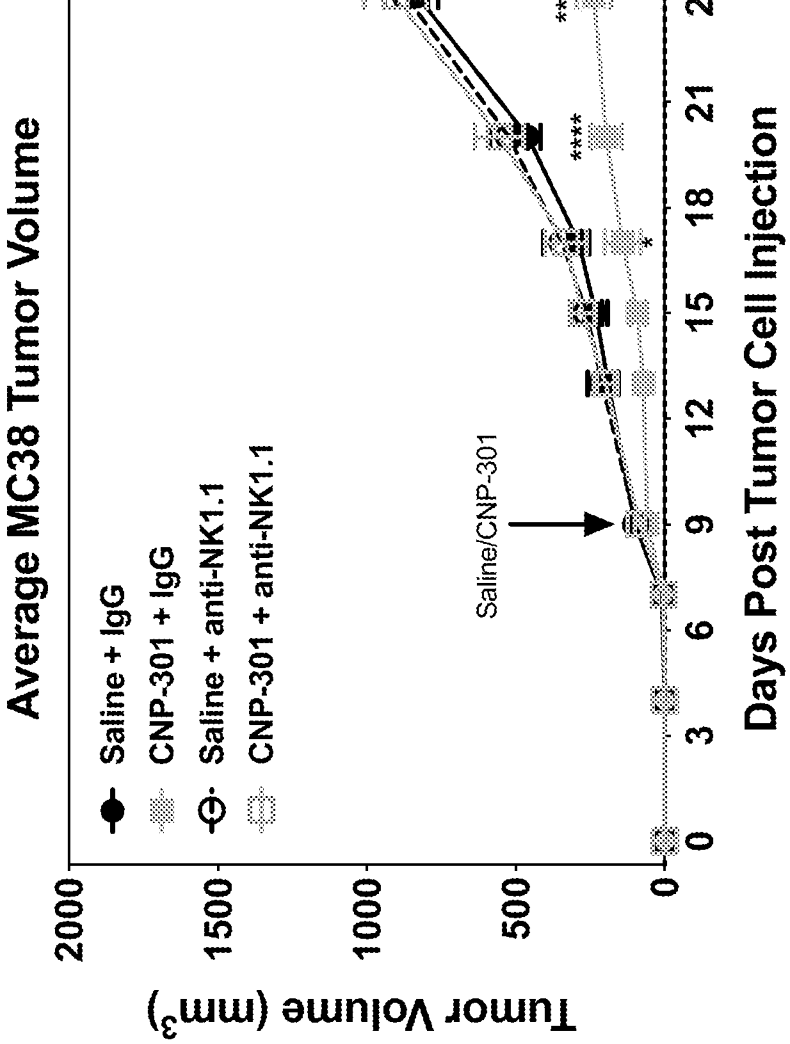
FIG. 12 shows the effect of NK cell depletion on efficacy of surface functionalized particle, CNP-301, in MC38 tumor model. C57BL/6 mice were injected subcutaneously with MC38 tumor cells. Animals were treated with Saline or CNP-301 with or without anti-NK1.1 antibody after palpable tumor formation (50 mm$^3$). Isotype antibody was used as control. Saline/CNP-301 was administered via intravenous injection. Isotype/anti-NK1.1 antibody was administered via intraperitoneal injection. All treatments were administered once every three days. Shown are tumor volumes of mice treated with saline or CNP-301 in the presence (IgG) or absence of (anti-NK1.1) NK cells. Statistical significance was determined by 2-way ANOVA with Bonferroni's multiple comparison test. N=5 per group.

Five animals from each group were sacrificed on day 12 after initiation of treatment and the frequencies of MDSCs and TAMs were evaluated in the tumor by flow cytometry. Cell viability was also evaluated using a live/dead stain. As shown in FIG. 1A, 12 days of treatment with SFP, alone or in combination with anti-PD1, led to a complete abrogation of cell viability in the tumors. Treatment with anti-PD1 alone also resulted in a modest, but significant, decrease in cell viability.

In agreement with its effect on cell viability, treatment with SFP, but not anti-PD1, strongly inhibited tumor growth. Inhibition of tumor growth with SFP and anti-PD1 in combination therapy was comparable to that of SFP monotherapy suggesting that tumor inhibition in the combination group was driven primarily by SFP and consistent with the fact that B16F10 melanoma tumors are resistant to checkpoint blockade (FIG. 1B). Consistent with its effect on tumor growth, SFP treatment led to prolonged survival (~10 days) compared to control and anti-PD1 treatment. Mice in the SFP monotherapy eventually succumbed to disease, indicative of the extremely aggressive disease course of B16F10 melanoma tumors. As expected, due to B16F10 tumor resistance to anti-PD1, combination therapy did not demonstrate a synergistic effect and survival in this group was comparable to that in the SFP monotherapy group (FIG. 1C).

As shown in FIGS. 1D-1F, treatment with SFP alone resulted in a significant decrease in the frequency of MDSCs (CD11b+Ly6G+) and TAMs (CD11b+F4/80+) in the tumor. While MDSC frequency trended towards a decrease after SFP and anti-PD1 combination therapy (p=0.055), frequency of TAMs was significantly reduced in this treatment group. Treatment with SFP alone resulted in a trend towards increased frequencies of NK cells in the tumor, and combination therapy resulted in a statistically significant increase in NK cell frequencies (FIG. 1F). The effect of combination therapy on MDSCs, TAMs, and NK cells appeared to be driven by SFP as the frequencies of these cells in the tumor was unaffected by treatment with anti-PD1 alone.

Example 2

Treatment with Surface Functionalized Particles Leads to Reduced Primary Orthotopic 4T1 Mammary Tumors and Inhibits their Metastasis to the Lungs In order to determine the efficacy of surface-functionalized particles described in Example 1, e.g., CNP-301, at inhibiting the growth and metastasis of immunologically 'cold' mammary gland tumors having a low tumor mutational burden, a syngeneic orthotopic tumor model was established using the murine 4T1 mammary tumor cell line. The 4T1 tumor cell line is derived from the mammary gland tissue of a BALB/c mouse. 4T1 cells are triple-negative for estrogen, progesterone, and HER2 receptors and have been used extensively as a model of stage IV human breast cancer. 4T1 tumors are highly immunogenic and invasive, and mimic human disease by metastasizing spontaneously to distant organs such as lungs. Importantly, 4T1 tumors are resistant to anti-PD1 checkpoint inhibitor therapy, similar to human triple-negative breast cancers. In the present study, CNP-301 efficacy against orthotopic 4T1 breast tumors was compared with Control (Saline) and an anti-PD1 monoclonal antibody treatment.

6-8-week-old BALB/c mice were injected with $1\times10^5$ 4T1 tumor cells in the fourth mammary fat pad. 4T1 tumor cells used in these experiments were engineered to express luciferase enabling their detection by IVIS® bioluminescence imaging.

Treatments were initiated at different timepoints after tumor injection as follows:

| GROUP | DAY OF TREATMENT INITIATION AFTER TUMOR INJECTION |
|---|---|
| Saline | 5 (after palpable tumor of 50 $mm^3$) |
| CNP-301 | 1 |
| CNP-301 | 2 |
| CNP-301 | 4 |
| CNP-301 | 5 (after palpable tumor of 50 $mm^3$) |
| Anti-PD1 | 5 (after palpable tumor of 50 $mm^3$) |

Each group consisted of 7-8 animals. Treatments were administered once every 3 days. CNP-301 was administered via tail vein injection at a dose of 1 mg/mouse. Anti-PD1 was administered via i.p injection at a dose of 200 μg/mouse once every 3 days. Tumor growth was monitored routinely by measuring tumors using standard calipers. Tumor volumes were calculated using the following formula:

$$\text{Tumor Volume}=0.5(\text{length})\times(\text{width})^2$$

On Day 20 after tumor inoculation, animals were euthanized, and lung metastases were detected by IVIS® bioluminescence imaging.

Figure 2A:
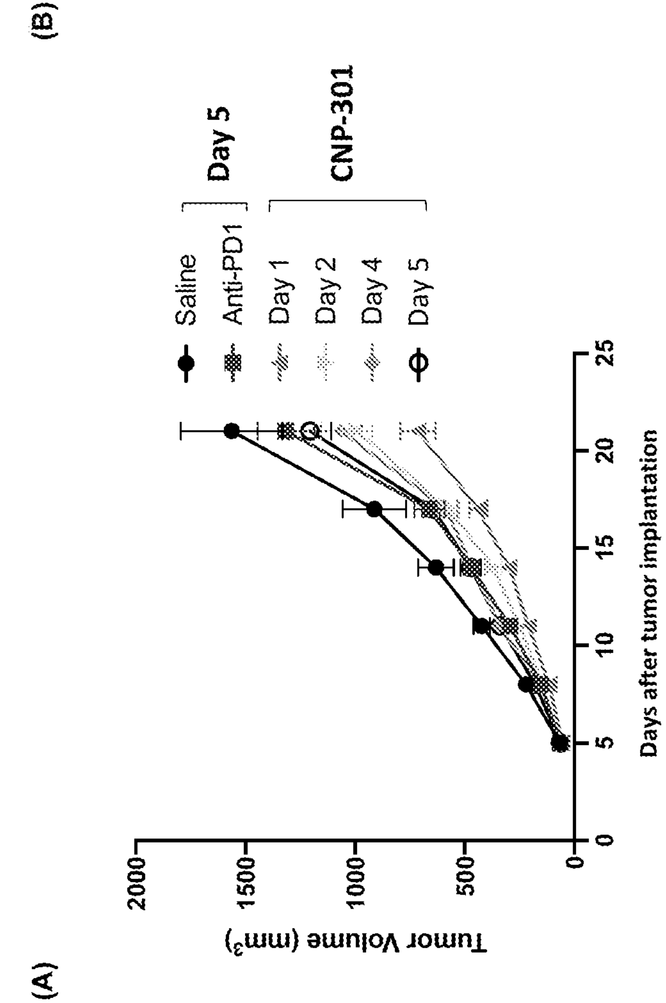
FIG. 2A-2B shows efficacy of treatment with surface functionalized particles after orthotopic 4T1 tumor inoculation inhibits primary growth.
Figure 2B:
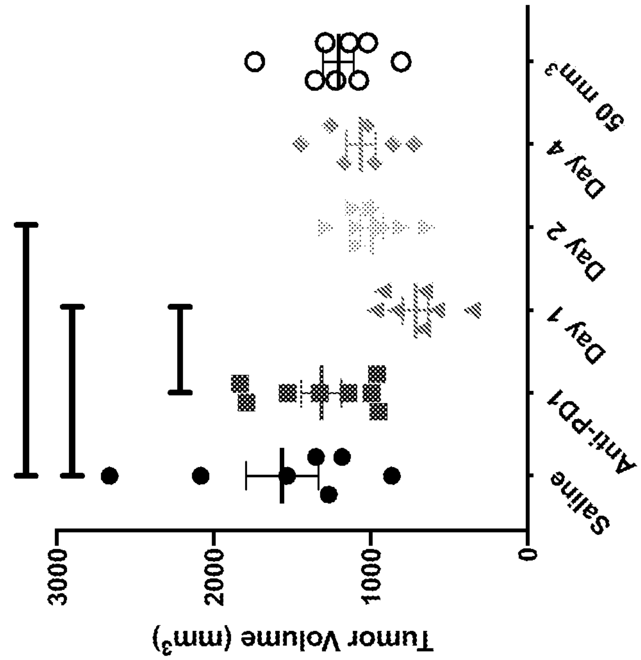
Figure 3A:
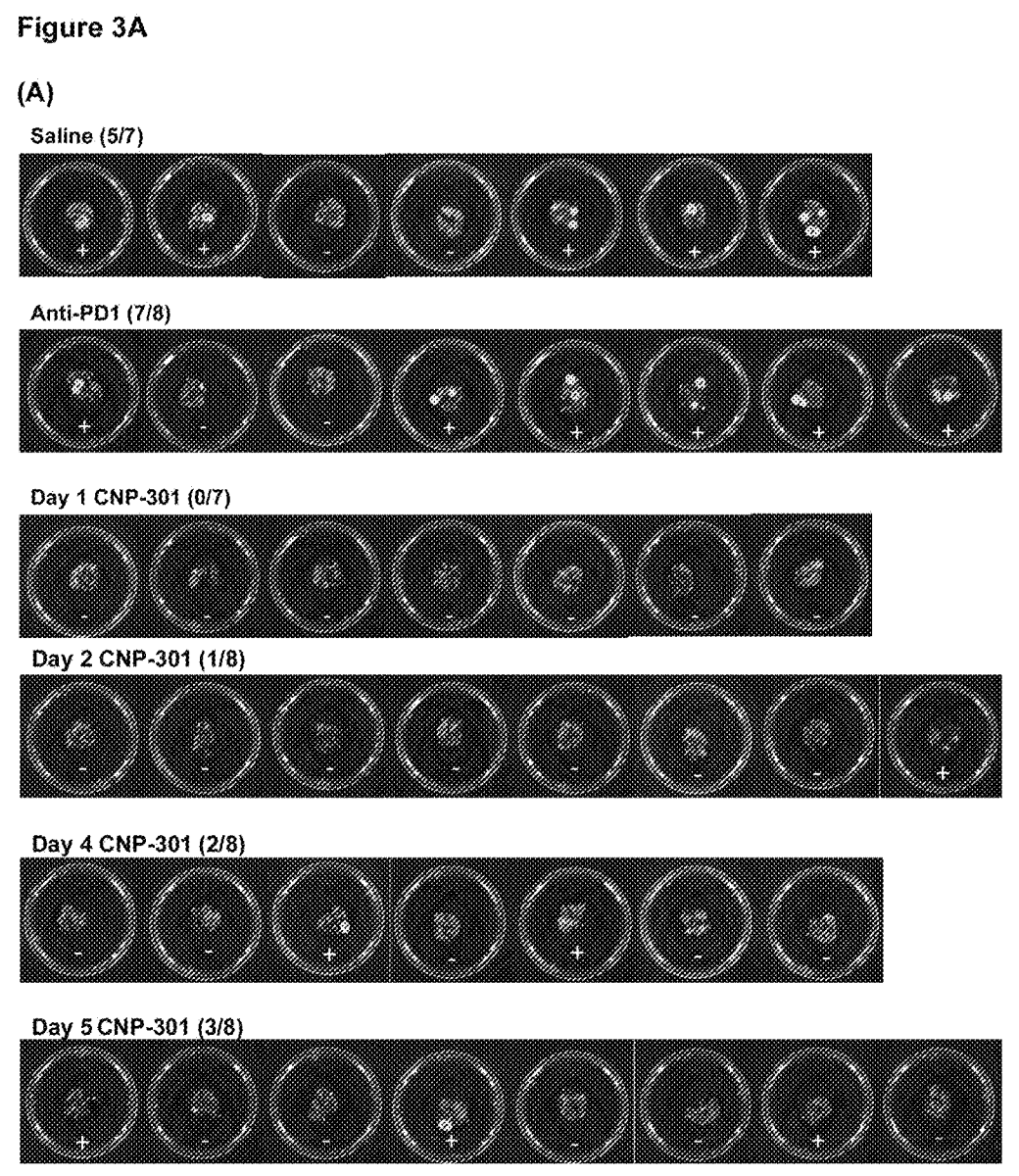
Figure 3B:
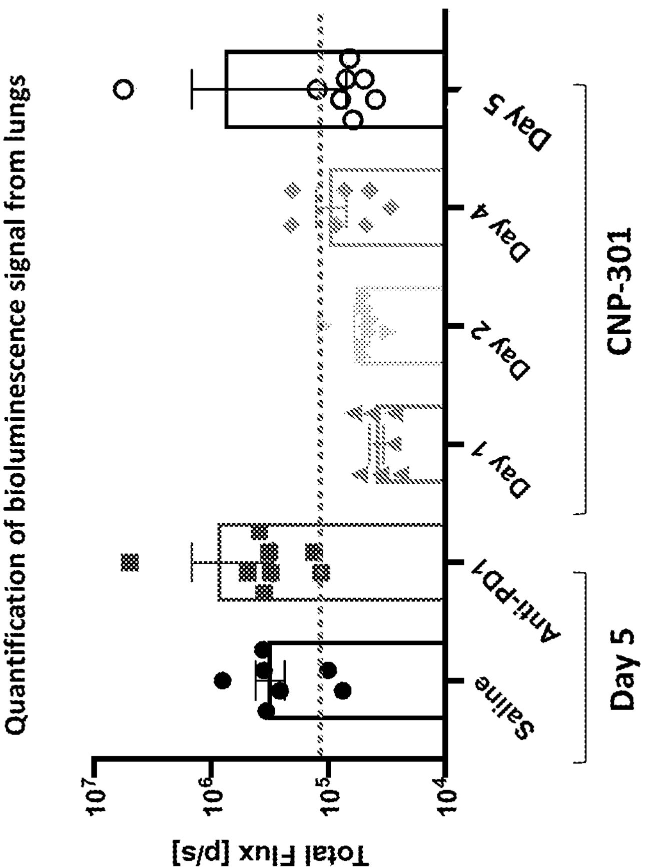
Figures 5A, 5B, 5C:
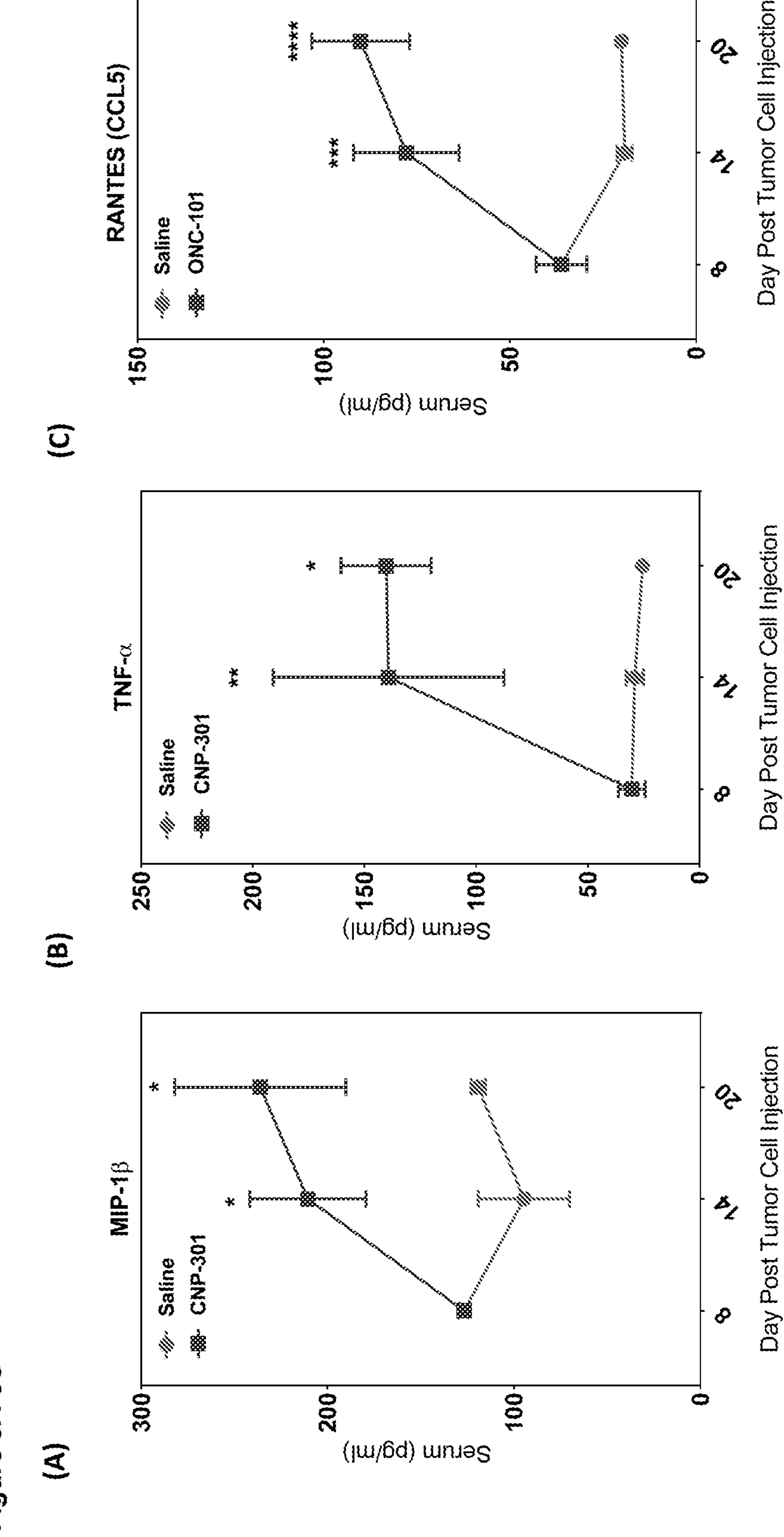
FIGS. 5A-5E shows the effect of treatment with surface functionalized particles, CNP-301, on cytokine/chemokine levels in blood of B16F10 tumor bearing mice. C57BL/6 mice were subcutaneously injected with B16F10 tumor cells. Treatment with Saline or CNP-301 was initiated after palpable tumor formation. Treatment was administered via iv injection once every three days. Levels of indicated cytokines and chemokines were measured in blood on Day 8 (prior to 1$^{st}$ dose), Day 14 (24 hours after 3$^{rd}$ dose), and Day 20 (24 hours after 5th dose).
Figures 5D, 5E:
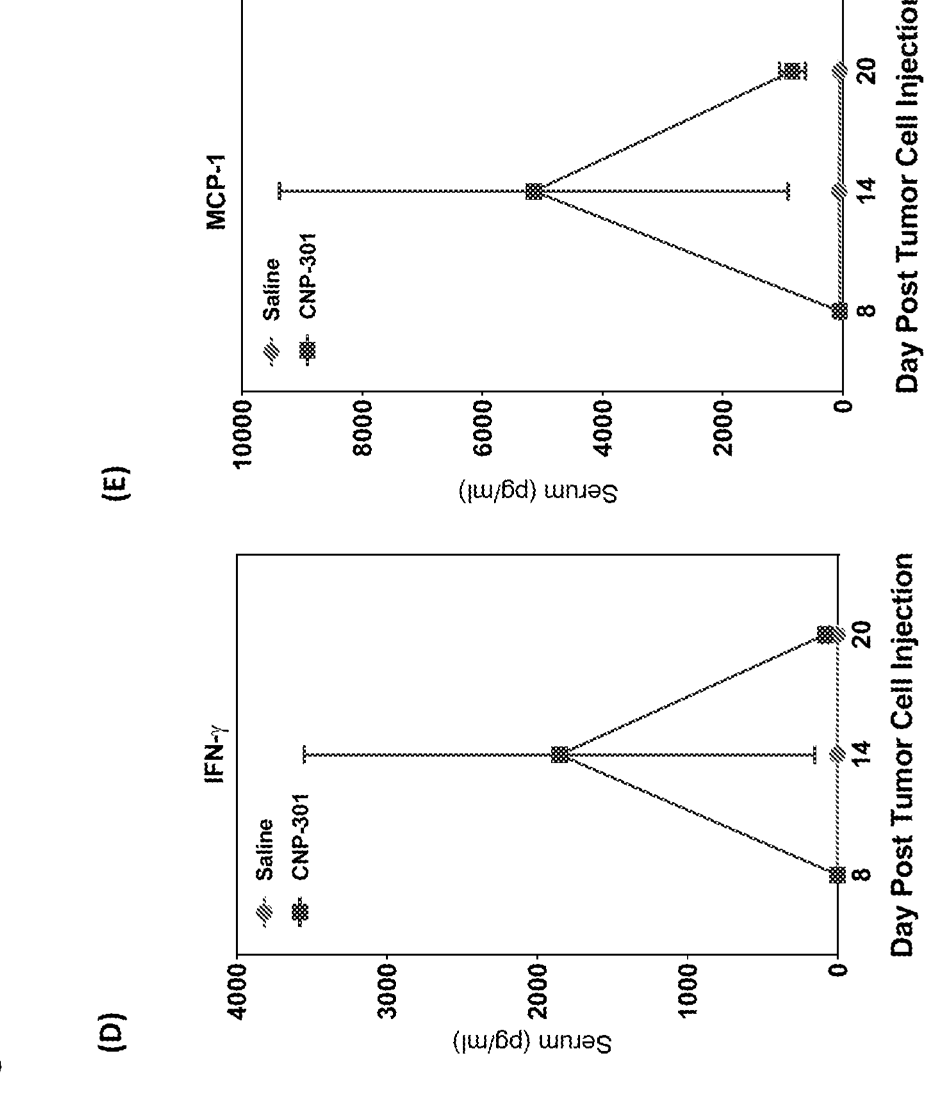
Figures 6A, 6B:
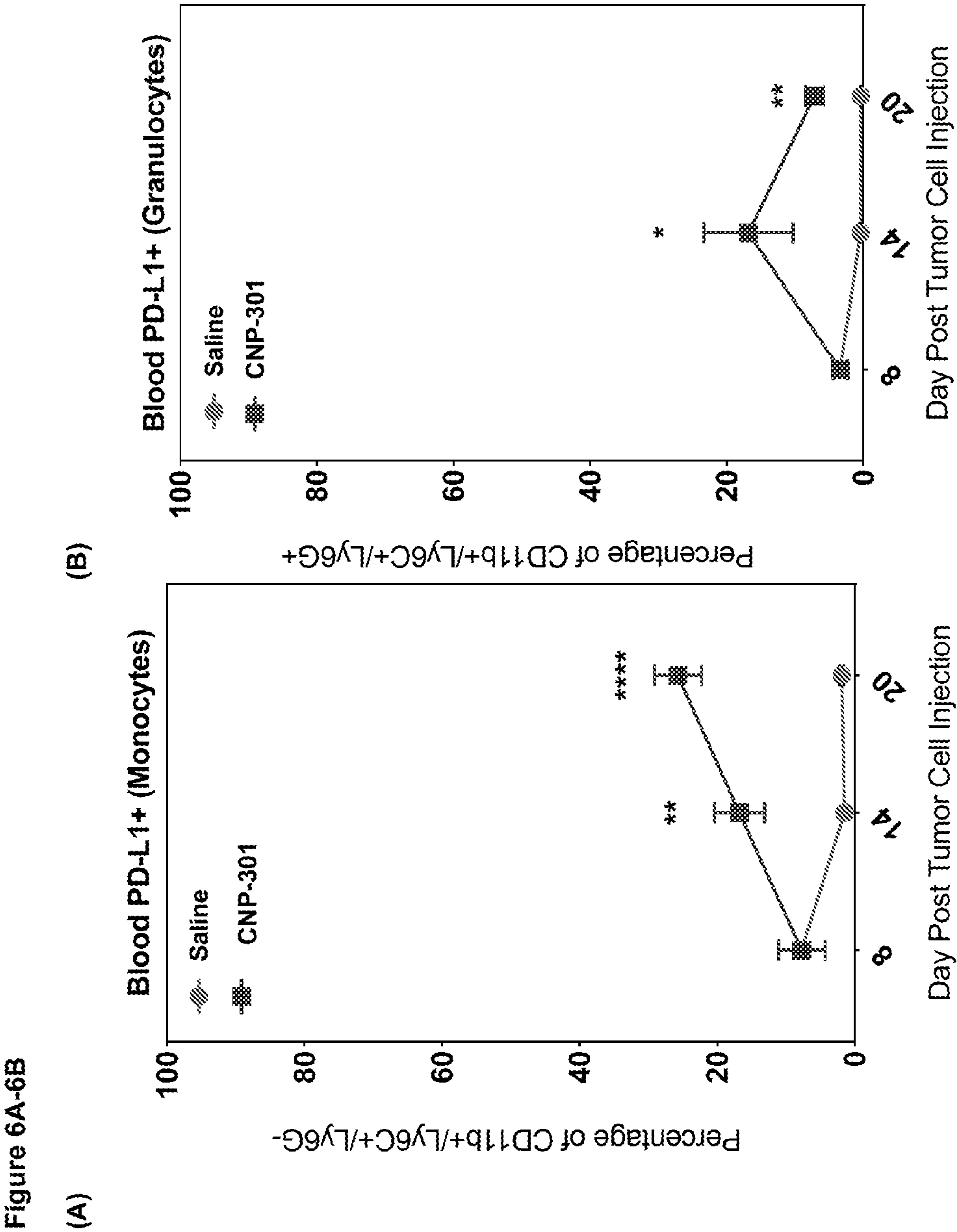
FIGS. 6A-6G shows the effect of treatment with surface functionalized particles, CNP-301, on immune cells in blood. C57BL/6 mice were subcutaneously injected with B16F10 tumor cells. Treatment with Saline or CNP-301 was initiated after palpable tumor formation. Treatment was administered via iv injection once every three days. Frequency of PD-L1+(FIG. 6A) monocytes (CD11b$^+$Ly6C$^+$ Ly6G$^-$) and (FIG. 6B) granulocytes (CD11b$^+$Ly6C$^+$Ly6G$^+$), (FIG. 6C) cell surface IL-15$^+$ cells (CD45$^+$), (FIG. 6D) total NK cells (CD3$^-$NK1.1$^+$), (FIG. 6E) Granzyme$^+$ NK cells (CD3$^-$NK1.1$^+$), (FIG. 6F) Perforin$^+$ NK cells (CD3$^-$ NK1.1$^+$), and (FIG. 6G) CD244$^+$ NK cells (CD3$^-$NK1.1$^+$) in blood was assayed on Day 8 (prior to 1$^{st}$ dose), Day 14 (24 hours after 3$^{rd}$ dose), and Day 20 (24 hours after 5$^{th}$ dose). Immune cells were assayed from blood by flow cytometry. Statistical significance was determined by 2-way ANOVA with Bonferroni's multiple comparison test. N=5 per group.
Figure 6C:
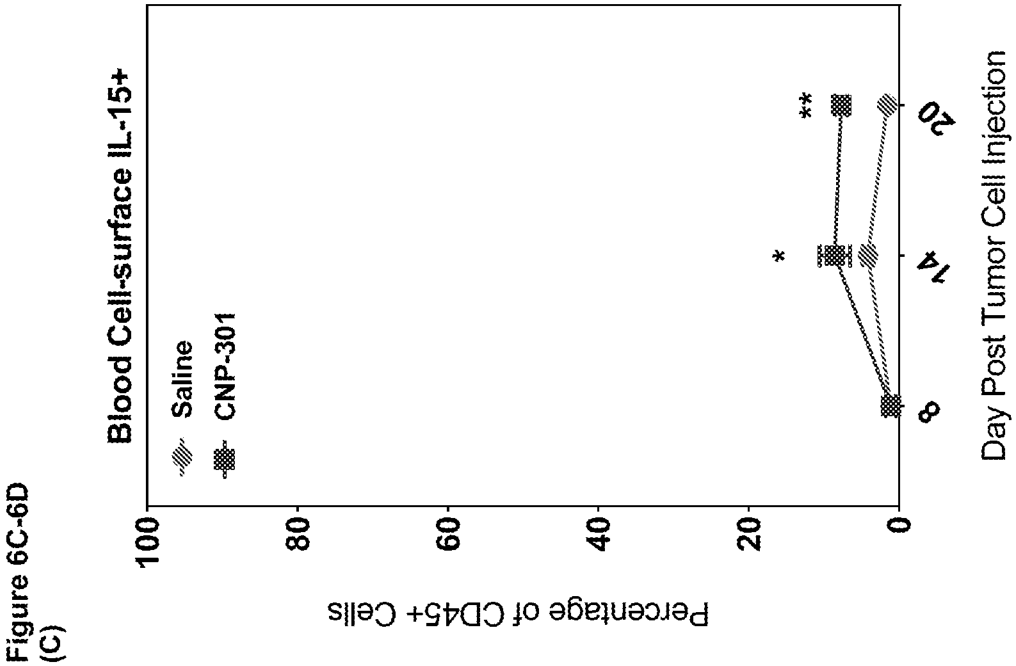
Figure 6D:
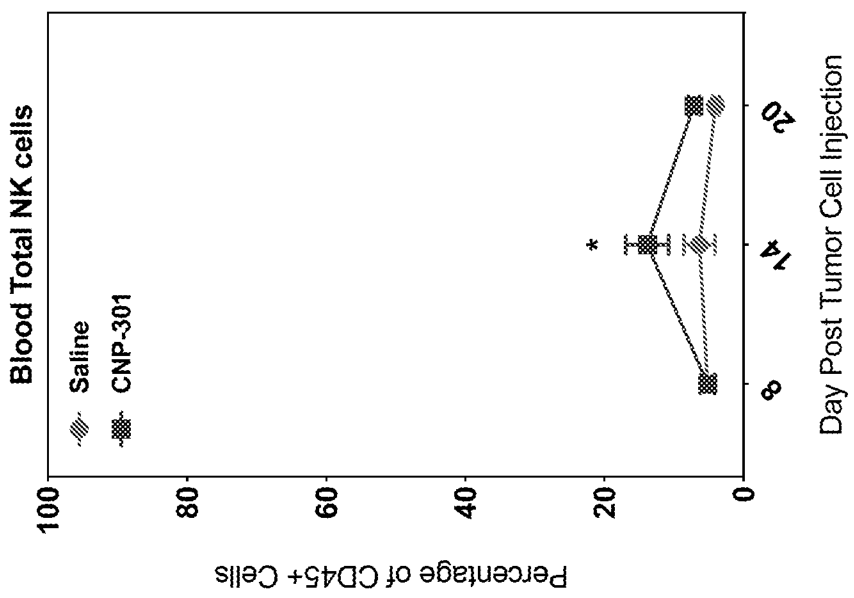
Figure 6E:
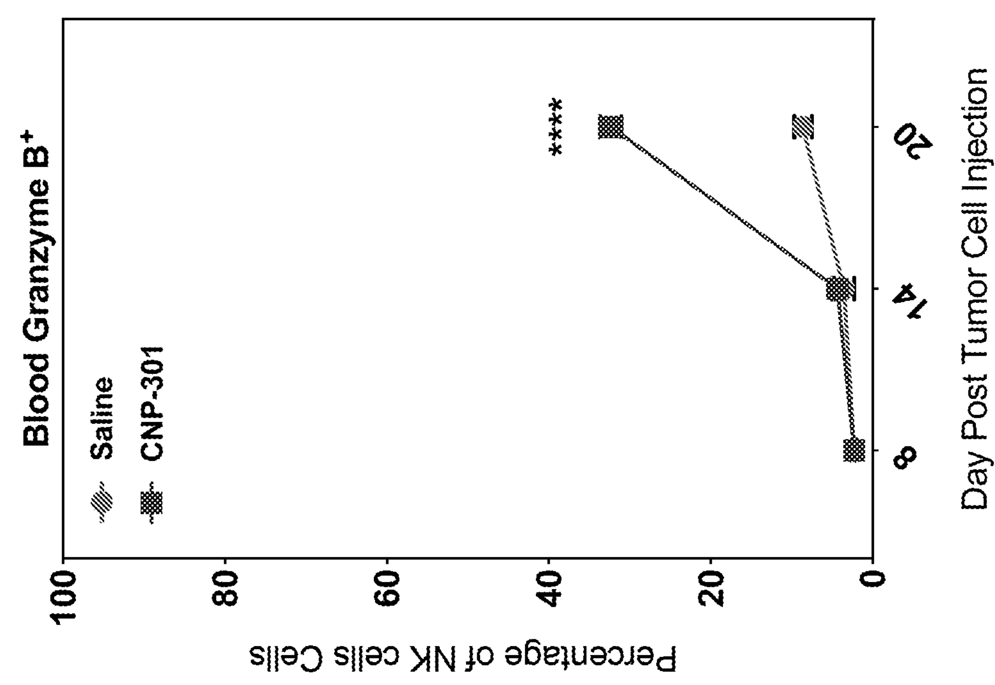
Figure 6F:
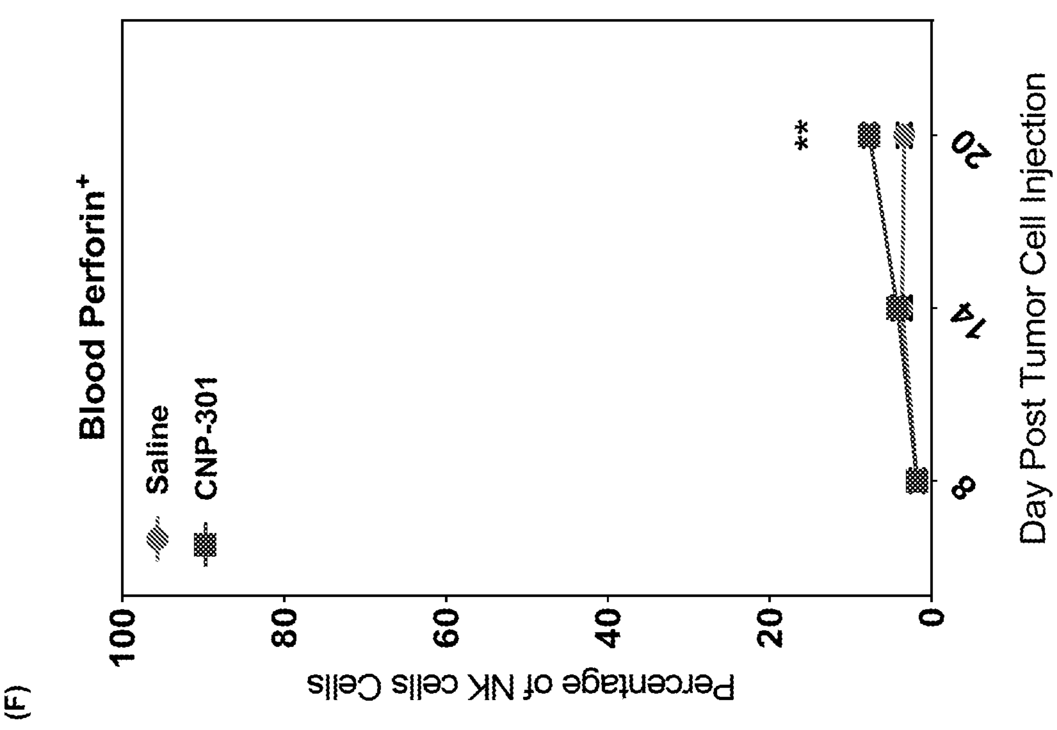
Figure 6G:
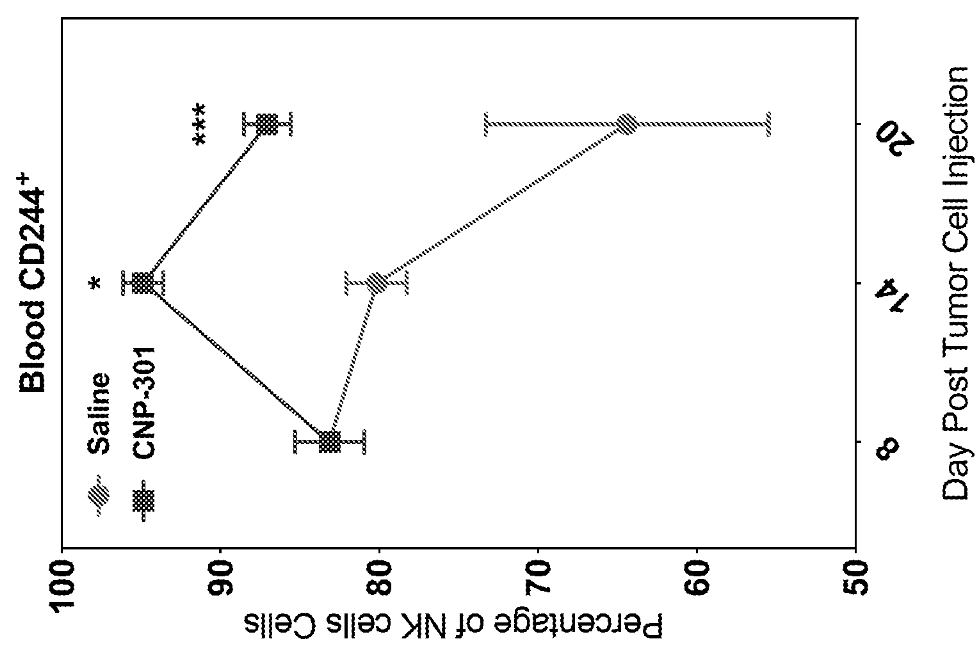

As shown in FIG. 2A-2B, compared to Control and anti-PD-1 treatment, treatment with CNP-301 initiated on Days 1 and 2 resulted in a significant reduction in the growth of primary orthotopic 4T1 tumors. As shown in FIG. 3A-3B, IVIS® bioluminescence imaging of lungs on Day 20 revealed that treatment with CNP-301 significantly reduced the metastasis of primary 4T1 tumors to the lungs. While the majority of animals in the Control and anti-PD1 treatment groups developed metastasis (?), treatment with CNP-301 initiated on Day 1 completely abrogated lung metastases. Mice treated with CNP-301 starting on Days 2, 3, and 5 developed lung metastases in certain animals (1/8, 2/8, and 3/8 mice, respectively); however, these metastatic lesions were significantly smaller in size compared to metastases in the Control and anti-PD1 treatment groups. Together, these data demonstrate that CNP-301 treatment leads to reduced growth of primary orthotopic 4T1 tumors and inhibits their metastasis to the lungs.

Example 3

Treatment with Surface Functionalized Particles Inhibits the Growth of Pre-Existing 4T1 Metastatic Lesions in the Lungs In order to determine the efficacy of surface-functionalized particles, e.g., CNP-301, at inhibiting pre-existing metastatic lesions, a syngeneic orthotopic tumor resection model was established using the murine 4T1 mammary tumor cell line. Briefly, 6-8-week-old BALB/c mice were injected with $1\times10^5$ 4 T1 tumor cells in the fourth mammary fat pad. 4T1 tumor cells used in these experiments were engineered to express luciferase enabling their detection by IVIS® bioluminescence imaging. Primary 4T1 tumors were surgically resected on Day 11 after tumor injection after primary tumors have already begun metastasizing to the lungs. On Day 12 after tumor injection, animals were treated with Saline (Control) or CNP-301. CNP-301 was administered via tail vein injection at a dose of 1 mg/mouse. On Day 42 after tumor injection, animals were euthanized and 4T1 primary tumor metastases to the lungs was evaluated by metastatic lesions in the lungs were evaluated by IVIS® bioluminescence imaging. The study design is depicted in FIG. 4A.

Figures 4A, 4B:
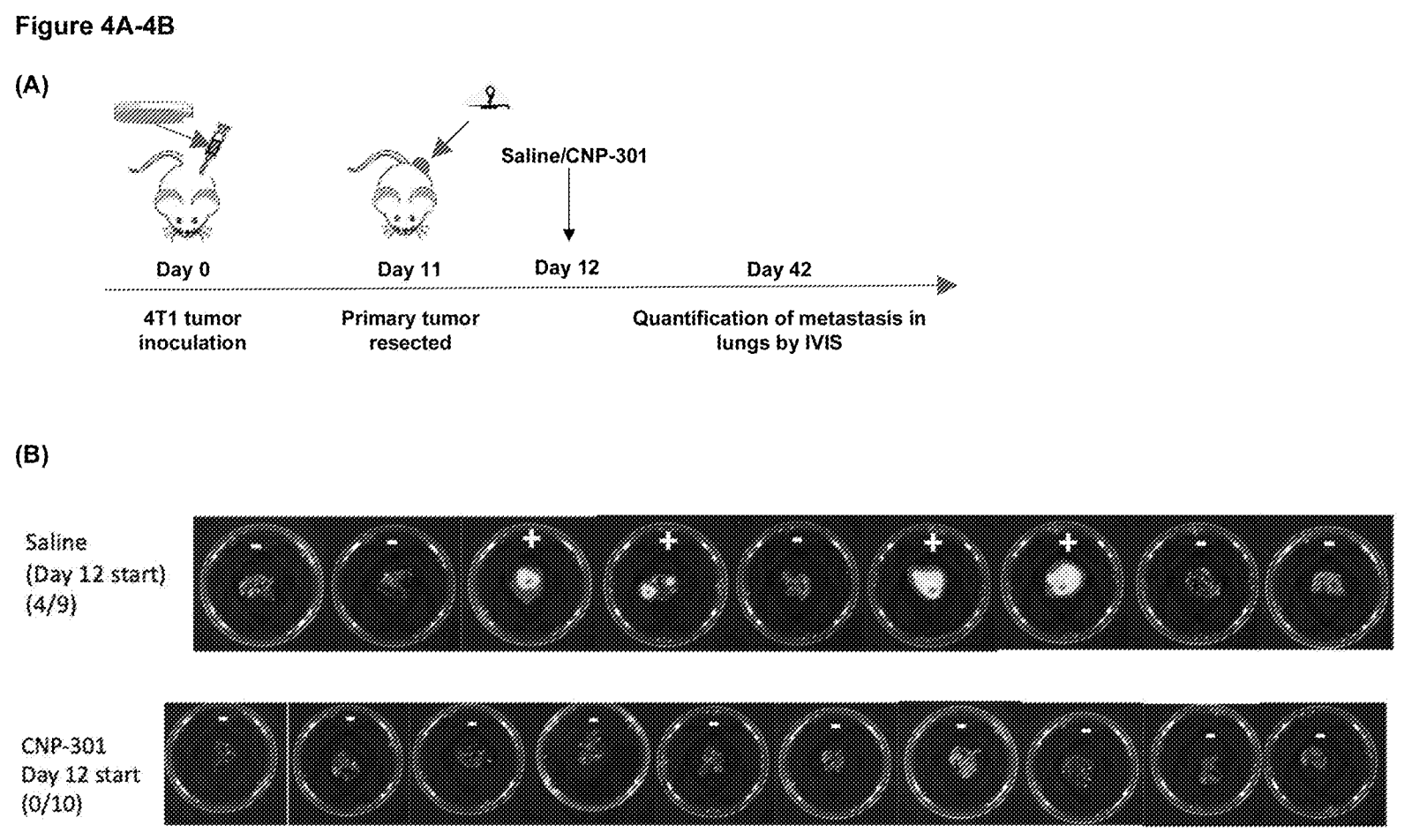

As shown in FIG. 4B, treatment with CNP-301 completely inhibited the growth of 4T1 lung metastases as none of the mice showed evidence of metastatic lesions examined by IVIS® bioluminescence imaging. In contrast, 4/9 (44.44%) mice showed evidence of lung metastases in the Control (Saline) treatment group. These observations are highly significant as the tumor resection model study design is similar to the current treatment paradigm for metastatic triple-negative breast cancer in the clinic where primary tumors are surgically removed followed by neoadjuvant treatment regimen targeted at inhibiting the growth of metastatic lesions. These data show that CNP-301 may be effective for the treatment of human triple-negative breast cancers in the neoadjuvant setting.

Example 4

Treatment with Surface Functionalized Particles Induces Pro-Inflammatory Immunological Changes in the Blood and Tumor of B16F10 Tumor-Bearing Mice B16F10 murine melanoma tumors are considered immunologically 'cold' having a low tumor mutational burden. Additionally, these tumors are resistant to treatment with immunotherapies (e.g anti-PD1 checkpoint inhibitors) partly owing to their immunological status such as low tumor immune infiltrate.

The efficacy of CNP-301 at inducing pro-inflammatory anti-tumor immunological changes in B16F10 tumor-bearing mice was examined. Briefly, 6-8-week-old C57BL/6 mice were subcutaneously injected with B16F10 tumor cells. After palpable tumor formation (~50 $mm^3$), animals were treated with Saline (Control) or CNP-301. Animals were treated once every three days. CNP-301 was administered via tail vein injection at a dose of 1 mg/mouse.

The following parameters were evaluated at different timepoints [Day 8 (prior to 1st dose), Day 14 (24 hours after the 3rd dose), and Day 20 (24 hours after the $5^{th}$ dose) after tumor injection]: pro-inflammatory cytokines/chemokines in blood by ELISA, myeloid-cell phenotypes in blood and tumor by flow cytometry, and lymphoid-cell functional phenotypes in blood and tumor by flow cytometry.

As shown in FIG. 5A-5E, compared to Saline (Control), CNP-301 treatment led to a statistically significant increase from baseline (Day 8) in the levels of pro-inflammatory cytokines/chemokines (A) MIP-1β, (B) TNF-α, and (C) RANTES on Days 14 and 20. CNP-301 treatment also led to an increase from baseline (Day 8) in the levels of (D) IFN-γ and (E) MCP-1 on Day 14; however, this increase was not statistically significant.

As shown in FIG. 6, compared to Saline (Control), CNP-301 treatment led to a statistically significant increase from baseline (Day 8) in the frequency of PD-L1$^+$ monocytes (FIG. 6A) and granulocytes (FIG. 6B) in blood on Days 14 and 20. PD-L1$^+$ expression on myeloid cells is associated with immunoregulatory functions and is induced upon activation of these cells. Consistent with an activation phenotype, CNP-301 treatment lead to a statistically significant increase from baseline (Day 8) in the frequency of myeloid cells expressing IL-15 on their cell surface in blood on Days 14 and 20 (FIG. 6C). Cell-surface IL-15 expression on myeloid cells is known to induce T cell and NK cell activation via interactions between IL-15 on myeloid cells and their cognate receptor on T cells and NK cells in trans. In line with these observations, CNP-301 treatment led to a statistically significant increase from baseline in the frequency of total NK cells (FIG. 6D) and activated (Granzyme$^+$, Perforin$^+$, and CD244$^+$) NK cells (FIG. 6E-6G) in blood on Days 14 and 20.

Figures 7A, 7B:
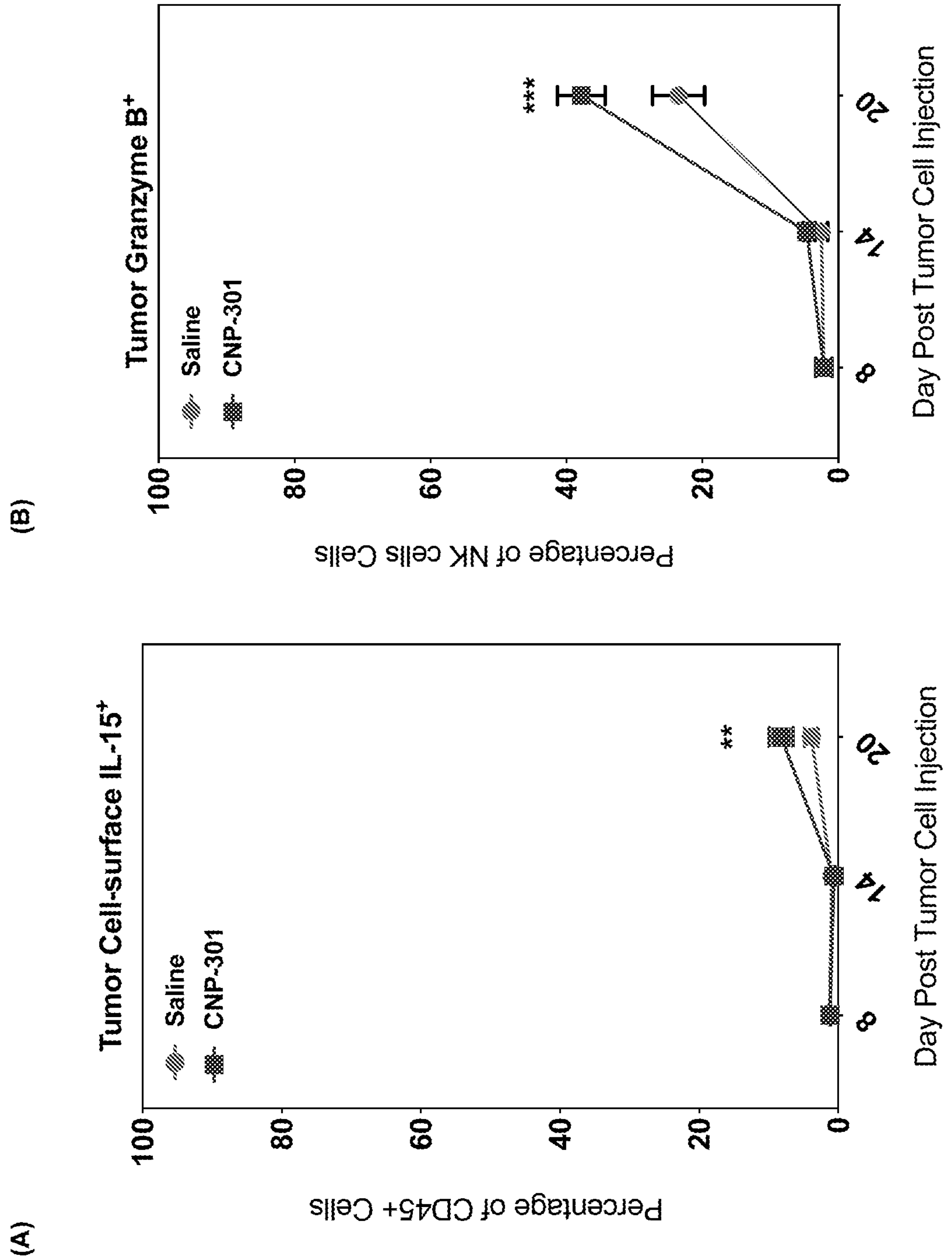
FIGS. 7A-7D shows the effect of treatment with surface functionalized particles, CNP-301, on immune cells in tumor. C57BL/6 mice were subcutaneously injected with B16F10 tumor cells. Treatment with Saline or CNP-301 was initiated after palpable tumor formation. Treatment was administered via iv injection once every three days. Frequency of (FIG. 7A) cell surface IL-15+ cells (CD45+), (FIG. 7B) Granzyme$^+$ NK cells (CD3$^-$NK1.1$^+$), (FIG. 7C) Perforin$^+$ NK cells (CD3$^-$NK1.1$^+$), and (FIG. 7D) CD244$^+$ NK cells (CD3$^-$NK1.1$^+$) in blood was assayed on Day 8 (prior to 1$^{st}$ dose), Day 14 (24 hours after 3$^{rd}$ dose), and Day 20 (24 hours after 5th dose). Immune cells were assayed from blood by flow cytometry. Statistical significance was determined by 2-way ANOVA with Bonferroni's multiple comparison test. N=5 per group.
Figures 7C, 7D:
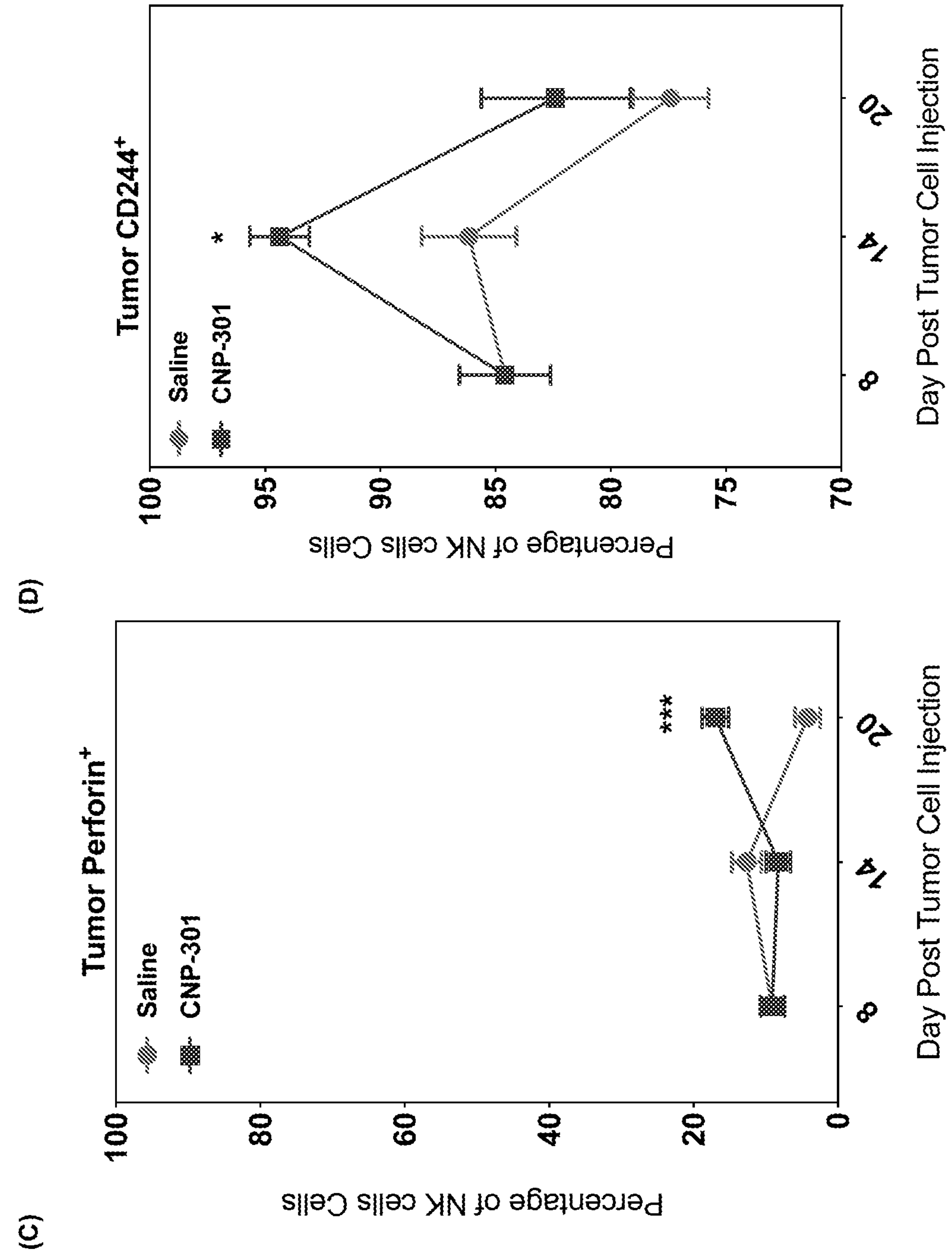

Similar to observations in blood, examination of B16F10 tumors at different timepoints after treatment revealed that compared to Saline (Control), treatment with CNP-301 resulted in a statistically significant increase from baseline (Day 8) in the frequency of cell-surface IL-15 expressing myeloid cells on Day 20 (FIG. 7A), activated CD244+NK cells on Day 14 (FIG. 7B), activated Perforin$^+$ NK cells on Day 20 (FIG. 7C), and activated Granzyme$^+$ NK cells on Day 20 (FIG. 7D) in the tumors.

Together, these data demonstrate that treatment with CNP-301 induces pro-inflammatory immunological changes in blood and tumors of B16F10 tumor-bearing mice.

Example 5

Treatment with Surface Functionalized Particles Induces Pro-Inflammatory Immunological Changes in the Blood and Tumor of MC38 Tumor-Bearing Mice The efficacy of CNP-301 at inducing pro-inflammatory anti-tumor immunological changes in MC38 tumor-bearing mice was also examined. Briefly, 6-8-week-old C57BL/6 mice were subcutaneously injected with B16F10 tumor cells. After palpable tumor formation (~50 $mm^3$), animals were treated with Saline (Control) or CNP-301. Animals were treated once every three days. CNP-301 was administered via tail vein injection at a dose of 1 mg/mouse.

The following parameters were evaluated at different timepoints [Day 7 (prior to 1st dose), Day 14 (24 hours after the 3rd dose), and Day 20 (24 hours after the 5th dose) after tumor injection]: pro-inflammatory cytokines/chemokines in blood by ELISA, myeloid-cell phenotypes in blood and tumor by flow cytometry, and lymphoid-cell functional phenotypes in blood and tumor by flow cytometry.

Figures 8A, 8B, 8C:
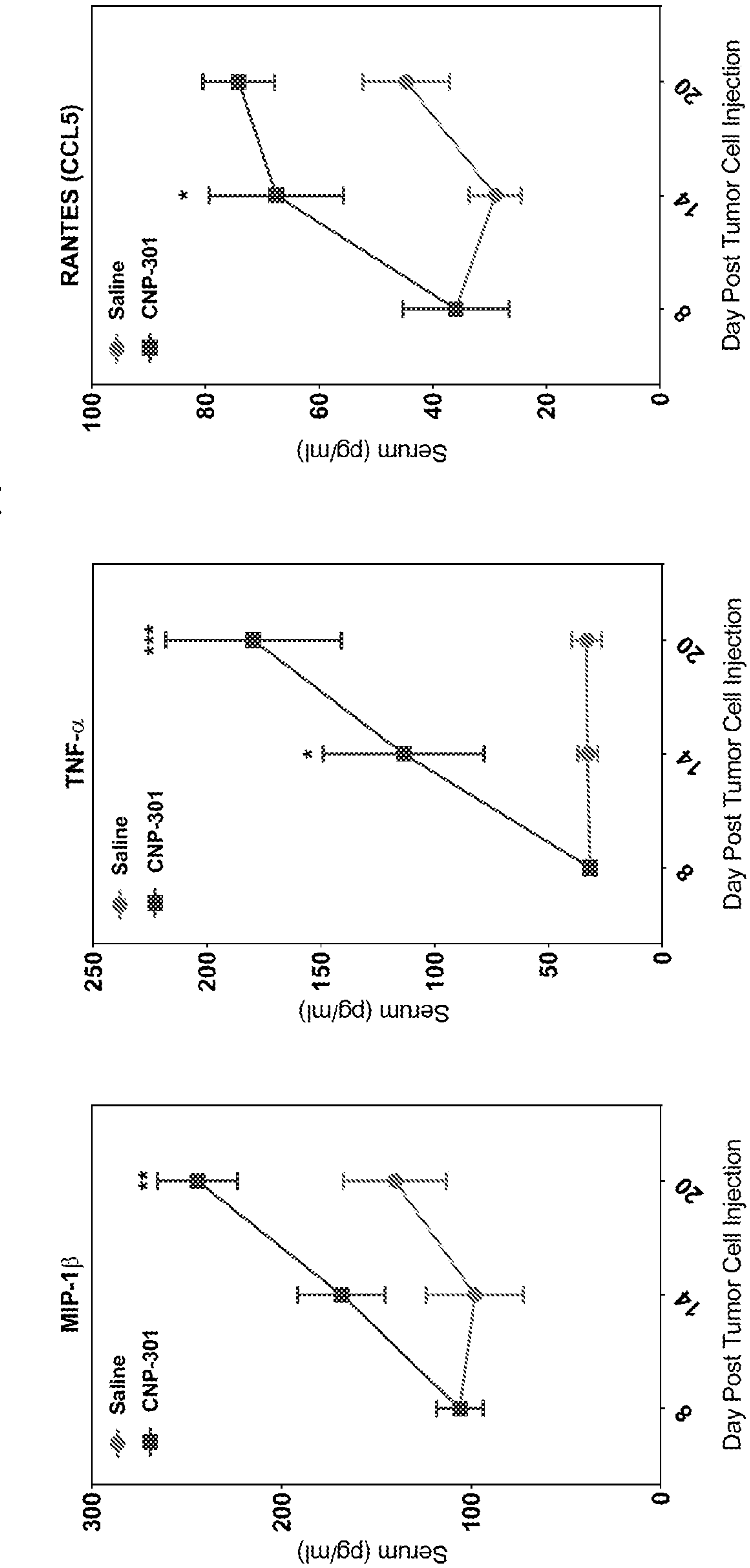
FIGS. 8A-8E shows the effect of treatment with surface functionalized particles, CNP-301, on cytokine/chemokine levels in blood of MC38 tumor-bearing mice. C57BL/6 mice were subcutaneously injected with MC38 tumor cells. Treatment with Saline or CNP-301 was initiated after palpable tumor formation. Treatment was administered via iv injection once every three days. Levels of indicated cytokines and chemokines were measured in blood on Day 8 (prior to 1$^{st}$ dose), Day 14 (24 hours after 3$^{rd}$ dose), and Day 20 (24 hours after 5$^{th}$ dose) (FIG. 8A, MIP-1β.

As shown in FIG. 8A, compared to Saline (Control), treatment with CNP-301 led to a significant reduction in tumor growth. CNP-301-mediated inhibition of tumor growth was observed beginning on Day 14 after tumor injection, or after 3 doses, and continued to inhibit tumor growth until Day 20.

Figures 8D, 8E:
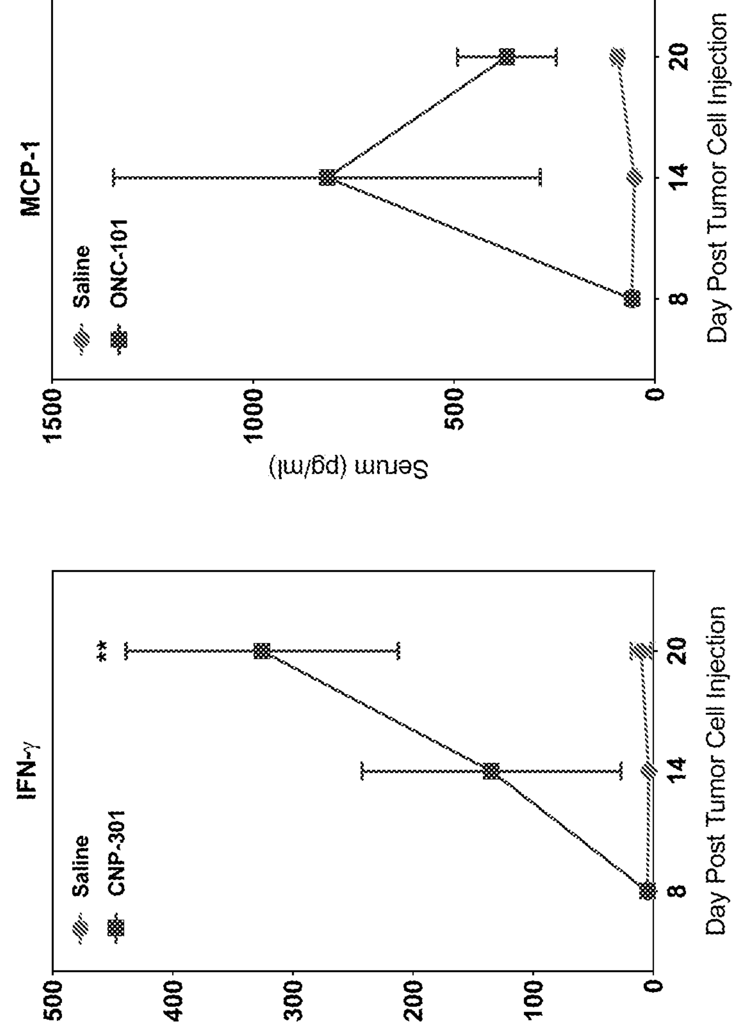
Figure 9A:
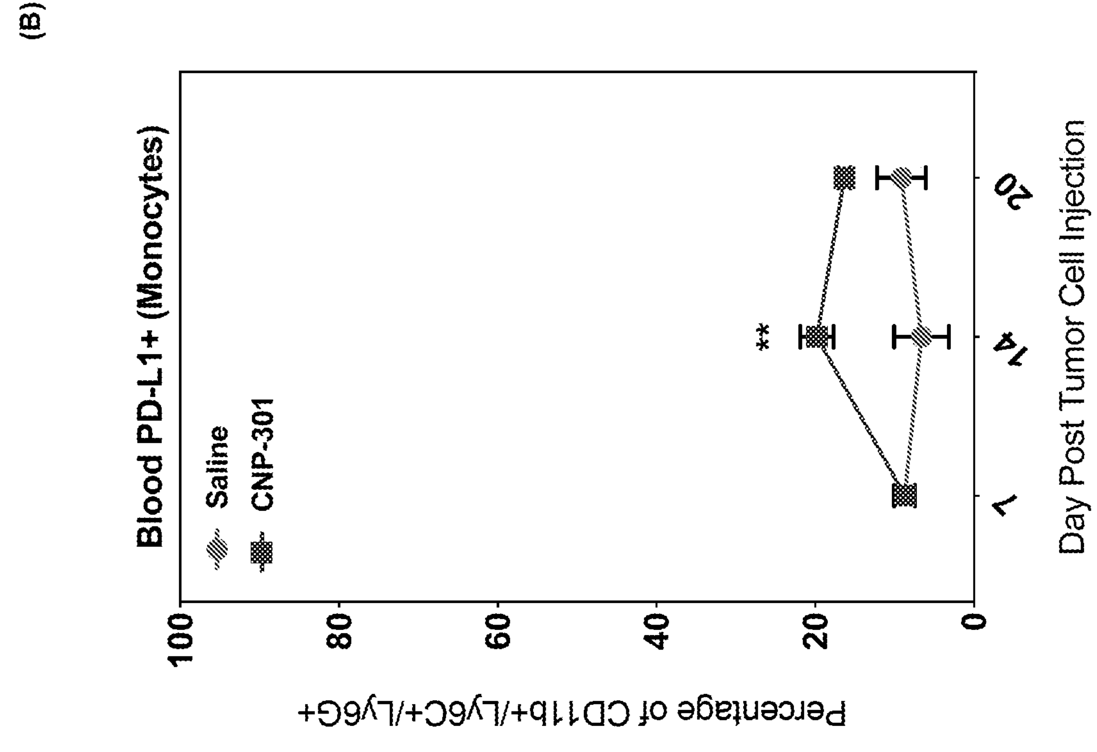
FIG. 9A-9G shows the effect of treatment with surface functionalized particles, CNP-301, on immune cells in blood. C57BL/6 mice were subcutaneously injected with MC38 tumor cells. Treatment with Saline or CNP-301 was initiated after palpable tumor formation. Treatment was administered via iv injection once every three days. Frequency of PD-L1+(FIG. 9A) monocytes (CD11b$^+$Ly6C$^+$ Ly6G$^-$) and (FIG. 9B) granulocytes (CD11b$^+$Ly6C$^+$Ly6G$^+$), (FIG. 9C) cell surface IL-15$^+$ cells (CD45$^+$), (FIG. 9D) total NK cells (CD3$^-$NK1.1$^+$), (FIG. 9E) Granzyme$^+$ NK cells (CD3$^-$NK1.1$^+$), (FIG. 9F) Perforin$^+$ NK cells (CD3$^-$ NK1.1$^+$), and (FIG. 9G) CD244$^+$ NK cells (CD3$^-$NK1.1$^+$) in blood was assayed on Day 8 (prior to 1$^{st}$ dose), Day 14 (24 hours after 3$^{rd}$ dose), and Day 20 (24 hours after 5th dose). Immune cells were assayed from blood by flow cytometry. Statistical significance was determined by 2-way ANOVA with Bonferroni's multiple comparison test. N=5 per group.
Figure 9B:
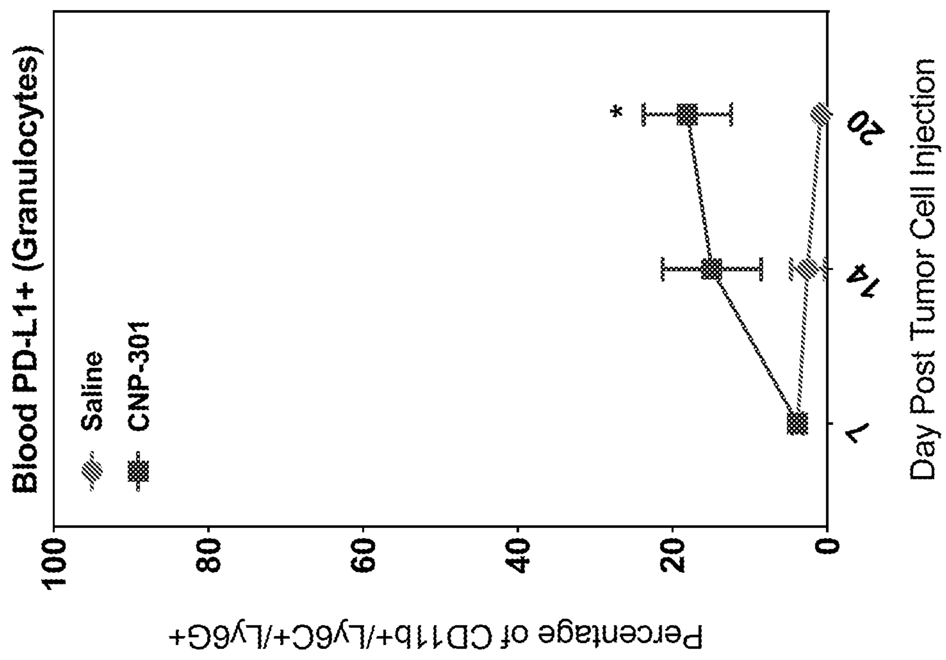
Figures 9C, 9D:
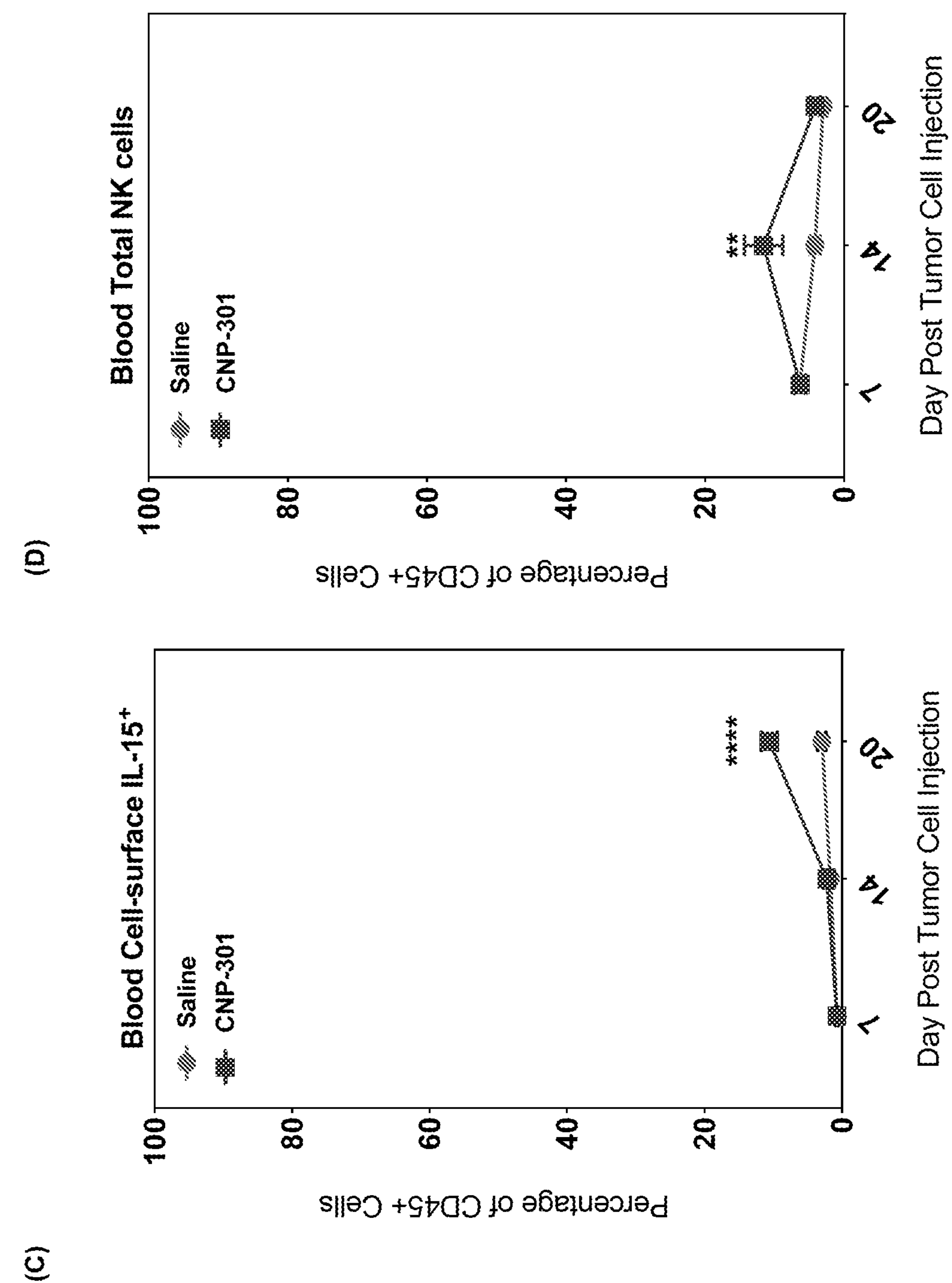
Figure 9E:
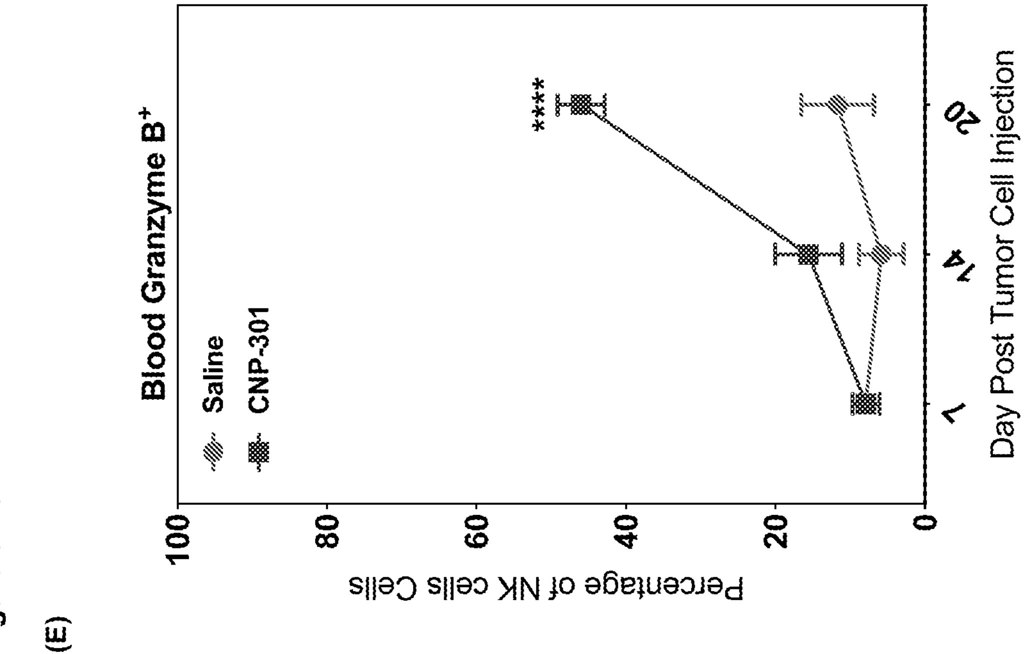
Figure 9F:
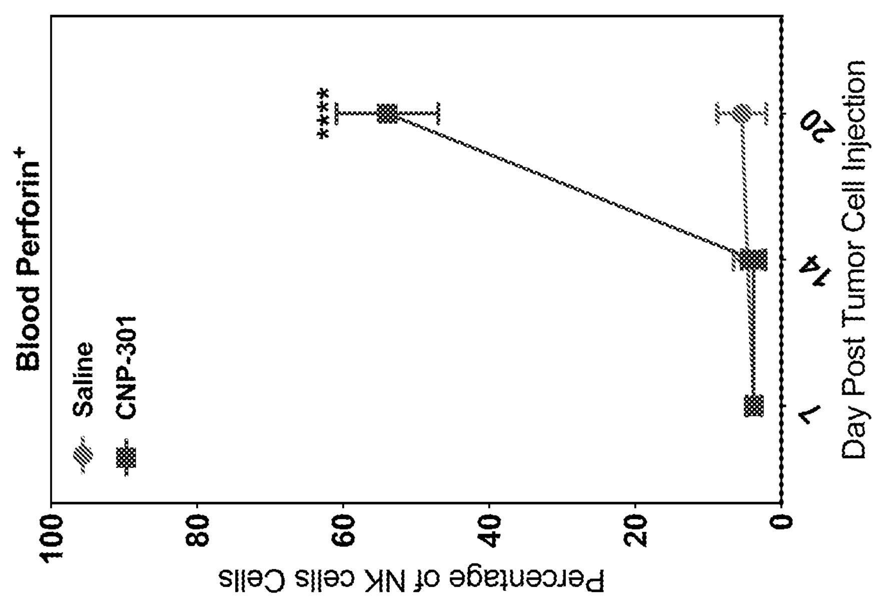
Figure 9G:
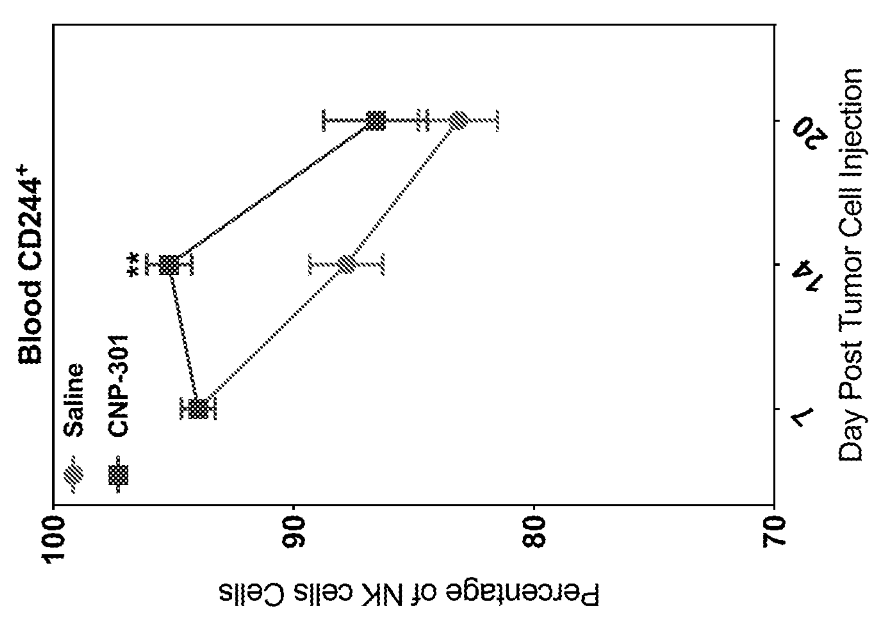

As shown in FIG. 8B-8D, compared to Saline (Control), CNP-301 treatment led to a statistically significant increase from baseline (Day 8) in the levels of pro-inflammatory cytokines/chemokines MIP-1β, TNF-α, and RANTES on Days 14 and 20. CNP-301 treatment also led to an increase from baseline (Day 8) in the levels of IFN-γ and MCP-1 on Day 14; however, this increase was not statistically significant.

As shown in FIG. 9, compared to Saline (Control), CNP-301 treatment led to a statistically significant increase from baseline (Day 8) in the frequency of PD-L1$^+$ monocytes (FIG. 9A) and granulocytes (FIG. 9B) in blood on Days 14 and 20, respectively. PD-L1$^+$ expression on myeloid cells is associated with immunoregulatory functions and is induced upon activation of these cells. Consistent with an activation phenotype, CNP-301 treatment lead to a statistically significant increase from baseline (Day 7) in the frequency of myeloid cells expressing IL-15 on their cell surface in blood on Day 20 (FIG. 9C). In accordance with the observed increase in IL-15, CNP-301 treatment also led to a statistically significant increase from baseline in the frequency of total NK cells (FIG. 9D) and activated (Granzyme$^+$, Perforin$^+$, and CD244+) NK cells (FIG. 9E-9G) in blood on Days 14 and 20.

Together, these data demonstrate that treatment with CNP-301 induces pro-inflammatory immunological changes in blood of MC38 tumor-bearing mice.

Example 6

Efficacy of Surface Functionalized Particles is Dependent on the Presence of IL-15 and NK Cells in the B16F10 Tumor Model As shown in Example 4 and Example 5, treatment with CNP-301 led to induction of cell-surface IL-15 expression on myeloid cells along with activation of NK cells. It was next examined whether the efficacy of CNP-301 at inhibiting tumor growth was dependent on the presence of IL-15 and NK cells.

First, the effect of anti-IL-15 antibody-mediated IL-15 blockade on the efficacy of CNP-301 at inhibiting tumor growth was assessed. Briefly, 6-8-week-old C57BL/6 mice were subcutaneously injected with B16F10 tumor cells. After palpable tumor formation (~50 mm$^3$), animals were randomized into the following treatment groups:

Saline (Control)+Isotype control antibody
Saline (Control)+Anti-IL-15
CNP-301+Isotype control antibody
CNP-301+Anti-IL-15 antibody Animals received CNP-301 treatment once every three days. CNP-301 was administered via tail vein injection at a dose of 1 mg/mouse. Animals were administered a dose of 100 μg anti-IL-15 or isotype control antibody via intraperitoneal injection once every three days. Tumor growth was monitored routinely by measuring tumors using standard calipers. Tumor volumes were calculated using the following formula:

$$\text{Tumor Volume}=0.5(\text{length})\times(\text{width})^2$$

Figure 10:
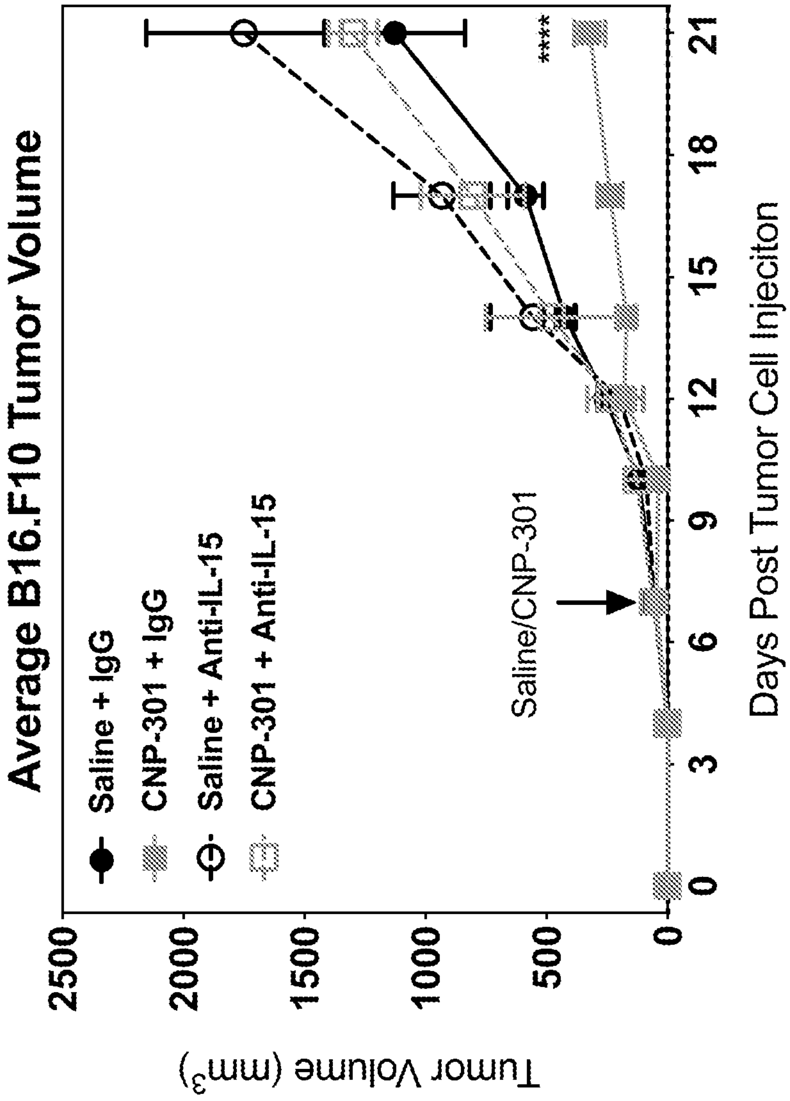
FIG. 10 shows the effect of IL-15 blockade on efficacy of surface functionalized particles, CNP-301, in B16F10 tumor model. C57BL/6 mice were injected subcutaneously with B16F10 tumor cells. Animals were treated with Saline or CNP-301 with or without anti-IL-15 antibody after palpable tumor formation (50 mm$^3$). Isotype IgG antibody was used as control. Saline/CNP-301 was administered via intravenous injection. Isotype/anti-IL-15 antibody was administered via intraperitoneal injection. All treatments were administered once every three days. Isotype/anti-IL15 treatments were administered beginning one day before initiation of Saline/CNP-301. Shown are tumor volumes of mice treated with saline or CNP-301 in the presence (IgG) or absence of (Anti-IL-15) IL-15. Statistical significance was determined by 2-way ANOVA with Bonferroni's multiple comparison test. N=5 per group.

As shown in FIG. 10, compared to Saline, CNP-301 treatment in the absence of IL-15 blockade (Isotype control) inhibited B16F10 tumor growth. IL-15 blockade (anti-IL-15) reversed CNP-301 anti-tumor efficacy and exacerbated tumor growth in the Saline treatment group. Together, these data demonstrate that CNP-301 efficacy is dependent on the presence of IL-15.

Next, the effect of anti-NK1.1 antibody-mediated depletion of NK cells on the efficacy of CNP-301 at inhibiting tumor growth was examined in the B16F10 tumor model. Briefly, 6-8-week-old C57BL/6 mice were subcutaneously injected with B16F10 tumor cells. After palpable tumor formation (~50 mm$^3$), animals were randomized into the following treatment groups:

Saline (Control)+Isotype control antibody
Saline (Control)+Anti-NK1.1
CNP-301+Isotype control antibody
CNP-301+Anti-NK1.1

Animals received CNP-301 treatment once every three days. CNP-301 was administered via tail vein injection at a dose of 1 mg/mouse. Anti-NK1.1/Isotype antibody treatments were administered beginning one day prior to treatment with Saline/CNP-301. Animals were administered a dose of 100 μg anti-NK1.1 or isotype control antibody via intraperitoneal injection once every three days. Tumor growth was monitored routinely by measuring tumors using standard calipers. Tumor volumes were calculated using the following formula:

$$\text{Tumor Volume}=0.5(\text{length})\times(\text{width})^2$$

Figure 11:
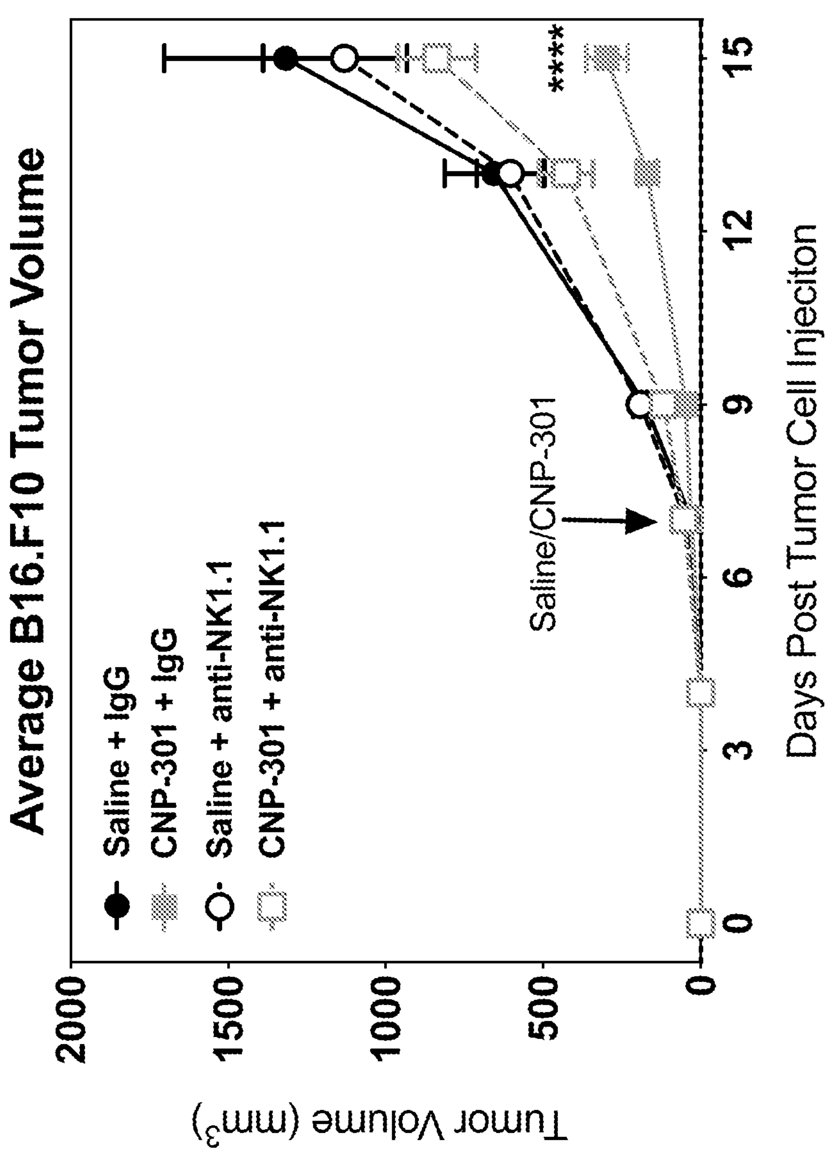
FIG. 11 shows the effect of NK cell depletion on efficacy of surface functionalized particles, CNP-301, in B16F10 tumor model. C57BL/6 mice were injected subcutaneously with B16F10 tumor cells. Animals were treated with Saline or CNP-301 with or without anti-NK1.1 antibody after palpable tumor formation (50 mm$^3$). Isotype antibody was used as control. Saline/CNP-301 was administered via intravenous injection. Isotype/anti-NK1.1 antibody was administered via intraperitoneal injection. All treatments were administered once every three days. Shown are tumor volumes of mice treated with saline or CNP-301 in the presence (IgG) or absence (anti-NK1.1) of NK cells. Statistical significance was determined by 2-way ANOVA with Bonferroni's multiple comparison test. N=5 per group.

As shown in FIG. 11, compared to Saline, CNP-301 treatment in the absence of NK cell depletion (Isotype control) inhibited B16F10 tumor growth. NK cell depletion (anti-NK1.1) reversed CNP-301 anti-tumor efficacy. Together, these data demonstrate that CNP-301 efficacy is dependent on the presence of NK cells.

Example 7

Efficacy of Surface Functionalized Particles is Dependent on the Presence of NK Cells in the MC38 Tumor Model The effect of anti-NK1.1 antibody-mediated depletion of NK cells on the efficacy of surface functionalized particles, e.g. CNP-301, at inhibiting tumor growth was examined in the MC38 tumor model. Briefly, 6-8-week-old C57BL/6 mice were subcutaneously injected with MC38 tumor cells. After palpable tumor formation (~50 mm$^3$), animals were randomized into the following treatment groups:

Saline (Control)+Isotype control antibody
Saline (Control)+Anti-NK1.1
CNP-301+Isotype control antibody
CNP-301+Anti-NK1.1

Animals received CNP-301 treatment once every three days. CNP-301 was administered via tail vein injection at a dose of 1 mg/mouse. Animals were administered at a dose of 100 μg anti-NK1.1 or isotype control antibody via intraperitoneal injection once every three days. Tumor growth was monitored routinely by measuring tumors using standard calipers. Tumor volumes were calculated using the following formula:

$$\text{Tumor Volume}=0.5(\text{length})\times(\text{width})^2$$

As shown in FIG. 12, compared to Saline, CNP-301 treatment in the absence of NK cell depletion (Isotype control) inhibited MC38 tumor growth. NK cell depletion (anti-NK1.1) reversed CNP-301 anti-tumor efficacy. Together, these data demonstrate that CNP-301 efficacy is dependent on the presence of NK cells.

Example 8

Effect of Surface Functionalized Particles on Myeloid Derived Suppressor Cells (MDSCs)

The effect of surface functionalized particles on myeloid-derived cells was evaluated in the murine 4T1 orthotopic breast cancer model. Briefly, orthotopic 4T1 tumors were established in BALB/c mice by injecting tumor cells into the fourth mammary fat pad. On Day 3 after tumor injection, animals were randomized into one of the following two treatment groups:

Saline (control) (n=4)
CNP-301 (n=4)

Figure 13A:
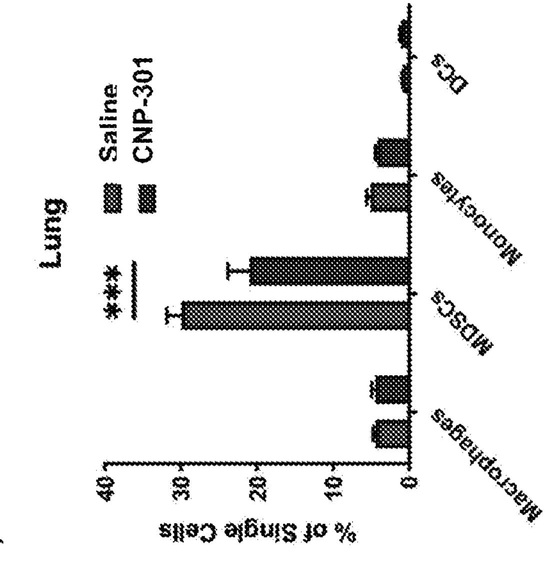
FIG. 13A-13B shows the effect of surface functionalized particles, CNP-301, on myeloid-derived cells in blood and lungs. Orthotopic 4T1 breast tumors were established in BALB/c mice.

Treatments were administered via tail vein injections. CNP-301 was administered at a dose of 1 mg/mouse. Animals were administered a single treatment of Saline or CNP-301 and the levels of macrophages (CD11b$^+$/F4/80$^+$), monocytes (CD11b$^+$Ly6C$^+$), MDSCs (CD11b$^+$/Ly6C$^{lo/-}$/Ly6G$^+$), and dendritic cells (CD11c$^+$) in blood were evaluated by flow cytometry 12-hours post-treatment. As shown in FIG. 13A, treatment with CNP-301 resulted in a significant decrease in the frequency of MDSCs in blood compared to the Saline treatment group ($p<0.001$). Compared to Saline, CNP-301 treatment did not alter the levels of monocytes, macrophages, and dendritic cells in blood after a single treatment.

Figure 13B:
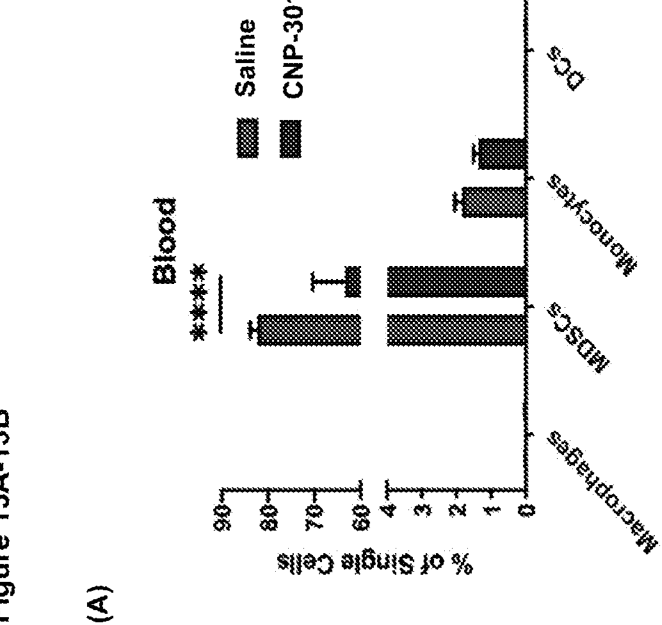

Next, the effect of CNP-301 treatment on myeloid-derived cells in the lungs of 4T1 tumor-bearing mice was evaluated. Lungs are the predominant site of metastasis for orthotopic 4T1 breast tumors. On Day 3 after tumor injection, animals were treated with Saline or CNP-301 for six consecutive days. The levels of ($CD11b^+/F4/80^+$), monocytes ($CD11b^+Ly6C^+$), MDSCs ($CD11b^+/Ly6C^{lo/-}/Ly6G^+$), and dendritic cells ($CD11c^+$) in lungs were evaluated by flow cytometry 24 hours after the last dose. As shown in FIG. 13B, compared to Saline, treatment with CNP-301 led to a significant reduction in the levels of MDSCs in the lungs ($p<0.0001$). CNP-301 did not alter the levels of monocytes, macrophages, and dendritic cells in the lungs.

Together, these data demonstrate that surface functionalized particles, e.g. CNP-301, reduce the number of MDSCs in blood and at metastatic sites.

Example 9

Assay of Cellular Uptake of Surface Functionalized Particles in Tumor-Bearing Mice The cellular uptake of surface functionalized particles, e.g. CNP-301, in tumor-bearing mice was studied in the syngeneic LLC tumor model using fluorescently labeled CNP-301 particles. CNP-301 particles encapsulating fluorescently labeled (Alexa-Fluor 647) ovalbumin were used. Briefly, $5\times10^5$ tumor cells were injected subcutaneously into the shaved flanks of mice. After palpable tumor formation (~50 $mm^2$), mice were randomized into one of the following treatment groups:

Saline (control)

CNP-301

Figure 14A:
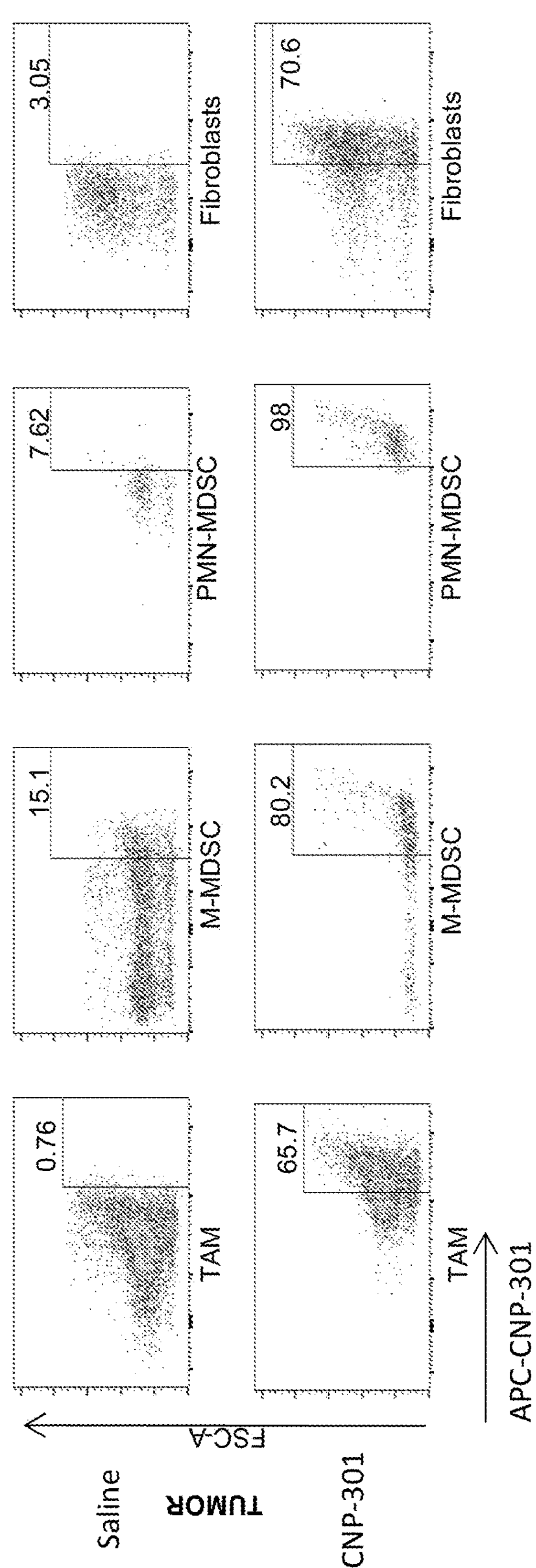
FIGS. 14A-14D shows the results of an assay of cellular uptake of surface functionalized particles, CNP-301, in LLC tumor-bearing mice. LLC tumors were established in C57BL/6 mice. After palpable tumor formation, animals were administered Saline (control) or CNP-301 encapsulating fluorescently labeled (Alexa-Fluor 647) OVA via intravenous injection. Mice were sacrificed 2 hours after iv injection and CNP-301 uptake was assayed by flow cytometry.
Figure 14B:
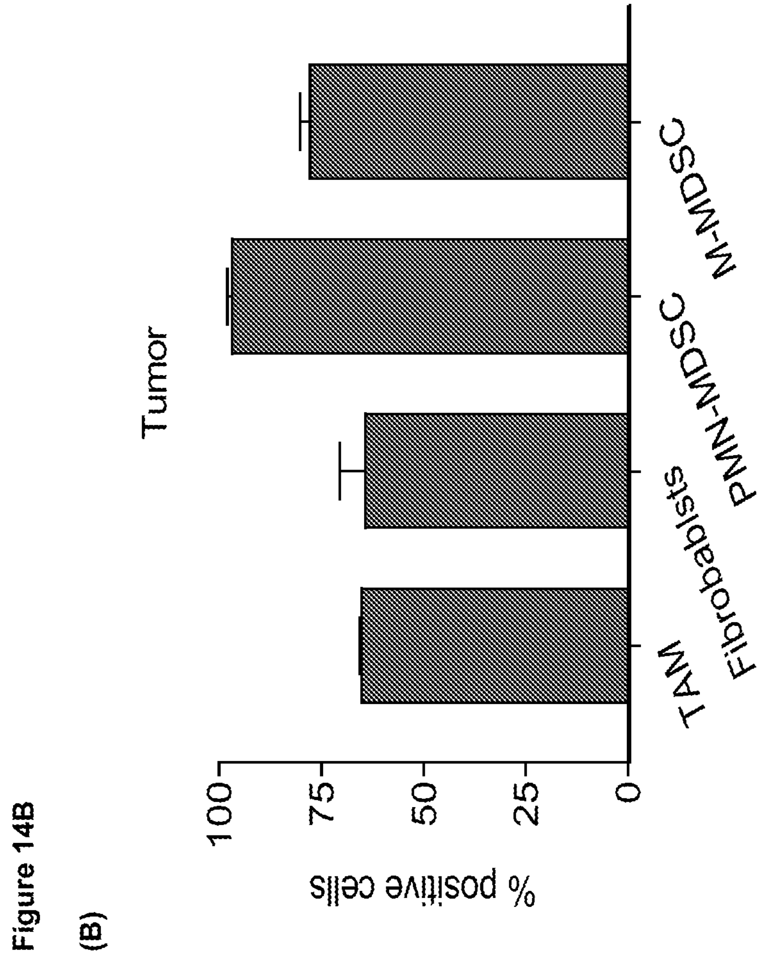
Figure 14C:
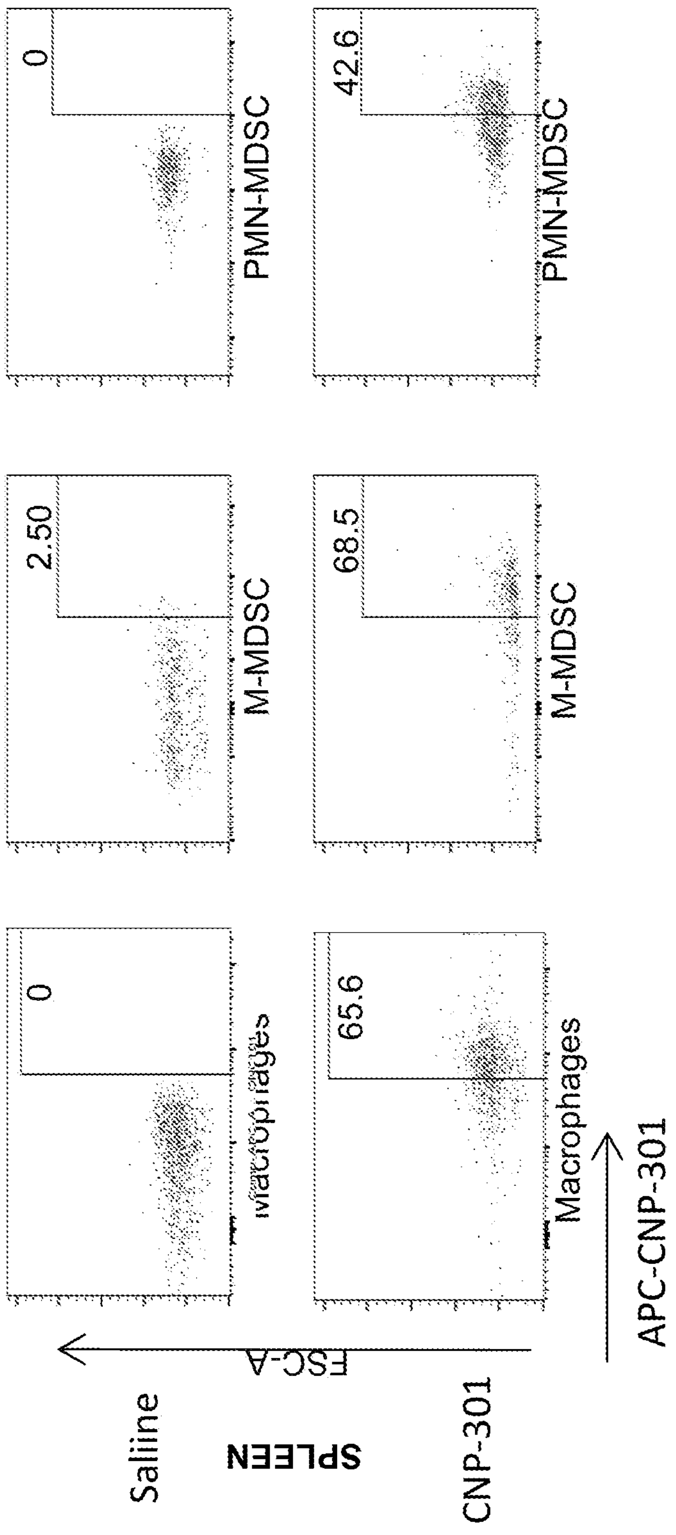
Figure 14D:
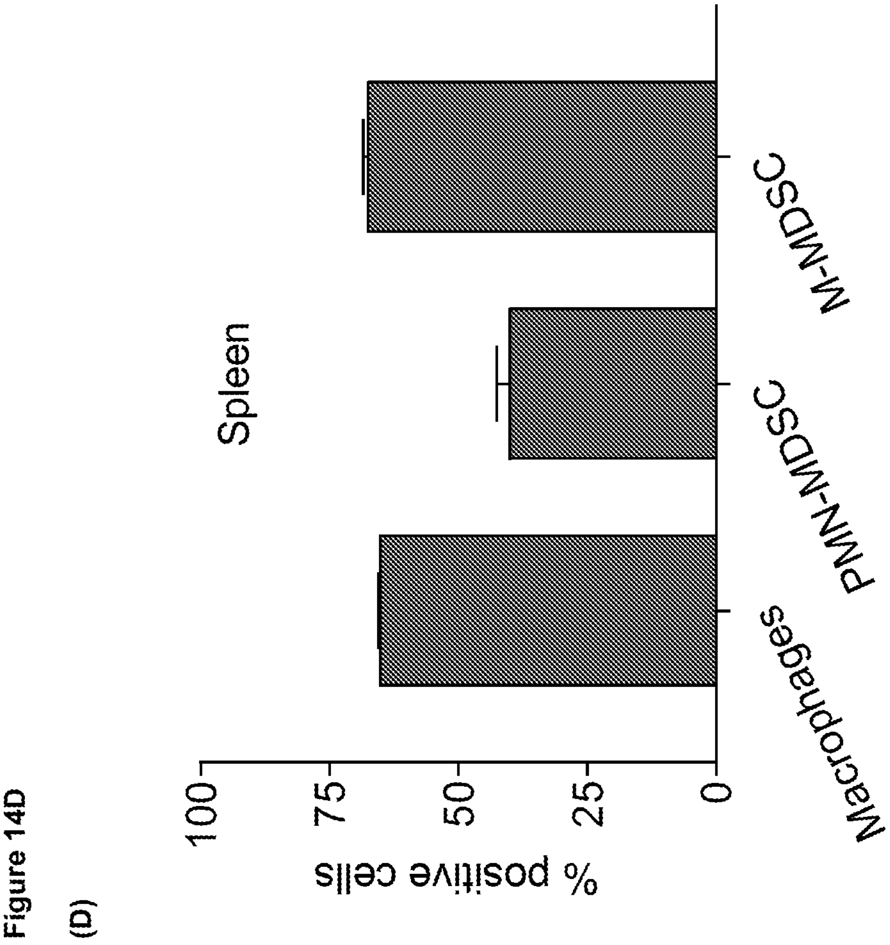

Mice were administered Saline or CNP-301 (1 mg/mouse) via intravenous injection. Two hours after a single intravenous injection, mice were sacrificed and CNP-301 positive cells were analyzed in spleen and LLC tumors by Flow Cytometry. As shown in FIGS. 14A and 14B, a majority of TAMs ($CD11b^+F4/80^+$), M-MDSCs ($CD11b^+Ly6C^+$ $Ly6G^-$), and PMN-MDSCs ($CD11b^+Ly6C^-Ly6G^+$) cells in LLC tumors were positive for CNP-301 2-hours after injection. Furthermore, nearly 75% fibroblasts ($CD45^-CD140a^+$) assayed in the LLC tumors were also positive for CNP-301. Similarly, CNP-301 positive TAMs ($CD11b^+F4/80^+$), M-MDSCs ($CD11b^+Ly6C^+Ly6G^-$), and PMN-MDSCs ($CD11b^+Ly6C^-Ly6G^+$) were also found in the spleen (FIGS. 14C and 14D).

Together, these data demonstrate that CNP-301 is taken up by myeloid-derived cells and fibroblasts after i.v infusion.

Example 10

Effect of Surface Functionalized Particles on Gene Expression in Myeloid-Derived Cells and Fibroblasts in LLC Tumor-Bearing Mice The effect of surface functionalized particles, e.g. CNP-301, on gene expression in myeloid-derived cells and fibroblasts was examined in LLC tumor-bearing mice. Briefly, $5\times10^5$ tumor cells were injected subcutaneously into the shaved flanks of mice. After palpable tumor formation (~50 $mm^2$), mice were randomized into one of the following treatment groups:

Saline (control)

CNP-301

Figure 15A:
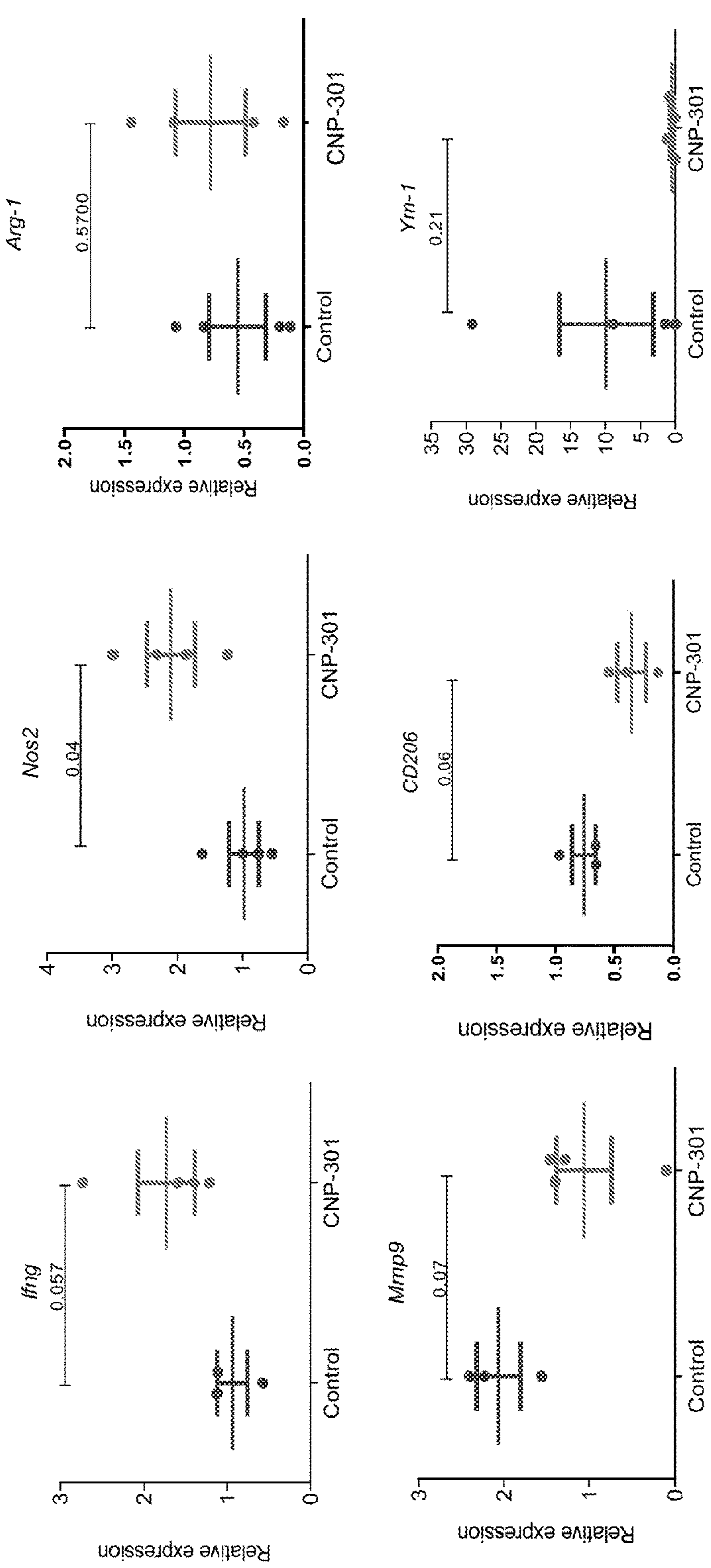
FIGS. 15A-15B shows the effect of surface functionalized particles, CNP-301, on gene expression in tumor associated macrophages and fibroblasts in the LLC tumor. LLC tumors were established in C57BL/6 mice. After palpable tumor formation, animals were administered Saline (control) or CNP-301 via intravenous injection twice per week for two weeks. At the end of treatment, mice were sacrificed, and tumors were harvested.

Mice were administered Saline or CNP-301 (1 mg/mouse) via intravenous injection. Mice were administered the indicated treatments twice per week for two weeks. At the end of the treatment period, mice were sacrificed and tumors were harvested. TAMs ($CD11b^+F4/80^+$) and fibroblasts ($CD45^-CD140a^+$) were isolated from tumors by fluorescence activated cell sorting (FACS). Effect of CNP-301 treatment on gene expression in TAMs and fibroblasts was determined by quantitative polymerase chain reaction (qPCR). Compared to Saline, CNP-301 treatment resulted in a clear trend of a shift in TAM phenotype, at the gene-expression level, from an anti-inflammatory/pro-tumor M2 to a pro-inflammatory/anti-tumor M1 phenotype. Trends of increased expression of pro-inflammatory Ifnγ and Nos2 genes associated with M1 TAMs, and decreased expression of Cd206 and Ym-1 genes associated with pro-tumor M2 TAMs were observed after CNP-301 treatment. Additionally, expression of Mmp9, that encodes for an ECM remodeling protease implicated in tumor progression and metastasis, was also decreased in TAMs after CNP-301 treatment (FIG. 15A).

Figure 15B:
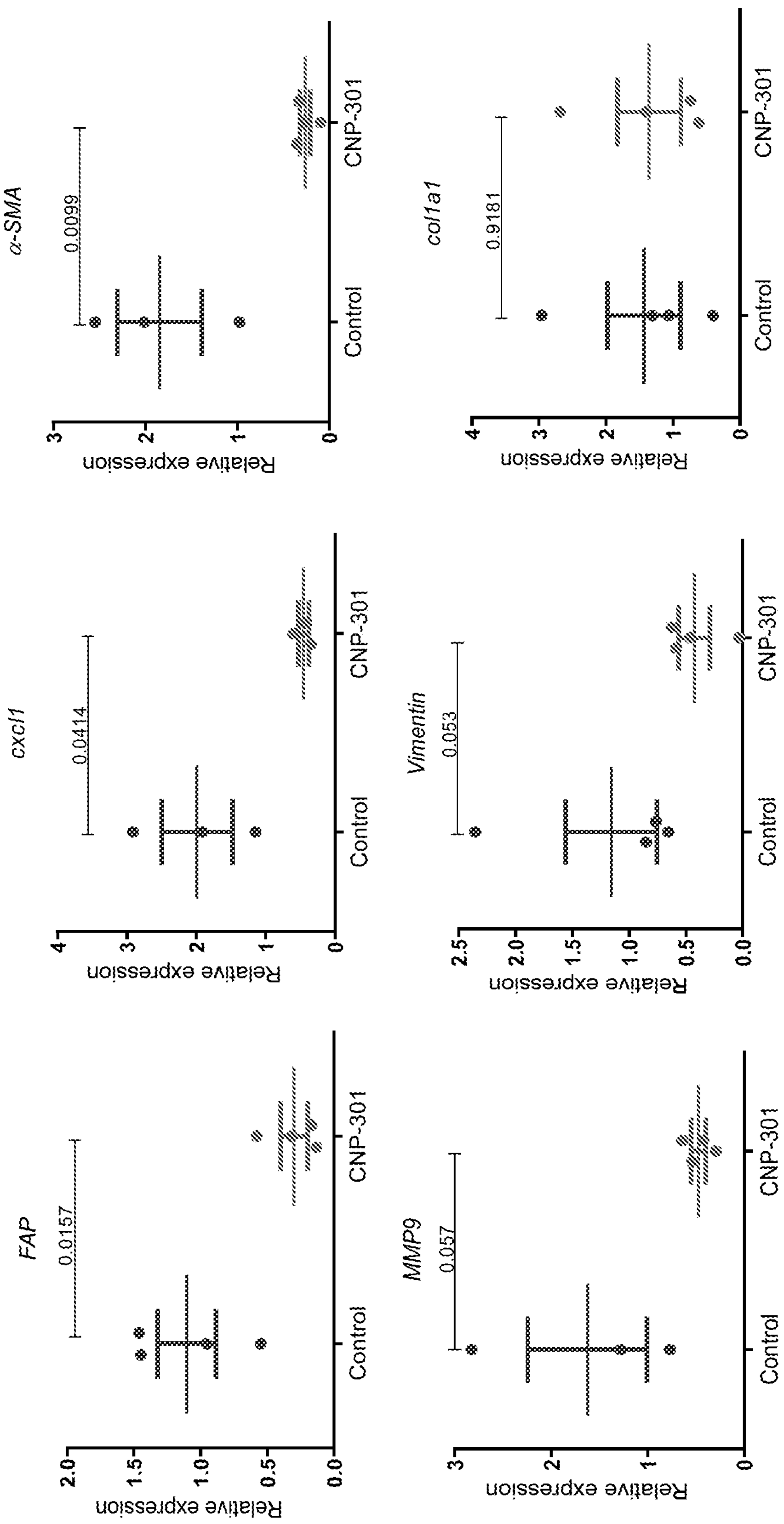

As shown in FIG. 15B, treatment with CNP-301 led to a statistically significant reduction in the expression of Fap, Cxcl1, αSma, and Vim genes in fibroblasts isolated from LLC tumors. These genes are known to be associated with pro-tumorigenic cancer associated fibroblasts indicating that CNP-301 treatment inhibited pro-tumorigenic function of cancer-associated fibroblasts.

Together, these data demonstrate that CNP-301 treatment results in a phenotypic changes in TAMs and fibroblasts in LLC tumors associated with a shift in the tumor microenvironment from pro-tumor state to an anti-tumor state.

Numerous modifications and variations in the disclosure as set forth in the above illustrative examples are expected to occur to those skilled in the art. Consequently, only such limitations as appear in the appended claims should be placed on the disclosure.

REFERENCES

1. Mittal, D., Gubin, M. M., Schreiber, R. D., and Smyth, M. J. (2014) New insights into cancer immunoediting and its three component phases—elimination, equilibrium and escape. *Current opinion in immunology* 27, 16-25
2. Schreiber, R. D., Old, L. J., and Smyth, M. J. (2011) Cancer immunoediting: integrating immunity's roles in cancer suppression and promotion. *Science* (New York, N.Y.) 331, 1565-1570
3. Shankaran, V., Ikeda, H., Bruce, A. T., White, J. M., Swanson, P. E., Old, L. J., and Schreiber, R. D. (2001) IFNgamma and lymphocytes prevent primary tumour development and shape tumour immunogenicity. *Nature* 410, 1107-1111
4. Spel, L., Boelens, J. J., Nierkens, S., and Boes, M. (2013) Antitumor immune responses mediated by dendritic cells: How signals derived from dying cancer cells drive antigen cross-presentation. *Oncoimmunology* 2, e26403
5. Asano, K., Nabeyama, A., Miyake, Y., Qiu, C. H., Kurita, A., Tomura, M., Kanagawa, O., Fujii, S., and Tanaka, M. (2011) CD169-positive macrophages dominate antitumor immunity by crosspresenting dead cell-associated antigens. *Immunity* 34, 85-95

6. Nielsen, J. S., Sahota, R. A., Milne, K., Kost, S. E., Nesslinger, N. J., Watson, P. H., and Nelson, B. H. (2012) CD20+ tumor-infiltrating lymphocytes have an atypical CD27-memory phenotype and together with CD8+ T cells promote favorable prognosis in ovarian cancer. *Clinical cancer research: an official journal of the American Association for Cancer Research* 18, 3281-3292
7. Rubtsov, A. V., Rubtsova, K., Kappler, J. W., Jacobelli, J., Friedman, R. S., and Marrack, P. (2015) CD11c-Expressing B Cells Are Located at the T Cell/B Cell Border in Spleen and Are Potent APCs. *Journal of immunology* (Baltimore, Md.: 1950) 195, 71-79
8. Souza-Fonseca-Guimaraes, F., Cursons, J., and Huntington, N. D. (2019) The Emergence of Natural Killer Cells as a Major Target in Cancer Immunotherapy. *Trends in immunology* 40, 142-158
9. Bonaventura, P., Shekarian, T., Alcazer, V., Valladeau-Guilemond, J., Valsesia-Wittmann, S., Amigorena, S., Caux, C., and Depil, S. (2019) Cold Tumors: A Therapeutic Challenge for Immunotherapy. *Frontiers in immunology* 10, 168
10. Topalian, S. L., Drake, C. G., and Pardoll, D. M. (2015) Immune checkpoint blockade: a common denominator approach to cancer therapy. *Cancer cell* 27, 450-461
11. Thomas, D. A., and Massague, J. (2005) TGF-beta directly targets cytotoxic T cell functions during tumor evasion of immune surveillance. *Cancer cell* 8, 369-380
12. Chao, M. P., Weissman, I. L., and Majeti, R. (2012) The CD47-SIRPalpha pathway in cancer immune evasion and potential therapeutic implications. *Current opinion in immunology* 24, 225-232
13. Le, D. T., Durham, J. N., Smith, K. N., Wang, H., Bartlett, B. R., Aulakh, L. K., Lu, S., Kemberling, H., Wilt, C., Luber, B. S. Wong, F., Azad, N. S., Rucki, A. A., Laheru, D., Donehower, R., Zaheer, A., Fisher, G. A., Crocenzi, T. S., Lee, J. J., Greten, T. F., Duffy, A. G., Ciombor, K. K., Eyring, A. D., Lam, B. H., Joe, A., Kang, S. P., Holdhoff, M., Danilova, L., Cope, L., Meyer, C. Zhou, S., Goldberg, R. M., Armstrong, D. K., Bever, K. M., Fader, A. N., Taube, J., Housseau, F., Spetzler, D., Xiao, N., Pardoll, D. M., Papadopoulos, N., Kinzler, K. W., Eshleman, J. R., Vogelstein, B., Anders, R. A., and Diaz, L. A., Jr. (2017) Mismatch repair deficiency predicts response of solid tumors to PD-1 blockade. *Science* (New York, N.Y.) 357, 409-413
14. Yarchoan, M., Hopkins, A., and Jaffee, E. M. (2017) Tumor Mutational Burden and Response Rate to PD-1 Inhibition. *The New England journal of medicine* 377, 2500-2501
15. Gibney, G. T., Weiner, L. M., and Atkins, M. B. (2016) Predictive biomarkers for checkpoint inhibitor-based immunotherapy. *The Lancet. Oncology* 17, e542-e551
16. Maleki Vareki, S. (2018) High and low mutational burden tumors versus immunologically hot and cold tumors and response to immune checkpoint inhibitors. *Journal for immunotherapy of cancer* 6, 157
17. Trujillo, J. A., Sweis, R. F., Bao, R., and Luke, J. J. (2018) T Cell-Inflamed versus Non-T Cell-Inflamed Tumors: A Conceptual Framework for Cancer Immunotherapy Drug Development and Combination Therapy Selection. *Cancer immunology research* 6, 990-1000
18. Kumar, V., Patel, S., Tcyganov, E., and Gabrilovich, D. I. (2016) The Nature of Myeloid-Derived Suppressor Cells in the Tumor Microenvironment. *Trends in immunology* 37, 208-220
19. Gabrilovich, D. I. (2017) Myeloid-Derived Suppressor Cells. *Cancer immunology research* 5, 3-8
20. Qian, B. Z., and Pollard, J. W. (2010) Macrophage diversity enhances tumor progression and metastasis. *Cell* 141, 39-51
21. La Fleur, L., Boura, V. F., Alexeyenko, A., Berglund, A., Ponten, V., Mattsson, J. S. M., Djureinovic, D., Persson, J., Brunnstrom, H., lsaksson, J., Branden, E., Koyi, H., Micke, P., Karlsson, M. C. I., and Botling, J. (2018) Expression of scavenger receptor MARCO defines a targetable tumor-associated macrophage subset in non-small cell lung cancer. *International journal of cancer*
22. Georgoudaki, A. M., Prokopec, K. E., Boura, V. F., Hellqvist, E., Sohn, S., Ostling, J., Dahan, R., Harris, R. A., Rantalainen, M., Klevebring, D., Sund, M., Brage, S. E., Fuxe, J., Rolny, C., Li, F., Ravetch, J. V., and Karlsson, M. C. (2016) Reprogramming Tumor-Associated Macrophages by Antibody Targeting Inhibits Cancer Progression and Metastasis. *Cell reports* 15, 2000-2011
23. Thomas, A., Routh, E. D., Pullikuth, A., Jin, G., Su, J., Chou, J. W., Hoadley, K. A., Print, C., Knowlton, N., Black, M. A., Demaria, S., Wang, E., Bedognetti, D., Jones, W. D., Mehta, G. A., Gatza, M. L., Perou, C. M., Page, D. B., Triozzi, P., and Miller, L. D. (2018) Tumor mutational burden is a determinant of immune-mediated survival in breast cancer. *Oncoimmunology* 7, e1490854
24. Brown, S. D., Warren, R. L., Gibb, E. A., Martin, S. D., Spinelli, J. J., Nelson, B. H., and Holt, R. A. (2014) Neo-antigens predicted by tumor genome meta-analysis correlate with increased patient survival. *Genome research* 24, 743-750
25. Schrock, A. B., Ouyang, C., Sandhu, J., Sokol, E., Jin, D., Ross, J. S., Miller, V. A., Lim, D., Amanam, I., Chao, J., Catenacci, D., Cho, M., Braiteh, F., Klempner, S. J., Ali, S. M., and Fakih, M. (2019) Tumor mutational burden is predictive of response to immune checkpoint inhibitors in MSI-high metastatic colorectal cancer. *Annals of oncology: official journal of the European Society for Medical Oncology*
26. Dudley, J. C., Lin, M. T., Le, D. T., and Eshleman, J. R. (2016) Microsatellite Instability as a Biomarker for PD-1 Blockade. *Clinical cancer research: an official journal of the American Association for Cancer Research* 22, 813-820
27. Le, D. T., Uram, J. N., Wang, H., Bartlett, B. R., Kemberling, H., Eyring, A. D., Skora, A. D., Luber, B. S., Azad, N. S., Laheru, D., Biedrzycki, B., Donehower, R. C., Zaheer, A., Fisher, G. A., Crocenzi, T. S., Lee, J. J., Duffy, S. M., Goldberg, R. M., de la Chapelle, A., Koshiji, M., Bhaijee, F., Huebner, T., Hruban, R. H., Wood, L. D., Cuka, N., Pardoll, D. M., Papadopoulos, N., Kinzler, K. W., Zhou, S., Cornish, T. C., Taube, J. M., Anders, R. A., Eshleman, J. R., Vogelstein, B., and Diaz, L. A., Jr. (2015) PD-1 Blockade in Tumors with Mismatch-Repair Deficiency. *The New England journal of medicine* 372, 2509-2520
28. Li, J., Byrne, K. T., Yan, F., Yamazoe, T., Chen, Z., Baslan, T., Richman, L. P., Lin, J. H., Sun, Y. H., Rech, A. J., Balli, D., Hay, C. A., Sela, Y., Merrell, A. J., Liudahl, S. M., Gordon, N., Norgard, R. J., Yuan, S., Yu, S., Chao, T., Ye, S., Eisinger-Mathason, T. S. K., Faryabi, R. B., Tobias, J. W., Lowe, S. W., Coussens, L. M., Wherry, E. J., Vonderheide, R. H., and Stanger, B. Z. (2018) Tumor Cell-Intrinsic Factors Underlie Heterogeneity of Immune Cell Infiltration and Response to Immunotherapy. *Immunity* 49, 178-193.e177
29. Rybinski, B., and Yun, K. (2016) Addressing intra-tumoral heterogeneity and therapy resistance. *Oncotarget* 7, 72322-72342

30. Therasse, P., et al., *New Guidelines to Evaluate the Response to Treatment in Solid Tumors*. JNCI: Journal of the National Cancer Institute, 2000. 92(3): p. 205-216.

31. Tovoli, F., et al., *Radiologic criteria of response to systemic treatments for hepatocellular carcinoma*. Hepat Oncol, 2017. 4(4): p. 129-137.

32. O, J. H., M. A. Lodge, and R. L. Wahl, *Practical PERCIST: A Simplified Guide to PET Response Criteria in Solid Tumors* 1.0. Radiology, 2016. 280(2): p. 576-84.

33. Kim, J. and A. Hurria, *Determining chemotherapy tolerance in older patients with cancer*. J Natl Compr Canc Netw, 2013. 11(12): p. 1494-502.

34. Péus, D., N. Newcomb, and S. Hofer, *Appraisal of the Karnofsky Performance Status and proposal of a simple algorithmic system for its evaluation*. BMC Med Inform Decis Mak, 2013. 13: p. 72.

35. Staneva, R., et al., *Cancer cells in the tumor core exhibit spatially coordinated migration patterns*. J Cell Sci, 2019. 132(6).

36. Vignjevic, D., et al., *Fascin, a novel target of beta-catenin-TCF signaling, is expressed at the invasive front of human colon cancer*. Cancer Res, 2007. 67(14): p. 6844-53.

What is claimed:

1. A method for treating a subject having an immune evasive cancer and who had previously received immunotherapy or in which the cancer is refractory to immunotherapy, comprising administering to the subject negatively charged particles alone or in combination with a cancer therapeutic, wherein the negatively charged particles comprise: a polyglycolic acid (PGA) polymer, polylactic acid (PLA), poly (lactic-co-glycolic acid) (PLGA), polystyrene, chitosan, polysaccharide, one or more lipids, diamond, iron, zinc, cadmium, gold, silver, or any combination thereof, wherein the particles have a zeta potential between −30 to −100 mV and a size greater than 200 nm and are free from one or more therapeutic agent, wherein the cancer therapeutic is selected from the group consisting of a growth inhibitor, DNA-replication inhibitor, kinase inhibitor, receptor tyrosine kinase inhibitor, signaling cascade inhibitor, angiogenesis inhibitor, metabolic inhibitor, amino acid synthesis inhibitor, selective inhibitor of oncogenic protein, inhibitor of metastasis, inhibitor of anti-apoptosis factor, apoptosis inducer, enzyme inhibitor, nucleoside stimulating inhibitor, antibody-drug conjugate, DNA-damaging agent, cytokines, one or more cell-based therapies, a hormone therapy, one or more cancer vaccines, or one or more immunotherapies selected from the group consisting of: oncolytic virus, oncolytic bacteria or other bacterial compositions, *Bacillus* Calmette-Guerin (BCG), microbiome modulator, Stimulator of interferon genes (STING) pathway modulator, and toll-like receptor (TLR) modulator.

2. The method of claim 1, wherein the negatively charged particles are poly (lactic-co-glycolic acid) (PLGA) particles.

3. The method of claim 1, wherein the negatively charged particles comprise polylactic acid:poly glycolic acid at a ratio from 80:20 to 20:80 poly glycolic acid: poly lactic acid.

4. The method of claim 1, wherein the negatively charged particles comprise one or more carboxyl groups.

5. The method of claim 1, wherein the negatively charged particles have a zeta potential between −80 mV and −30 mV.

6. The method of claim 1, wherein the diameter of the negatively charged particles is between 300 nm to 1000 nm.

7. The method of claim 1, wherein the subject has one or more immunologically cold tumors, one or more tumors with a low tumor mutational burden, one or more microsatellite stable tumors, one or more tumors with low microsatellite instability, and/or one or more tumors with a low tumor immune cell infiltrate.

8. The method of claim 1, wherein the administering transforms an immunologically cold tumor into an immunologically hot tumor.

9. The method of claim 1, wherein the administering reduces tumor size and/or inhibits tumor growth.

10. The method of claim 1, wherein the subject has a cancer selected from the group consisting of brain cancer, skin cancer, eye cancer, breast cancer, prostate cancer, pancreatic cancer, lung cancer, esophageal cancer, head and neck cancer, cervical cancer, liver cancer, colorectal cancer, bone cancer, uterine cancer, ovarian cancer, bladder cancer, endometrial cancer, stomach cancer, gastric cancer, oral cancer, thyroid cancer, kidney cancer, testicular cancer, leukemia, lymphoma, and mesothelioma.

11. The method of claim 1, comprising the combination with the cancer therapeutic, wherein the cancer therapeutic comprises a growth inhibitor, DNA-replication inhibitor, kinase inhibitor, signaling cascade inhibitor, metabolic inhibitor, amino acid synthesis inhibitor, selective inhibitor of oncogenic protein, inhibitor of metastasis, inhibitor of anti-apoptosis factor, apoptosis inducer, enzyme inhibitor, nucleoside signaling inhibitor, antibody-drug conjugate, DNA-damaging agent, cytokines, angiogenesis inhibitor, or a receptor tyrosine kinase inhibitor.

12. The method of claim 1, comprising the combination with the cancer therapeutic, wherein the cancer therapeutic comprises one or more cell-based therapies selected from adoptive cell transfer, tumor-infiltrating leukocyte therapy, chimeric antigen receptor T-cell therapy (CAR-T), NK-cell therapy or stem cell therapy.

13. The method of claim 1, comprising the combination with the cancer therapeutic, wherein the cancer therapeutic comprises a hormone therapy.

14. The method of claim 1, comprising the combination with the cancer therapeutic, wherein the cancer therapeutic comprises one or more cancer vaccines.

15. The method of claim 1, comprising the combination with the cancer therapeutic, wherein the cancer therapeutic comprises one or more immunotherapies selected from the group consisting of: oncolytic virus, oncolytic bacteria or other bacterial compositions, *Bacillus* Calmette-Guerin (BCG), microbiome modulator, Stimulator of interferon genes (STING) pathway modulator, and toll-like receptor (TLR) modulator.

16. The method of claim 1, wherein the negatively charged particles and/or the cancer therapeutic is administered once daily, twice daily, three times per day, seven times per week, six times per week, five times per week, four times per week, three times per week, twice weekly, once weekly, once every two weeks, once every three weeks, once every 4 weeks, once every two months, once every three months, once every 6 months or once per year, and wherein the administering of the negatively charged particles and/or the cancer therapeutic comprises intravenous, oral, nasal, intramuscular, ocular, transdermal, or subcutaneous administration.

17. The method of claim 16, comprising the negatively charged particles, wherein the negatively charged particles are administered once weekly.

18. The method of claim 1, wherein the negatively charged particles are PLGA particles having a zeta potential between −80 to −30 mV and a diameter between 200 and 2000 nm.

* * * * *